United States Patent [19]
Matthews et al.

[11] Patent Number: 5,717,058
[45] Date of Patent: Feb. 10, 1998

[54] PEPTIDE INHIBITORS OF TAX-DEPENDENT TRANSCRIPTION

[75] Inventors: Maura-Ann H. Matthews; Gary L. Stetler; Spencer J. Anthony-Cahill, all of Boulder, Colo.; David C. Anderson, San Bruno, Calif.

[73] Assignee: Somatogen, Inc., Boulder, Colo.

[21] Appl. No.: 199,508

[22] Filed: Feb. 18, 1994

Related U.S. Application Data

[63] Continuation-in-part of Ser. No. 21,536, Feb. 23, 1993, abandoned.

[51] Int. Cl.$^6$ .......................... C07K 14/155; C07K 4/02; C07K 5/00; C07K 7/00
[52] U.S. Cl. .......................... 530/328; 530/324; 530/325; 530/326; 530/327; 530/330
[58] Field of Search .................................. 530/326, 327, 530/328, 330, 820

[56] References Cited

PUBLICATIONS

Fujsawa et al. J. of Virology 65:4525–4528 (1991).
Franklin, A.A. et al/Transactivation by the Human T–Cell Leukemia Virus Tax Protein is Mediated Through Enhanced Binding of Activating Transcription Factor–2 (ATF–2) ATF–2 Response and cAMP Element–Binding Protein (CREB)/JBC/(1993)/268(29), 21225–21231.
Paca–Uccaralertkun, S. et al/In Vitro Selection of DNA Elements Highly Responsive to the Human T–Cell Lymphotropic Virus Type I Transcriptional Activator, Tax/Mol. & Cell. Biology/(1994), 14(1), 456–462.
Wagner, S. & Green, M.R./HTLV–1 Tax Protein Stimulation of DNA Binding of bZIP Proteins by Enhancing Dimerization/Science/(1993), 262, 395–399.
Kushida, S. et al./HTLV–1 Associated Myelopathy/Tropical Spastic Paraparesis–Like Rats by Intravenous Injection of HTLV–1 Producing Rabbit or Human T–Cell Line into Adult WKA Rats/Jpn. J. Cancer Res./(1993), 84, 831–833.
Ishigura, N. et al/A Rat Model of Human T Lymphocyte Virus Type I (HTLV–I) Infection. 1. Humoral Antibody Response, Provirus Integration, and HTLV–I–Associated Myelopathy/Tropical Spastic Paraparesis–Like Myelopathy in Seronegative HTLV–I Carrier Rats/J. Exp. Med./(1992), 176, 981–989.
Feuer, G. et al/Establishment of Human T–Cell Leukemia Virus Type I T–Cell Lymphomas in Severe Combined Immunodeficient Mice/Blood/(1993), 82(3), 722–731.
Kondo, A. et al/A Model of In Vivo Cell Proliferation of Adult T–Cell Leukemia/Blood/(1993), 82(8), 2501–2509.
Unger, T. & Shaul, Y./The X Protein of the Hepatitis B Virus Acts as a Transcription Factor when Targeted to its Responsive Element/EMBO J./(1990), 9(6), 1889–1895.

*Primary Examiner*—John L. LeGuyader
*Attorney, Agent, or Firm*—Henry P. Nowak; Marianne F. Novelli; Theresa A. Brown

[57] ABSTRACT

The present invention relates to regulators of cellular gene transcription, particularly inhibitors of cellular gene transactivating factors and in particular to inhibition of gene transcription in a viral host cell that is subject to regulation by proteins or factors that originate from a virus as well as conjugates or fusion products of the inhibitors and internalization molecules, pharmaceutical compositions that can be used to alleviate or prevent the manifestation of disease states that are the result of unregulated DNA transcription as a result of transactivation, methods of treating diseases that are caused or exacerbated by the presence of transactivating factors, and regulated gene therapy to achieve long term drug delivery of the inhibitors of the present invention. This invention can be applied both to cells with genetic abnormalities or to cells infected with a virus. Preferably, at least one protein of the protein-protein interactions is a transactivating factor.

10 Claims, No Drawings

SEQUENCE LISTING ( 1 ) GENERAL INFORMATION:

( i i i ) NUMBER OF SEQUENCES: 57

( 2 ) INFORMATION FOR SEQ ID NO:1:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:1:

Met Ala His Phe Pro Gly Phe Gly Gln Ser Leu Leu Phe Gly Tyr
1               5                   10                  15
Pro Val Tyr Val Phe
                20

( 2 ) INFORMATION FOR SEQ ID NO:2:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:2:

Phe Gly Tyr Pro Val Tyr Val Phe Gly Asp Cys Val Gln Gly Asp
1               5                   10                  15
Trp Cys Pro Ile Ser
                20

( 2 ) INFORMATION FOR SEQ ID NO:3:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:3:

Gln Gly Asp Trp Cys Pro Ile Ser Gly Gly Leu Cys Ser Ala Arg
1               5                       10                      15

Leu His Arg His Ala
                20

( 2 ) INFORMATION FOR SEQ ID NO:4:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:4:

Ser Ala Arg Leu His Arg His Ala Leu Leu Ala Thr Cys Pro Glu
1               5                       10                      15

His Gln Ile Thr Trp
                20

( 2 ) INFORMATION FOR SEQ ID NO:5:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:5:

Cys Pro Glu His Gln Ile Thr Trp Asp Pro Ile Asp Gly Arg Val
1               5                       10                      15

Ile Gly Ser Ala Leu
                20

( 2 ) INFORMATION FOR SEQ ID NO:6:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:6:

Gly Arg Val Ile Gly Ser Ala Leu Gln Phe Leu Ile Pro Arg Leu
1               5                       10                      15

Pro Ser Phe Pro Thr
                20

( 2 ) INFORMATION FOR SEQ ID NO:7:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:7:

```
Pro  Arg  Leu  Pro  Ser  Phe  Pro  Thr  Gln  Arg  Thr  Ser  Lys  Thr  Leu
1              5                        10                       15

Lys  Val  Leu  Thr  Pro
                    20
```

( 2 ) INFORMATION FOR SEQ ID NO:8:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:8:

```
Lys  Thr  Leu  Lys  Val  Leu  Thr  Pro  Pro  Ile  Thr  His  Thr  Thr  Pro
1              5                        10                       15

Asn  Ile  Pro  Pro  Ser
                    20
```

( 2 ) INFORMATION FOR SEQ ID NO:9:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:9:

```
Thr  Thr  Pro  Asn  Ile  Pro  Pro  Ser  Phe  Leu  Gln  Ala  Met  Arg  Lys
1              5                        10                       15

Tyr  Ser  Pro  Phe  Arg
                    20
```

( 2 ) INFORMATION FOR SEQ ID NO:10:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:10:

```
Met  Arg  Lys  Tyr  Ser  Phe  Arg  Asn  Gly  Tyr  Met  Glu  Pro  Thr
1              5                        10                       15

Leu  Gly  Gln  His  Leu
                    20
```

( 2 ) INFORMATION FOR SEQ ID NO:11:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:11:

Glu Pro Thr Leu Gly Gln His Leu Pro Thr Leu Ser Phe Pro Asp
1               5                   10                  15

Pro Gly Leu Arg Pro
                20

( 2 ) INFORMATION FOR SEQ ID NO:12:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:12:

Phe Pro Asp Pro Gly Leu Arg Pro Gln Asn Leu Tyr Thr Leu Trp
1               5                   10                  15

Gly Gly Ser Val Val
                20

( 2 ) INFORMATION FOR SEQ ID NO:13:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:13:

Thr Leu Trp Gly Gly Ser Val Val Cys Met Tyr Leu Tyr Gln Leu
1               5                   10                  15

Ser Pro Pro Ile Thr
                20

( 2 ) INFORMATION FOR SEQ ID NO:14:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:14:

Tyr Gln Leu Ser Pro Pro Ile Thr Trp Pro Leu Leu Pro His Val
1               5                   10                  15

Ile Phe Cys His Pro
                20

( 2 ) INFORMATION FOR SEQ ID NO:15:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:15:

Pro His Val Ile Phe Cys His Pro Gly Gln Leu Gly Ala Phe Leu

```
 1               5                    1 0                  1 5

Thr Asn Val Pro Tyr
                 2 0
```

( 2 ) INFORMATION FOR SEQ ID NO:16:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:16:

```
Ala Phe Leu Thr Asn Val Pro Tyr Lys Arg Ile Glu Glu Leu Leu
 1               5                    1 0                  1 5

Tyr Lys Ile Ser Leu
                 2 0
```

( 2 ) INFORMATION FOR SEQ ID NO:17:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:17:

```
Glu Leu Leu Tyr Lys Ile Ser Leu Thr Thr Gly Ala Leu Ile Ile
 1               5                    1 0                  1 5

Leu Pro Glu Asp Cys
                 2 0
```

( 2 ) INFORMATION FOR SEQ ID NO:18:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:18:

```
Leu Ile Ile Leu Pro Glu Asp Cys Leu Pro Thr Thr Leu Phe Gln
 1               5                    1 0                  1 5

Pro Ala Arg Ala Pro
                 2 0
```

( 2 ) INFORMATION FOR SEQ ID NO:19:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:19:

```
Leu Phe Gln Pro Ala Arg Ala Pro Val Thr Leu Thr Ala Trp Gln
```

```
                1                       5                      10                      15
Asn Gly Leu Leu Pro
                        20
```

(2) INFORMATION FOR SEQ ID NO:20:

(i) SEQUENCE CHARACTERISTICS:
        (A) LENGTH: 20
        (B) TYPE: amino acid
        (D) TOPOLOGY: unknown to applicant (ii) MOLECULE TYPE: peptide (iii) HYPOTHETICAL: yes (xi) SEQUENCE DESCRIPTION: SEQ ID NO:20:

```
Ala Trp Gln Asn Gly Leu Leu Pro Phe His Ser Thr Leu Thr Thr
 1                   5                  10                  15
Pro Gly Leu Ile Trp
                        20
```

(2) INFORMATION FOR SEQ ID NO:21:

(i) SEQUENCE CHARACTERISTICS:
        (A) LENGTH: 20
        (B) TYPE: amino acid
        (D) TOPOLOGY: unknown to applicant (ii) MOLECULE TYPE: peptide (iii) HYPOTHETICAL: yes (xi) SEQUENCE DESCRIPTION: SEQ ID NO:21:

```
Leu Thr Thr Pro Gly Leu Ile Trp Thr Phe Thr Asp Gly Thr Pro
 1                   5                  10                  15
Met Ile Ser Gly Pro
                        20
```

(2) INFORMATION FOR SEQ ID NO:22:

(i) SEQUENCE CHARACTERISTICS:
        (A) LENGTH: 20
        (B) TYPE: amino acid
        (D) TOPOLOGY: unknown to applicant (ii) MOLECULE TYPE: peptide (iii) HYPOTHETICAL: yes (xi) SEQUENCE DESCRIPTION: SEQ ID NO:22:

```
Gly Thr Pro Met Ile Ser Gly Pro Cys Pro Lys Asp Gly Gln Pro
 1                   5                  10                  15
Ser Leu Val Leu Gln
                        20
```

(2) INFORMATION FOR SEQ ID NO:23:

(i) SEQUENCE CHARACTERISTICS:
        (A) LENGTH: 20
        (B) TYPE: amino acid
        (D) TOPOLOGY: unknown to applicant (ii) MOLECULE TYPE: peptide (iii) HYPOTHETICAL: yes (xi) SEQUENCE DESCRIPTION: SEQ ID NO:23:

```
Gly Gln Pro Ser Leu Val Leu Gln Ser Ser Ser Phe Ile Phe His
```

```
         1               5                    10                    15
Lys  Phe  Gln  Thr  Lys
                    20
```

( 2 ) INFORMATION FOR SEQ ID NO:24:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:24:

```
Ile  Phe  His  Lys  Phe  Gln  Thr  Lys  Ala  Tyr  His  Pro  Ser  Phe  Leu
 1                   5                        10                        15
Leu  Ser  His  Gly  Leu
                    20
```

( 2 ) INFORMATION FOR SEQ ID NO:25:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:25:

```
Ser  Phe  Leu  Leu  Ser  His  Gly  Leu  Ile  Gln  Tyr  Ser  Ser  Phe  His
 1                   5                        10                        15
Ser  Leu  His  Leu  Leu
                    20
```

( 2 ) INFORMATION FOR SEQ ID NO:26:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:26:

```
Ser  Phe  His  Ser  Leu  His  Leu  Leu  Phe  Glu  Glu  Tyr  Thr  Asn  Ile
 1                   5                        10                        15
Pro  Ile  Ser  Leu  Leu
                    20
```

( 2 ) INFORMATION FOR SEQ ID NO:27:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:27:

```
Thr  Asn  Ile  Pro  Ile  Ser  Leu  Leu  Phe  Asn  Glu  Lys  Glu  Ala  Asp
 1                   5                        10                        15
```

Asp Asn Ala His Glu
                 20

( 2 ) INFORMATION FOR SEQ ID NO:28:

( i ) SEQUENCE CHARACTERISTICS:
        ( A ) LENGTH: 20
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:28:

Glu Ala Asp Asp Asn Ala His Glu Pro Gln Ile Ser Pro Gly Gly
 1               5                  10                   15
Leu Glu Pro Pro Ser
                 20

( 2 ) INFORMATION FOR SEQ ID NO:29:

( i ) SEQUENCE CHARACTERISTICS:
        ( A ) LENGTH: 17
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:29:

Pro Gly Gly Leu Glu Pro Pro Ser Glu Lys His Phe Arg Glu Thr
 1               5                  10                   15
Glu Val ( 2 ) INFORMATION FOR SEQ ID NO:30:

( i ) SEQUENCE CHARACTERISTICS:
        ( A ) LENGTH: 15
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:30:

Asp Pro Ile Asp Gly Arg Val Ile Gly Ser Ala Lys Gln Phe Leu
 1               5                  10                   15

( 2 ) INFORMATION FOR SEQ ID NO:31:

( i ) SEQUENCE CHARACTERISTICS:
        ( A ) LENGTH: 15
        ( B ) TYPE: amino acid
        ( D ) TOPOLOGY: unknown to applicant ( i i ) MOLECULE TYPE: peptide ( i i i ) HYPOTHETICAL: yes ( x i ) SEQUENCE DESCRIPTION: SEQ ID NO:31:

Lys Ala Tyr His Pro Ser Phe Leu Leu Ser His Gly Leu Ile Gln
 1               5                  10                   15

( 2 ) INFORMATION FOR SEQ ID NO:32:

(i) SEQUENCE CHARACTERISTICS:
  (A) LENGTH: 15
  (B) TYPE: amino acid
  (D) TOPOLOGY: unknown to applicant (ii) MOLECULE TYPE: peptide (iii) HYPOTHETICAL: yes (xi) SEQUENCE DESCRIPTION: SEQ ID NO:32:

| Phe | Asn | Glu | Lys | Glu | Ala | Asp | Asp | Asn | Asp | His | Glu | Pro | Gln | Ile |
|-----|-----|-----|-----|-----|-----|-----|-----|-----|-----|-----|-----|-----|-----|-----|
| 1   |     |     |     | 5   |     |     |     |     | 10  |     |     |     |     | 15  |

(2) INFORMATION FOR SEQ ID NO:33:

(i) SEQUENCE CHARACTERISTICS:
    (A) LENGTH: 62
    (B) TYPE: nucleic acid
    (C) STRANDEDNESS: single
    (D) TOPOLOGY: linear (ii) MOLECULE TYPE: Genomic DNA (iii) HYPOTHETICAL: yes (xi) SEQUENCE DESCRIPTION: SEQ ID NO:33:

GATCTCTAGC AGGAGTCTAT AAAAGCGTGG AGACAGTTCA GGAGGGGGCT      50

CGCATCTCTC CA      62

(2) INFORMATION FOR SEQ ID NO:34:

(i) SEQUENCE CHARACTERISTICS:
    (A) LENGTH: 27
    (B) TYPE: nucleic acid
    (C) STRANDEDNESS: single
    (D) TOPOLOGY: linear (ii) MOLECULE TYPE: Genomic DNA (iii) HYPOTHETICAL: yes (xi) SEQUENCE DESCRIPTION: SEQ ID NO:34:

GATCTTCAGG CGTTGACGAC AACCCCG      27

(2) INFORMATION FOR SEQ ID NO:35:

(i) SEQUENCE CHARACTERISTICS:
    (A) LENGTH: 50
    (B) TYPE: nucleic acid
    (C) STRANDEDNESS: single
    (D) TOPOLOGY: linear (ii) MOLECULE TYPE: Genomic DNA (iii) HYPOTHETICAL: yes (xi) SEQUENCE DESCRIPTION: SEQ ID NO:35:

GATCTCCTCC GGGAAGCCAC CAAGAACCAC CCATTTCCTC CCCATGTTTG      50

(2) INFORMATION FOR SEQ ID NO:36:

(i) SEQUENCE CHARACTERISTICS:
    (A) LENGTH: 75
    (B) TYPE: nucleic acid
    (C) STRANDEDNESS: single
    (D) TOPOLOGY: linear (ii) MOLECULE TYPE: Genomic DNA (iii) HYPOTHETICAL: yes (x i) SEQUENCE DESCRIPTION: SEQ ID NO:36:

GATCTAAGGC TCTGACGTCT CCCCCCGGAG GGCAGCTCAG CACCGGCTCG    50

GGCTAGGCCC TGACGTGTCC CCCTG    75

(2) INFORMATION FOR SEQ ID NO:37:

(i) SEQUENCE CHARACTERISTICS:
      (A) LENGTH: 27
      (B) TYPE: nucleic acid
      (C) STRANDEDNESS: single
      (D) TOPOLOGY: linear (i i) MOLECULE TYPE: Genomic DNA (i i i) HYPOTHETICAL: yes (x i) SEQUENCE DESCRIPTION: SEQ ID NO:37:

GATCTTCAGG CGTAAGGAGC AACCCCG    27

(2) INFORMATION FOR SEQ ID NO:38:

(i) SEQUENCE CHARACTERISTICS:
      (A) LENGTH: 4
      (B) TYPE: amino acid
      (D) TOPOLOGY: unknown to applicant (i i) MOLECULE TYPE: peptide (i i i) HYPOTHETICAL: yes (i x) FEATURE:
      (B) LOCATION: 2
      (D) OTHER INFORMATION: Xaa(2) is any amino acid (x i) SEQUENCE DESCRIPTION: SEQ ID NO:38:

Tyr Xaa Arg Phe
1

(2) INFORMATION FOR SEQ ID NO:39:

(i) SEQUENCE CHARACTERISTICS:
      (A) LENGTH: 4
      (B) TYPE: amino acid
      (D) TOPOLOGY: unknown to applicant (i i) MOLECULE TYPE: peptide (i i i) HYPOTHETICAL: yes (i x) FEATURE:
      (B) LOCATION: 2
      (D) OTHER INFORMATION: Xaa(2) is any amino acid (x i) SEQUENCE DESCRIPTION: SEQ ID NO:39:

Phe Xaa Arg Phe
1

(2) INFORMATION FOR SEQ ID NO:40:

(i) SEQUENCE CHARACTERISTICS:
      (A) LENGTH: 22
      (B) TYPE: nucleic acid
      (C) STRANDEDNESS: single
      (D) TOPOLOGY: linear (i i) MOLECULE TYPE: Genomic DNA (i i i) HYPOTHETICAL: yes (x i) SEQUENCE DESCRIPTION: SEQ ID NO:40:

GTGTTTGCTG ACGCAACCCC AC    22

(2) INFORMATION FOR SEQ ID NO:41:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: Genomic DNA (iii) HYPOTHETICAL: yes (xi) SEQUENCE DESCRIPTION: SEQ ID NO:41:

GATCTAAGGC TCTGACGTCT CCCCA    25

(2) INFORMATION FOR SEQ ID NO:42:

(i) SEQUENCE CHARACTERISTICS:
        (A) LENGTH: 25
        (B) TYPE: nucleic acid
        (C) STRANDEDNESS: single
        (D) TOPOLOGY: linear (ii) MOLECULE TYPE: Genomic DNA (iii) HYPOTHETICAL: yes (xi) SEQUENCE DESCRIPTION: SEQ ID NO:42:

GATCTAGGCC CTGACGTGTC CCCCA    25

(2) INFORMATION FOR SEQ ID NO:43:

(i) SEQUENCE CHARACTERISTICS:
        (A) LENGTH: 24
        (B) TYPE: nucleic acid
        (C) STRANDEDNESS: single
        (D) TOPOLOGY: linear (ii) MOLECULE TYPE: Genomic DNA (iii) HYPOTHETICAL: yes (xi) SEQUENCE DESCRIPTION: SEQ ID NO:43:

GATCTGGCGT TGACGACAAC CCCA    24

(2) INFORMATION FOR SEQ ID NO:44:

(i) SEQUENCE CHARACTERISTICS:
        (A) LENGTH: 74
        (B) TYPE: nucleic acid
        (C) STRANDEDNESS: single
        (D) TOPOLOGY: linear (ii) MOLECULE TYPE: Genomic DNA (iii) HYPOTHETICAL: yes (xi) SEQUENCE DESCRIPTION: SEQ ID NO:44:

GATCTAAGGC TCTGACGTCT CCCCCCGGAG GGCAGCTCAG CACCGGCTCG    50

GGCTAGGCCC TGACGTGTCC CCCA    74

(2) INFORMATION FOR SEQ ID NO:45:

(i) SEQUENCE CHARACTERISTICS:
        (A) LENGTH: 29
        (B) TYPE: nucleic acid
        (C) STRANDEDNESS: single
        (D) TOPOLOGY: linear (i i) MOLECULE TYPE: Genomic DNA (i i i) HYPOTHETICAL: yes (x i) SEQUENCE DESCRIPTION: SEQ ID NO:45:

GATCTCCACC AAGAACCACC CATTTCCTA  29

(2) INFORMATION FOR SEQ ID NO:46:

(i) SEQUENCE CHARACTERISTICS:
        (A) LENGTH: 23
        (B) TYPE: nucleic acid
        (C) STRANDEDNESS: single
        (D) TOPOLOGY: linear (i i) MOLECULE TYPE: Genomic DNA (i i i) HYPOTHETICAL: yes (x i) SEQUENCE DESCRIPTION: SEQ ID NO:46:

GATCTGCCCG TGACGTTTAC ACA  23

(2) INFORMATION FOR SEQ ID NO:47:

(i) SEQUENCE CHARACTERISTICS:
        (A) LENGTH: 33
        (B) TYPE: nucleic acid
        (C) STRANDEDNESS: single
        (D) TOPOLOGY: linear (i i) MOLECULE TYPE: Genomic DNA (i i i) HYPOTHETICAL: yes (x i) SEQUENCE DESCRIPTION: SEQ ID NO:47:

GATCTCAACG GCAGGGGAAT CTCCCTCTCC TTA  33

(2) INFORMATION FOR SEQ ID NO:48:

(i) SEQUENCE CHARACTERISTICS:
        (A) LENGTH: 10
        (B) TYPE: amino acid
        (D) TOPOLOGY: unknown to applicant (i i) MOLECULE TYPE: peptide (i i i) HYPOTHETICAL: yes (x i) SEQUENCE DESCRIPTION: SEQ ID NO:48:

Ser Phe His Ser Leu His Leu Leu Phe Glu
1               5                   10

(2) INFORMATION FOR SEQ ID NO:49:

(i) SEQUENCE CHARACTERISTICS:
        (A) LENGTH: 10
        (B) TYPE: amino acid
        (D) TOPOLOGY: unknown to applicant (i i) MOLECULE TYPE: peptide (i i i) HYPOTHETICAL: yes (x i) SEQUENCE DESCRIPTION: SEQ ID NO:49:

His Ser Leu His Leu Leu Phe Glu Glu Tyr
1               5                   10

(2) INFORMATION FOR SEQ ID NO:50:

(i) SEQUENCE CHARACTERISTICS:
(A) LENGTH: 10
(B) TYPE: amino acid
(D) TOPOLOGY: unknown to applicant (ii) MOLECULE TYPE: peptide (iii) HYPOTHETICAL: yes (xi) SEQUENCE DESCRIPTION: SEQ ID NO:50:

```
Leu His Leu Leu Phe Glu Glu Tyr Thr Asn
1               5                   10
```

(2) INFORMATION FOR SEQ ID NO:51:

(i) SEQUENCE CHARACTERISTICS:
(A) LENGTH: 10
(B) TYPE: amino acid
(D) TOPOLOGY: unknown to applicant (ii) MOLECULE TYPE: peptide (iii) HYPOTHETICAL: yes (xi) SEQUENCE DESCRIPTION: SEQ ID NO:51:

```
Leu Leu Phe Glu Glu Tyr Thr Asn Ile Pro
1               5                   10
```

(2) INFORMATION FOR SEQ ID NO:52:

(i) SEQUENCE CHARACTERISTICS:
(A) LENGTH: 10
(B) TYPE: amino acid
(D) TOPOLOGY: unknown to applicant (ii) MOLECULE TYPE: peptide (iii) HYPOTHETICAL: yes (xi) SEQUENCE DESCRIPTION: SEQ ID NO:52:

```
Glu Tyr Thr Asn Ile Pro Ile Ser Leu Leu
1               5                   10
```

(2) INFORMATION FOR SEQ ID NO:53:

(i) SEQUENCE CHARACTERISTICS:
(A) LENGTH: 10
(B) TYPE: amino acid
(D) TOPOLOGY: unknown to applicant (ii) MOLECULE TYPE: peptide (iii) HYPOTHETICAL: yes (xi) SEQUENCE DESCRIPTION: SEQ ID NO:53:

```
Ile Pro Ile Ser Leu Leu Phe Asn Glu Lys
1               5                   10
```

(2) INFORMATION FOR SEQ ID NO:54:

(i) SEQUENCE CHARACTERISTICS:
(A) LENGTH: 12
(B) TYPE: amino acid
(D) TOPOLOGY: unknown to applicant (ii) MOLECULE TYPE: peptide (iii) HYPOTHETICAL: yes (xi) SEQUENCE DESCRIPTION: SEQ ID NO:54:

```
Ser Phe His Ser Leu His Leu Leu Phe Glu Glu Glu
```

(2) INFORMATION FOR SEQ ID NO:55:

(i) SEQUENCE CHARACTERISTICS:
        (A) LENGTH: 14
        (B) TYPE: amino acid
        (D) TOPOLOGY: unknown to applicant (ii) MOLECULE TYPE: peptide (iii) HYPOTHETICAL: yes (xi) SEQUENCE DESCRIPTION: SEQ ID NO:55:

Glu Glu Gly Gly Ser Phe His Ser Leu His Leu Leu Phe Glu
1               5                   10

(2) INFORMATION FOR SEQ ID NO:56:

(i) SEQUENCE CHARACTERISTICS:
        (A) LENGTH: 16
        (B) TYPE: amino acid
        (D) TOPOLOGY: unknown to applicant (ii) MOLECULE TYPE: peptide (iii) HYPOTHETICAL: yes (xi) SEQUENCE DESCRIPTION: SEQ ID NO:56:

Glu Glu Gly Gly Ser Phe His Ser Leu His Leu Leu Phe Glu Glu
1               5                   10                  15
Glu (2) INFORMATION FOR SEQ ID NO:57:

(i) SEQUENCE CHARACTERISTICS:
        (A) LENGTH: 10
        (B) TYPE: amino acid
        (D) TOPOLOGY: unknown to applicant (ii) MOLECULE TYPE: peptide (iii) HYPOTHETICAL: yes (xi) SEQUENCE DESCRIPTION: SEQ ID NO:57:

Phe Leu Ser Glu Phe Leu His Ser His Leu
1               5                   10

PEPTIDE INHIBITORS OF TAX-DEPENDENT TRANSCRIPTION

This application is a continuation-in-part of U.S. Ser. No. 08/021,536, filed Feb. 23, 1993, now abandoned.

The present invention relates to modulation of gene expression at the level of transcription, preferably through modulation of protein-protein interactions that regulate transcription. This invention can be applied both to cells with genetic abnormalities or to cells infected with a virus.

BACKGROUND

The present invention relates to regulators of cellular gene transcription, particularly inhibitors of cellular gene transcription and in particular to inhibition of gene transcription in a viral host cell that is subject to regulation by proteins or factors that originate from a virus. This invention can be applied both to cells with genetic abnormalities or to cells infected with a virus.

An example of cells with a genetic defect is patients with homozygous familial hypocholesterolemia. These patients exhibit inordinately high levels of plasma cholesterol and LDLs that can lead to atherosclerosis. The molecular mechanism underlying this condition is that patients are unable to suppress the activity of HMG-CoA-reductase, the rate-limiting enzyme for cholesterol synthesis. This invention could down regulate transcription of the gene encoding HMG-CoA-reductase.

Examples of viral targets include the Human T-cell Leukemia Virus I (HTLV-I) and the Hepatitis B Virus (HBV). Both of these viruses contain transactivating proteins (Tax and pX respectively) that regulate transcription of their viral genomes and also several genes within the host cell genome. In the case of HTLV-I, regulation (activation) of gene expression by Tax can lead to the development of Adult T cell Leukemia (ATL) or a neuromuscular disorder HTLV-I associated myelopathy or tropical spastic paraparesis (HAM/TSP). Coinfection of HTLV-I in HIV patients can result in increased transcription of the HIV genome and may accelerate the development of AIDS. In the case of HBV, regulation (activation) of gene expression by pX can lead to the development of hepatocarcinoma.

Although a great deal of information about oncogenes, tumor suppressor genes, and growth factors has been amassed over the last decade, the underlying molecular mechanism resulting in uncontrolled cell proliferation is incompletely understood. For many viral and other oncogenic diseases there are either no or only highly toxic treatments available. To overcome these deficiencies, many researchers have been attempting to understand and/or regulate gene expression post transcriptionally by preventing the transcribed messenger RNA from being translated into protein. Approaches currently being used include antisense oligonucleotides, and ribozymes. Triple helices are another approach that has been suggested to prevent transcription. While technically sound these approaches suffer from the short half life and relatively low permeability to cells of highly charged oligonucleotides and also to the limitations in the kinds of chemistry that can be carried out. This invention proposes to regulate gene expression at the level of transcription (generation of messenger RNA). This will be accomplished by disruption of protein-protein interactions by peptides or peptide mimetics designed to specifically disrupt interactions important to transcription. The use of peptides offers a potential for greater specificity than the use of oligonucleotides (20 different amino acids versus 4 nucleotides) and greater potential for chemical modifications to increase half life and permeability. Additionally, targeting these inhibitors to proteins not normally present in the cell (i.e. viral proteins or mutant forms of normal cellular proteins) enhances the probability that the drug will not interfere with normal cellular function.

Human T-Cell Leukemia Virus-I and Tax

Human T-Cell Leukemia Virus-I (HTLV-I) is the etiologic agent of adult T-cell leukemia (Poiesz et al., (1980) Proc. Nat. Acad. Sci. USA 77:7415–7419), and is also associated with several diseases of the neurological and muscular systems including HTLV-I-associated myelopathy/tropical spastic paraparesis and polymyositis (Gessain et al., (1985) Lancet 11:407–410; Osame et al., (1986) Lancet 1:1031–1032). HTLV-I is a retrovirus, and thus an RNA genome is present in the virion. A virion enzyme, reverse transcriptase, creates a DNA copy of the viral genome, termed the provirus, which is then integrated into the chromosomal DNA of the host cell. The Long Terminal Repeat (LTR) contains the cis-acting regulatory sequences of the provirus. Proviral DNA is transcribed by host cell RNA Polymersae II (RNAP II) into viral mRNA and new genomic RNA.

The gag, pol, and env genes present in the viral genome encode core proteins, virion-associated enzymes (reverse transcriptase, integrase, protease), and envelope glycoproteins, respectively. In addition, the 3' end of the HTLV-I genome contains a long open reading frame initially referred to as "X region" because its function was originally unknown (Seiki et al., (1983) Proc. Nat. Acad. Sci. USA 80:3618–3622; Haseltine et al., (1984) Science 225:419–421). This X region is essential for viral replication (Chen et al., (1985) Science 229:54–58), and is capable of immortalizing primary T lymphocytes in the absence of other HTLV-I genes (Grassmann et al., (1989) Proc. Nat. Acad. Sci. USA 86:3351–3355). Two proteins encoded in this region, Tax and Rex, have been identified by immunoprecipitations using infected cells (Lee et al., (1984) Science 226:57–61; Slamon et al., (1984) 226:61–65). Rex is a 27 kDa nuclear protein that acts post transcriptionally to allow efficient translation of the unspliced or partially spliced intermediate viral mRNAs (Hidaka et al., (1988) EMBO J. 7(2):519–523). Tax is a 40 kDa nuclear protein that interacts with the host cell transcriptional machinery. Numerous co-transfection experiments have shown that the tax gene product (Tax) increases transcription from the proviral LTR (Cann et al., (1985) Nature (London) 318:571–574; Felber et al., (1985) Science 229:675–679; Sodroski et al., (1985) Science 228:1430–1434; Fugisawa et al., (1986) EMBO J. 5:713–718; Seiki et al., (1986) EMBO J. 5:561–565; Shimotohno et al., (1986) Proc. Nat. Acad. Sci. USA 83:8112–8116; Brady et al., (1987) J. Virol. 61:2175–2181) and a number of other promoters (Cross et al., (1987) Cell 49:47–56; Siekevitz et al., (1987) Proc. Nat. Acad. Sci. USA 84:5389–5393; Siekevitz et al., (1987) Science 238:1575–1578; Miyatake et al., (1988) Mol. Cell Biol. 8:5581–5587; Nagata et al., (1988) J. Virol. 63:3220–3226; Ruben et al., (1988) Science 241:89–92; Saito et al., (1988) J. Virol. 62:644–648; Green et al., (1989) Mol. Cell. Biol. 9:4731–4737; Nimer et al., (1989) Oncogene 4:671–676; Lilienbaum et al., (1990) J. Virol. 64:256–263). Additionally, Tax down regulates the expression of human β polymerase, a cellular enzyme involved in host cell DNA repair (Jeang et al., (1990) Science 247:1082–1084). Because several of the genes regulated by Tax are involved in control of cell growth or maintenance of DNA, it is thought that transcriptional regulation by Tax contributes to viral oncogenesis. The Tax protein alone is sufficient for transactivation of the HTLV-I LTR and does not require Rex or any other viral gene products (Seiki et al., (1986) EMBO J. 5:561–565).

Some retroviruses transform cells by a promoter insertion mechanism, where a population of transformed cells is selected for by increased transcription of a cellular proto-oncogene. For example, Avian Leukemia Virus (ALV) is often found to be integrated at a specific region in transformed cells, where it activates transcription of the proto-oncogene myc. However, analysis of HTLV-I transformed lymphocytes from different individuals does not reveal a common site of integration of the provirus (Seiki et al., (1984) Nature 309(5969):640–642). This suggests that a protein encoded within the virus itself might be directly responsible for the oncogenicity of HTLV-I. Indeed, studies with transgenic mice showed this to be the case. The viral gene Tax elicits a variety of pathological changes in transgenic mice (Hinrichs et al., (1987) Science 237:1340–1343; Nerenberg et al., (1987) Science 237:1324–1329; Green et al., (1989) Mol. Cell. Biol. 9:4731–4737; Green et al., (1989) Nature (London) 341(6237):72–74; Nerenberg, (1990) Curr. Topics Microbiol. Immun. 160:121–128; Weiss and Schulz, (1990) Cancer Cells 2:281–283; Nerenberg et al., (1991) J. Virol. 65(6):3349–3353) and contributes to the transformation of cultured cells (Grassmann et al., (1989) Proc. Nat. Acad. Sci. USA 86:3351–3355; Pozzatti et al., (1990) Mol. Cell. Biol. 10(1):413–417; Tanaka et al., (1990) Proc. Nat. Acad. Sci. USA 87(3):1071–1075; Weiss and Schulz, (1990) Cancer Cells 2:281–283). Unlike the oncogenes of other RNA tumor viruses, tax has no known homology to cellular sequences (Chen et al., (1983) Nature (London) 305:502–505; Seiki et al., (1983) Proc. Nat. Acad. Sci. USA 80:3618–3622; Matthews and Anderson (1992) unpublished).

Eukaryotic promoters and enhancers

Before proposing the design, synthesis and screening of inhibitors of Tax transactivation in detail, it is useful to present an overview of the present state of understanding of the cellular transcriptional machinery. Regulation of RNAP II transcription can be influenced by distinct sequence elements present in the DNA both upstream and downstream from the site of transcription initiation. The TATA element, an AT rich region located around −28 from the RNA start site has a consensus sequence TATAAA and is common to many RNAP II promoters (reviewed in Breathnach and Chambon, (1981) Annual Rev. Biochem. 50:349–383). When present, the TATA element sets the position and direction of transcription. Although there are some promoters that do not contain an apparent TATA element, these promoters apparently use the same transcription initiation factors as TATA box containing promoters (Saltzmann and Weinmann, (1989) FASEB 3:1723–1733). In addition to the TATA element, other short, discrete DNA sequence elements contribute to the frequency of initiation by RNAP II. When these sequence elements are found immediately upstream of the transcriptional start site they are usually referred to as promoter elements. When these sequence elements are located at a large distance from the start site, they are usually referred to as enhancer elements.

Purified RNAP II will not accurately initiate transcription in vitro. Accurate initiation can be observed in whole cell or nuclear extracts (Well et al., (1979) Cell 18:469–484; Manely et al., (1980) Proc. Nat. Acad. Sci. USA 77:3855–3859), and can be reconstituted with partially purified fractions (Dignam et al., (1983) Meth. Enzymol. 104:582–598). At least seven general transcription factors, TFIIA, -IIB, -IID, -IIE, -IIF, -IIH, and -IIJ are thought to be required for recognition of simple promoters (Matsui et al., (1980) J. Biol. Chem. 255:11992–11996; Samuels et al., (1982) J. Biol. Chem. 257:14419–14427; Dignam et al., (1983) Meth. Enzymol. 104:582–598; Sawadago and Roeder, (1985) Proc. Nat. Acad. Sci. USA 82:4394–4398; Cortes et al., (1992) Mol. Cell. Biol. 12:413–421; Flores et al., (1992) J. Biol. Chem. 267:1–8). The general transcription factors have been purified from HeLa cell extracts, Drosophila (Kadonaga and Tjian, (1986) Proc. Nat. Acad. Sci. USA 16:5889–5893), yeast, and calf thymus, and cDNA clones of human TFIIB, TFIIE, TFIIF, and the DNA binding polypeptide of TFIID have been isolated.

In addition to the general transcription factors, which are required for transcription of all RNAP II promoters, there are promoter specific factors that interact with specific DNA sequence elements present in promoters and enhancers. Proteins that bind these elements were initially proposed to function in the control of transcription in the simplest terms by activating or repressing RNAP II function when bound at the promoter. As many of these factors were cloned and further characterized it became clear that their role in transcriptional control was complex. Many have a modular structure, containing discrete DNA binding domains and other domains required for transcriptional activation (reviewed in Johnson and McKnight, (1989) Annual Rev. Biochem. 58:799–839; Mitchell and Tjian, (1989) Science 245:371–378).

Recently it has been shown that the DNA binding protein cloned from the general factor TFIID is not sufficient to substitute for the purified TFIID fraction in reconstituted systems. Thus the possibility of a new class of transcription factors that may act as adaptors or mediators between general transcription factors and promoter specific factors was proposed (Kelleher et al., (1990) Cell 61:1209–1215; Dynlacht et al., (1991) Cell 66:563–576). Adaptor proteins that associate with TBP (TATA binding protein of TFIID) are referred to as TAF's (TBP associated factors).

Architecture of the HTLV-I promoter

The HTLV-I transcriptional control region extends over 300 bp and has a structure typical of a promoter transcribed by RNAP II. Sequences proximal to the start site include a TATA element, and region designated as Site 4 where at least three different factors bind (Nyborg et al., (1988) Proc. Nat. Acad. Sci. USA 85:1457–1461; Nyborg et al., (1990) J. Biol. Chem. 265:8230–8236). The Tax responsive elements (TxREs) in the HTLV-I LTR were determined by genetic and deletion analysis. These experiments identified a 21 bp sequence, imperfectly repeated 3 times in the HTLV-I promoter, that can mediate Tax transactivation (Shimotohno et al., (1986) Proc. Nat. Acad. Sci. USA 83:8112–8116; Brady et al., (1987) J. Virol. 61:2175–2181; Jeang et al., (1988) J. Virol. 62:4499–4509; Fujisawa et al., (1989) J. Virol. 63:3234–3239; Giam and Xu, (1989) J. Biol. Chem. 264:15236–15241; Montagne et al., (1990) EMBO J. 9:957–964). Although not identical, each 21 bp repeat TxRE will support transactivation when inserted in an appropriate promoter context (Jeang et al., (1988) Proc. Nat. Acad. Sci. USA 85:8291–8295; Fujisawa et al., (1989) J. Virol. 65(8):4525–4528; Giam and Xu, (1989) J. Biol. Chem. 264:15236–15241; Montagne et al., (1990) EMBO J. 9:957–964). A different element, Site 2a, between the second and third 21 bp repeats, can increase the response to Tax when in the context of at least one 21 bp repeat TxRE (Brady et al., (1987) J. Virol. 61:2175–2181; Marriott et al., (1990) Mol. Cell. Biol. 10:4192–4201; Marriott et al., (1989) Mol. Cell. Biol. 9:4152–4160).

The mechanism of interaction between these elements and Tax remains incompletely understood. Tax-mediated transactivation of the HTLV-I LTR does not require the synthesis of new host cell proteins (Jeang et al., (1988) Proc. Nat. Acad. Sci. USA 85:8291–8295; Giam and Xu, (1989) J. Biol. Chem. 264:15236–15241). A comparison of nuclear extracts from HTLV-I transformed T lymphocytes that do and do not express Tax shows that none of the observed features of the DNase I footprint pattern correlate directly with the presence of Tax in the extract (Altman et al., (1988) J. Virol. 62:1339–1346; Nyborg et al., (1988) Proc. Nat. Acad. Sci. USA 85:1457–1461). These results suggest that the primary recognition of promoter elements in the LTR involves specific interactions with preexisting host cell proteins and that Tax influences the activity of one or more of these proteins. For example, Tax might modify a host cell protein in a manner that alters its ability to bind DNA or to be recognized by the general transcriptional machinery. Alternatively, Tax might bind indirectly to the promoter via host cell proteins, perhaps serving as an adaptor, or mediator, of the interactions between transcription factors bound at different sites.

Several experiments suggest that localization of Tax at the promoter may be important for its activity. Tax was template associated in in vitro transcription reactions performed with nuclear extracts from HTLV-I infected cells (Matthews, 1992 Ph.D. thesis, University of Colorado, Boulder, Colo.). A GAL4-Tax fusion protein, but not Tax alone, transactivates constructs containing GAL4 binding sites (Fujii et al., (1991) Oncogene 6:2349–2352; Fujisawa et al., (1991) J. Virol. 65(8):4525–4528). Tax has been shown to bind indirectly to the HTLV-I promoter via a host cell factor that binds between the second and third 21 bp repeat TxREs (Marriott et al., (1989) Mol. Cell. Biol. 10:4192–4201). The relevance of this result remains unclear since the recognition site for this host cell factor is not essential for Tax mediated transactivation. The different mechanisms for Tax transactivation are not mutually exclusive. For example, Tax might induce an essential modification only when Tax and the cellular factor are associated in a complex at the promoter.

Tax transactivates several viral and cellular promoters in addition to the HTLV-I LTR. Most of these promoters do not appear to have sequences homologous to the 21 bp repeat TxRE found in HTLV-I LTR (Cross et al., (1987) Cell 49:47–56; Siekevitz et al., (1987); Siekevitz et al., (1987) Science 238:1575–1578; Nagata et al., (1988) J. Virol. 63:3220–3226; Ruben et al., (1989) New Biol. 1(3):275–283; Ruben et al., (1988) Science 241:89–92; Lilienbaum et al., (1990) J. Virol. 64:256–263). Interestingly, Tax transactivation of the IL-2Rα, IL-2, GM-CSF and HIV promoters appears to be mediated by the transcription factor NF-κB (Ballard et al., (1988) Science 241:1652–1655; Leung and Nabel, (1988) Nature (London) 333:776–778; Ruben et al., (1988) Science 241:89–92; Lindholm et al., (1991) New Biol. 2(11):1034–1043). Mutants of the Tax protein have been identified that are selectively defective for transactivation of the HTLV-I LTR or NF-κB responsive promoters, suggesting that the mechanisms by which Tax transactivates the HTLV-I LTR and NF-κB responsive promoters may be different (Ruben et al., (1989) New Biol. 1(3):275–284; Smith and Green, (1991) Genes Dev. 4:1875–1885). Alternatively, different domains on Tax could be required for Tax to be recruited to promoters containing ATF/CREB sites and NF-κB sites, while the activator domain of Tax may be the same for both promoters.

Cellular Proteins involved in HTLV-I gene regulation

The region of the LTR containing the 21 bp repeats functions as a Tax-dependent enhancer to stimulate transcription in a position and orientation dependent manner in vivo (Paskalis et al., (1986) Proc. Nat. Acad. Sci. USA 83:6558–6562; Brady et al., (1987) J. Virol. 61:2175–2181). Tax-mediated activation of in vitro transcription was also strongly dependent on this sequence (Matthews et. al., (1992) Mol. Cell. Biol. 12:1986–1996). All three HTLV-I 21 bp repeat TxREs contain a TGACG core sequence that also occurs in the E1a-activated early genes of human adenoviruses (Lee et al., (1987) Proc. Nat. Acad. Sci. USA 84:8355–8459) and in the cAMP response element (CRE) (Montminy et al., (1986) Proc. Nat. Acad. Sci. USA 83:6682–6686). The 21 bp repeats of HTLV-I direct cAMP-dependent transcription (Jeang et al., (1988) J. Virol. 63:4499–4509; Giam and Xu, (1989) J. Biol. Chem 264:15236–15241; Poteat et al., (1989) J. Virol. 64:63:1604–1611; Tan et al., (1989) J. Virol. 63:3761–3765); however, an element containing the 8 bp dyad-symmetric consensus CRE, TGACGTCA, is not Tax responsive (Fujisawa et al., (1989) J. Virol. 63:3234–3239). Moreover, HTLV-I expression is superinduced by cAMP in the presence of Tax (Poteat et al., (1989) J. Virol. 63:1604–1611). Together, these data suggest that although a similar sequence is recognized by transcription factors concerned with the cAMP response and Tax transactivation, these two pathways of induction are independent. Some proteins known to bind the CRE and the TxRE are part of a class of leucine zipper proteins. Members of this class contain a conserved leucine heptad repeat involved in dimerization, and a basic domain involved in DNA binding (Landschulz et al., (1988) Science 240:1759–1764). Leucine zipper proteins can bind to DNA in a number of homodimeric and heterodimeric combinations. Unlike the palindromic CRE, the TxRE is asymmetric and may favor binding of different combinations of these proteins.

A number of cellular proteins that bind the HTLV-I 21 bp repeat TxRE have been identified. Four proteins, TREB5, TREB7, TREB36, and TaxREB67 (with molecular weights 29, 55, 29, and 52 kDa respectively) were identified by screening cDNA libraries for expression of proteins that bind a 21 bp repeat TxRE oligonucleotide (Yoshimura et al., (1990) EMBO J. 9:2537–2524; Tsujimoto et al., (1991) J. Virol. 65(3):1420–1426). Several of these proteins are related to or identical to transcription factors that have been previously identified as binding to other promoters. TREB7 is identical to the CRE-BP1, and differs by 2 amino acids from ATF-2 (Hai et al., (1989) Genes Dev. 3:2083–2090; Maekawa et al., (1989) Oncogene 6(4):627–632; Yoshimura et al., (1990) EMBO J. 9:2537–2544). TREB36 is identical to ATF-1 and related to rat CREB (Gonzalez et al., (1989) Nature (London) 337:749–752; Hai et al., (1989) Genes Dev.; Yoshimura et al., (1990) EMBO J. 9:2537–2544); TaxREB67 is identical to ATF-4 (Hai et al., (1989) Genes Dev.3:2083–2090; Tsujimoto et al., (1991) J. Virol. 65(3):1420–1426).

Other 21 bp repeat TxRE-binding proteins have been identified using DNA affinity chromatography. TREB-1, a group of polypeptides with molecular weights in the 35–43 kDa range, has been purified from HeLa cell extracts (Tan et al., (1989) Mol. Cell. Biol. 9:1733–1745). HEF-IT, a group of polypeptides with molecular weights 41–43 kDa and 59 kDa, has been purified from lymphocyte extracts (Nyborg and Dynan, (1990) J. Biol. Chem. 265:8230–8236). These polypeptides were shown recently to be CREB and ATF2, respectively (Franklin et al., (1993) submitted to J. Biol. Chem.). Lymphocyte polypeptides with molecular weights 32, 36–42, 50 and 110 kDa were identified as binding the 21 bp repeat TxRE by DNA affinity chromatography, glycerol gradient sedimentation, and UV-crosslinking experiments (Beimling and Moelling, (1990) Oncogene 5:361–368). Beimling and Moelling ((1992) Oncogene 7:257–262) later demonstrated the 42 kDa polypeptide was identical to CREB. Although the preparations in these reports are not identical, they may have several polypeptides in common. Less well characterized host cell factors, some of which may be identical to those identified by screening cDNA libraries or by DNA affinity chromatography, have been identified by electrophoretic mobility shift assays and UV-crosslinking, including HEF-IB, TREB-2, TREB-3, HEB1, HEB2, PKAF, NF-21, and unnamed 110, 120, 180 kDa polypeptides (Jeang et al., (1988) J. Virol. 62:4499–4509; Park et al., (1988) Oncogene 3:275–279; Montagne et al., (1990) EMBO J. 9:957–964; Nyborg and Dynan, (1990) J. Biol. Chem. 265:8230–8236; Poteat et al., (1990) J. Virol. 64:1264–1270.

Other proteins bind to the HTLV-I promoter at sequences outside the 21 bp repeat TxRE, including AP-2, Sp1, NF-1, HEF-4C, TIF-1, and Ets1 (Marriott et al., (1990) Mol. Cell. Biol. 9:4152–4160; Nyborg et al., (1990) J. Biol. Chem. 265:8230–8236; Gitlin et al., (1991) J. Virol. 65(10):5513–5523). Identifying which of these proteins, if any, mediate the Tax response is difficult since such a large number of proteins can interact with the HTLV-I promoter. For example, Jun/AP-1 appears to bind the 21 bp repeat TxRE, but evidently is not essential for Tax mediated transactivation (Jeang et al., (1991) Virology 181(1):218–227). TREB7/CRE-BP1 was recently shown to mediate transactivation by the adenovirus transactivator E1a, but not by Tax (Maekawa et al., (1991) Oncogene 6(4):627–632). When ATF1, ATF2, and CREB were tested for the ability to mediate activation by E1a, cAMP, and Tax, no Tax response was detected (Flint and Jones, (1991) Oncogene 6:2019–2026).

Mechanism of Tax and other viral transactivators

Two groups have reported a stable association of Tax with host cell protein-DNA complexes in electrophoretic mobility shift assay (EMSA) or DNA precipitation assays (Beraud et al., (1991) EMBO J. 10:3795–3803; Zhao and Giam, (1991) Proc. Nat. Acad. Sci. USA 88:11445–11449). Those results are in contrast to the results of Matthews et al., (1992) Mol. Cell. Biol. 12:1986–1996 AND Franklin et al., (1993) J. Biol. Chem. 268:21225–21231, who showed Tax increased binding of cellular factors to HTLV-I DNA, but suggested that Tax was not present in the protein-DNA complex. The experiments showing a stable association of Tax in the protein-DNA complex differed in design from those that did not. Tax was not present in the complex when highly purified preparations of lymphocyte transcription factors specific for the 21 bp repeat were tested with a single 21 bp repeat oligonucleotide (Matthews et al., (1992) Mol. Cell. Biol. 12:1986–1996). Tax was present in complexes when the DNA probes used contained multiple TxREs, and crude protein fractions were used(Beraud et al., (1991) EMBO J. 10:3795–3803; Zhao and Giam, (1991) Proc. Nat. Acad. Sci. USA 88:11445–11449). It is possible that the less purified fractions could have contained cofactors required for binding or that Tax requires more than one TxRE to stably associate. Taken together, these experiments suggest that Tax-TxRE binding protein association occurs, but either is weak or sensitive to assay conditions and so not always detectable.

The mechanism by which Tax increases binding of cellular proteins to the TxRE is unknown. However, based on recent studies with other transcription factors, there are several interesting possibilities. It may be that transient interaction with Tax induces a long lasting non-covalent change in the state of TxRE binding proteins. For example, Tax could dissociate an inhibitor molecule from a TxRE binding protein, allowing it to adopt a conformation more favorable to DNA binding. Recently, it was reported that the adenovirus transactivator protein, E1a, can dissociate transcription factor E2F from a complex with the tumor suppressor protein Rb (Bagchi et al., (1991) Cell 65(6):1063–1072; Chellappan et al., (1991) Cell 65:1053–1061; Chittenden et al., (1991) Cell 65(6):1073–1082. The adenovirus E2 promoter, which is transactivated by E1a, contains E2F binding sites.

Alternatively, Tax may covalently modify TxRE binding proteins, increasing their affinity for DNA. The hepatitis B Virus (HBV) viral transactivator protein, X, has a protein kinase activity and has been shown to influence binding of transcription factors to the HBV promoter (MaGuire et al., (1991) Science 252:842–844). Addition of ATP had no effect on protein-DNA complexes formed in the presence of Tax (Matthews et al., (1992) Mol. Cell. Biol. 12:1986–1996) so it is unlikely that Tax directly alters the phosphorylation state of TxRE binding proteins. Several observations suggest that Tax could interact with TxRE binding proteins through regulation of the redox state of cysteine residues in those proteins. Monomeric Tax, but not Tax aggregated through intermolecular disulfide bonds, activated in vitro transcription (Matthews et al., 1992 Mol. Cell. Biol. 12:1986–1996). Several members of the ATF/CREB family of protein known to bind the TxRE, have a conserved cysteine residue in their conserved basic domain. While the position of this cysteine is conserved in aligned sequences, it varies in numerical amino acid position from protein to protein (Cys 154 in fos and Cys 272 in jun). A number of members of the Fos/Jun transcription factor family also have a conserved cysteine in their basic domain. Oxidation of this residue inactivates DNA binding activity, and incubation with reducing agent, or with an identified nuclear factor Ref-1 stimulates DNA binding (Xanthoudakis and Curran (1992) EMBO 11:653–665). When the conserved cysteine in Fos and Jun is changed to serine, binding activity is no longer inhibited by a sulfhydryl oxidizing agent. Interestingly, vJun contains a cysteine to serine mutation that may allow the vJun oncoprotein to escape cellular controls on DNA binding. Similarly, members of the C/EBP family contain a conserved cysteine or serine residue. When exposed to reducing agents, these proteins form new homo and heteromeric complexes in varying proportions (Bannister et al., (1991) Oncogene 6:1243–1250; Williams et al., (1991) Genes Dev. 5:1553–1567). Perhaps Tax selects which member of these leucine zipper family proteins are assembled into transcription complexes at the HTLV-I promoter. Tax could stabilize TxRE binding proteins in their existing redox state, or alternatively, Tax could selectively oxidize or reduce some of the many TxRE binding proteins, changing the available pool of active DNA-binding proteins.

Alternatively, or in addition to modification of TxRE binding proteins, Tax may have other biochemical activities important for transcription. Several lines of evidence suggest that Tax interacts with at least one site near the promoter in addition to the known 21 bp repeat TxREs and Site 2a. A GAL4-Tax fusion protein has been shown to activate transcription in a promoter lacking all known TxREs (Fujisawa et al., (1991) J. Virol. 65(8):4525–4528), suggesting that Tax must have some additional target, perhaps one of the general transcription factors, for example, the TATA binding protein or one of its associated factors (TAF's). Consistent with this observation, two-fold activation of in vitro transcription by Tax has been observed with promoters unrelated to HTLV-I, including an Sp1 dependent promoter and the Adenovirus 2 major late promoter (Matthews et al., (1992) Mol. Cell. Biol. 12:1986–1996).

Tax might interact with both upstream factors bound at the TxREs and with other transcription factors, perhaps serving as a bridge, or adaptor, between proteins bound at different sites. Tax is one of several viral regulatory proteins that activate transcription without binding directly to DNA in a sequence specific manner. Some of the other viral proteins in this group have already been shown to interact with both promoter-specific and general transcription factors. For example, the adenovirus transactivating protein, E1a, interacts with the promoter-specific activators ATF-2 and AP-1/Jun and with the general transcription factor TFIID (Lillie and Green, (1989) Nature (London) 338:39–44; Liu and Green, (1990) Cell 61(7)1217–1224; Horikoshi et al., (1991) Proc. Nat. Acad. Sci. USA 88(12):5124–5128; Maekawa et al., (1991) Oncogene 6(4):627–632; MaGuire et al., (1991) Science 252:842–844). The herpes simplex virus transactivating protein, VP16, interacts with the promoter specific activator OTF1 and with the general transcription factors TFIIB and TFIID (Gerster and Roeder, (1988) Proc. Nat. Acad. Sci. USA 83:6347–6351; Stern et al., (1989); Stringer et al., (1990) Nature (London) 345(6278):783–786; Lin and Green, (1991) Cell 64:971–981). The hepatitis B virus transactivating protein, X, interacts with the promoter specific factors ATF-2 and CREB (MaGuire et al., (1991) Science 252:842–844). It is not known whether hepatitis X protein interacts with general transcription factors, but, as with other viral transactivating proteins, localization of the hepatitis X protein at the promoter is important for its activity (Gerster and Roeder, (1988) Proc. Nat. Acad. Sci. USA 83:6347–6351; Sadowski et al., (1988) Nature (London) 335(6190):563–564; Lillie and Green, (1989) Nature (London) 3328:39–44; Unger and Shaul, (1990) EMBO J. 9:2537–2524).

The different mechanisms presented for Tax-mediated transcription are not mutually exclusive. It is possible that Tax has a catalytic activity and selects the most potent sequence specific transcriptional activators to assemble at upstream sequences in the HTLV-I promoter, and also recruits or stabilizes functional transcription complexes through interactions with the general transcription factors.

For many viral and other oncogenic diseases there are either none or only highly toxic treatments available. To this end, an entire Biotech industry has been spawned on the basis of regulated transcription via antisense oligonucleotides, triple helix forms or ribozyme approaches. All of these are technically sound approaches but suffer from the short half life or relatively low permeability of cells to highly charged oligonucleotides and limitations to the kinds of chemistry that can be carried out.

The approach used in the present invention, as well as the invention itself, is novel in that it is based on protein-protein interactions or on complex protein-nucleic acid interactions. The present invention also has the advantages that: 1) it inhibits at the transcription level; 2) inhibition is specific because the target is a viral oncogene that has no cellular homolog; and 3) it is a peptide inhibitor of a protein-protein interaction.

SUMMARY OF THE INVENTION

The present invention relates to modulation of gene expression at the level of transcription, preferably through modulation of protein-protein interactions that regulate transcription. This invention can be applied both to cells with genetic abnormalities or to cells infected with a virus. Preferably, at least one protein of the protein-protein interactions is a transactivating factor.

The present invention relates to regulators of cellular gene transcription, particularly inhibitors of cellular gene transcription and in particular to inhibition of gene transcription in a viral host cell that is subject to regulation by proteins or factors that originate from a virus.

An example of cells with a genetic defect is patients with homozygous familial hypocholesterolemia. These patients exhibit inordinately high levels of plasma cholesterol and LDLs that can lead to atherosclerosis. The molecular mechanism underlying this condition is that patients are unable to suppress the activity of HMG-CoA-reductase, the rate-limiting enzyme for cholesterol synthesis. This invention could down regulate transcription of the gene encoding HMG-CoA-reductase.

Examples of viral targets include the Human T-cell Leukemia Virus I (HTLV-I) and the Hepatitis B Virus (HBV). Both of these viruses contain transactivating proteins (Tax and pX respectively) that regulate transcription of their viral genomes and also several genes within the host cell genome. In the case of HTLV-I, regulation of gene expression by Tax can lead to the development of Adult T cell Leukemia (ATL) or a neuromuscular disorder HTLV-I associated myelopathy or tropical spastic paraparesis (HAM/TSP). Coinfection of HTLV-I in HIV patients can result in increased transcription of the HIV genome and may accelerate the development of AIDS. In the case of HBV, regulation of gene expression by pX can lead to the development of hepatocarcinoma.

Unless stated otherwise, transactivation for purposes of this invention is the interaction of a transactivating factor with a target DNA sequence of a host cell such that the level of transcription driven by the target sequence is altered. The transactivating factor may up regulate some genes and down regulate others. Transactivating factors for purposes of this invention mean biological factors, preferably a protein, that are not naturally occurring in the host cell. A non-naturally occurring biological factor is a protein or molecule that is not usually found in the cellular host during normal growth and division of the cellular host and such a non-naturally occurring biological factor can include a protein or molecule that is produced outside the cellular host and transported into the host cell or it can be a protein or molecule that is produced by the cellular host under unusual or stress conditions. Such unusual or stress conditions include introduction of foreign or non-naturally occurring genetic material into the cellular host or the expression or unmasking of a usually unexpressed or masked gene. Viral transactivation is the interaction of a biological factor provided by a virus, preferably a protein, with a target DNA sequence of the viral host such that the target DNA sequence is upregulated or down regulated. By up regulated, it is meant that the target DNA sequence that is the target of the transactivating factor directs transcription of the corresponding gene into complementary genetic material, preferably RNA, in a significantly larger amount in the presence of the transactivating molecule than in its absence. The increase in transcription in turn usually leads to increased translation and protein production. Significantly larger amounts of transcription in the presence of the transactivating factor is transcription of at least about 2 fold, preferably about 10, preferably about 20, more preferably about 50 times more complementary genetic material than in the absence of the transactivating factor. Alternatively, significantly larger amounts of transcription in the presence of the transactivating factor is protein production of at least about 2 times, preferably about 10 times, preferably at least about 20 to 40 times, more preferably at least about 100 times more protein production than in the absence of the transactivating protein. The presence of the transactivating factor Tax in an in vitro transcription reaction resulted in a 10–40 fold increase in mRNA synthesis (Matthews et al., Mol. Cell Biol., (1992) 12:1986–1996). In a transfection assay (measuring transcription indirectly through a reporter gene chloramphenicol acetyl tranferase CAT) three cell lines that produce transactivating protein Tax showed 74, 28, and 180 fold higher levels of CAT activity from a Tax-responsive target DNA (the HTLV-I promoter) than from a control DNA sequence (SV40 enhancerless early promoter) (Sodroski et al. (1984) Science 225:381–385). Preferably, the protein produced that is measured for an indication of increased transcription is a reporter protein that is easily detected, more preferably chloramphenicol acetyl transferase (CAT) or luciferase. By down regulated it is meant that the target DNA sequence that is the target of the viral transactivating factor regulates transcription of the target gene into mRNA in significantly less amount in the presence of the transactivating factor than in the absence of the transactivating factor. In a cotransfection assay, the transactivating factor Tax decreased protein production of a reporter gene linked to the promoter of the human B polymerase gene 36 fold compared to protein production in the absence of the transactivator (Jeang et al. (1990) Science 247:1082–1084).

The interaction of the transactivating factor with the target DNA need not be by way of any chemical bond and can be either direct or indirect. Transactivating factors might modify an auxiliary host cell protein in a manner that alters its ability to bind DNA or to be recognized by the transcriptional machinery. Alternatively, the transactivating factor could bind indirectly to the promoter via auxiliary host cell proteins serving as an adapter, or mediator, of the interactions between transcription factors bound at different sites. Auxiliary host cell proteins may include one or more sequence specific DNA binding proteins, general transcription factors or tumor suppressors. Transactivating factors might also decrease the amount of an auxiliary host cell protein by decreasing its protein synthesis, thereby decreasing the transcription of the target DNA sequence.

The inhibitors of transactivation that are the subject of the present invention therefore inhibit the interaction of a transactivating factor with a target DNA sequence and consequently prevent or significantly suppress the up regulation of transactivation. The preferred candidates for inhibitors are those molecules that block the binding of the transactivating factor to its target, whether the target be the target DNA sequence itself or an auxiliary host cell protein. More preferred inhibitors are those that block the binding site on the transactivating factor or the target. Blocking the binding site on the transactivating factor or the target can be accomplished by an inhibitor that binds the binding site of the transactivating factor or the target but does not result in up regulation of the target DNA sequence to the same degree as when the transactivating factor and the target DNA sequence are not in the presence of the inhibitor. An even more preferred inhibitor, therefore, is a molecule that simulates or mimics the binding characteristics of the transactivating factor or the target without mimicking, simulating or producing the biological effect that results in significantly larger amounts of transcription of the target DNA sequence. The most preferred molecule is a peptide that is similar to a fragment of the naturally occurring transactivating factor or target and that contains a significant portion of the binding site of either. Such peptides can include peptide mimetics, which include peptides with modified amino acids or modified peptide linkages such that peptide degradation is decreased. A significant portion of the binding site is a portion of the binding site large enough to allow detectable specific binding of the fragment from the transactivating factor or target to the corresponding target or transactivating factor, respectively. A significant portion of the binding site can be any chemical structure that imitates the binding site of the natural protein, but preferably the significant portion of the binding site is a peptide. Detectable specific binding is binding that is more than non-specific binding between biological molecules wherein the magnitude of the binding that cannot be attributed to non-specific binding is larger than the error bar for the binding measurement technique utilized. Preferably, specific binding will be demonstrated by inhibition such that inhibition constants (Ki's) will be less than 100 µM, preferably less than 10 µM, more preferably less than 1 µM, most preferably less than 100 nM.

Therefore, it can be seen that a candidate inhibitor can be derived from either the transactivating protein or an auxiliary host cell target protein to which it binds since either type of inhibitor would compete with the transactivating protein or target and inhibit the usual binding of the transactivating protein to the target and hence inhibit transactivation and protein production. The preferred inhibitor would be one that is derived from the auxiliary host cell target protein and which binds to the transactivating factor and no other host cell protein. Such an inhibitor would preferably inhibit transactivation without blocking normal transcription. Such an inhibitor would not totally inhibit cellular transcription but would only inhibit the up regulation in transcription due to the transactivation. Although the preferred inhibitor is one that is derived from the auxiliary host cell target protein, it is possible that for a particular transactivation system the inhibitor that is derived from the transactivating protein will be obtained first and then used to probe the transcription mechanism in a particular instance to subsequently obtain the inhibitor that is derived from the auxiliary host cell target protein.

Another aspect of the present invention is conjugates or fusion products of the inhibitors and internalization molecules that will enhance the internalization of the inhibitors into the host cell and nucleus. A related aspect of the present invention relates to methods that increase internalization of the inhibitors of the present invention.

The present invention is also drawn to pharmaceutical compositions that can be used to alleviate or prevent the manifestation of disease states that are the result of unregulated DNA transcription as a result of transactivation.

One aspect of the present invention is the use of the inhibitors of the present invention in regulated gene therapy to achieve long term drug delivery of the inhibitors of the present invention.

Another aspect of the present invention is a method of treating diseases that are caused or exacerbated by the presence of transactivating factors.

DETAILED DESCRIPTION OF THE INVENTION

The present invention relates to modulation of gene expression at the level of transcription, preferably through modulation of protein-protein interactions that regulate transcription. This invention can be applied both to cells with genetic abnormalities or to cells infected with a virus. The present invention relates to regulators of cellular gene transcription, particularly inhibitors of cellular gene transcription and in particular to inhibition of gene transcription in a viral host cell that is subject to regulation by proteins or factors that originate from a virus. The present invention preferably relates to inhibitors of viral transactivation, preferably inhibitors of viral transactivation mediated by the HTLV-I Tax protein or the Hepatitis B Protein X.

Obtaining Candidate Inhibitor Molecules

Candidate inhibitors of the present invention can therefore be obtained by a number of methods. They can be obtained, for example, by screening phage peptide display libraries that are either available or are custom made. A completely nonpredictive screen for candidate peptide inhibitors is to screen phage displayed peptides using affinity chromatography for the ability to bind to transactivating proteins, preferably such as Tax, then screen the transactivating protein-binding peptides for the ability to inhibit transcription. The phage display library can be constructed for example in filamentous phage such as fd-tet (Scott and Smith, (1990) Science 249:386-390; ibid, Methods in Enzymology, Vol. 217; Cwirla et al., (1990) Proc. Nat. Acad. Sci. USA, 87:6378-6382), or M13 (Devlin et al., (1990) Science 249:404-406; O'Neil et al., (1992) Proteins 14:509-515) and candidate peptides can be expressed as membrane protein gpIII fusion proteins.

There are methods known in the art for screening expression libraries with antibodies. A compilation of these methods is presented in *Current Protocols in Molecular Biology* (ed. Ausubel et. al., (1991) John Wiley & Sons, New York). Generally, the library is titered with an *E. coli* strain (LE392 is often used [*Current Protocols in Molecular Biology* (ed. Ausubel et. al., (1991) John Wiley & Sons, New York]; as is K91 (Scott and Smith, (1990) Science 249:386-390; O'Neil et al., (1992) Proteins 14:509-515; Cwirla et al., (1990) Proc. Nat. Acad. Sci. USA, 87:6378-6382) and plated. The proteins produced during phage growth and cell lysis are transferred to a nitrocellulose filter. The filter is blocked with nonfat milk to prevent nonspecific protein-protein interactions and is probed with antibody. We have modified this method and probe the nitrocellulose filters with the purified transactivating protein (e.g., Tax). Transactivating protein (e.g., Tax) binding can be detected directly by using radiolabelled transactivating protein (e.g., Tax) to probe the filters and autoradiography to visualize positive phage. Alternatively, filters can be probed with unlabelled transactivating protein (e.g., Tax), followed by an antibody against the transactivating protein (e.g., Tax). The candidate peptide inhibitor-transactivating protein-antibody complex (preferably Tax) can be detected by incubation with radiolabelled Protein A or incubation with an enzyme conjugated secondary antibody. An alternative method for identifying peptides which bind to Tax is biopanning a phage display library of random peptides (peptide fusion phage). In this procedure the target protein (e.g. Tax) can be treated with a biotinylating agent (commercially available from Pierce or Promega) under conditions where preferably 1-6 biotin moieties are introduced per protein molecule, (more preferably 1-3/protein molecule, most preferably 1/protein molecule). The biotinylated protein can then be bound essentially irreversibly to a solid support (e.g. a polystyrene dish) that is coated with streptavidin. After blocking nonspecific protein adsorption sites with bovine serum albumin, the streptavidin-coated plates can treated with the biotinylated protein (e.g. biotinylated Tax). The plates can then be blocked with biotin and rinsed. The phage library can be added to the plates which are now coated with the target protein bound to streptavidin via the biotin linker. Peptide fusion phage displaying random peptides which do not bind Tax are washed away under non-denaturing conditions. After the non-binding fusion phage are washed away, those fusion phage which bind Tax can be eluted with pH 2.2 buffer. The phage recovered in the elution step can be amplified and subjected to further rounds of biopanning.

Once phage displaying transactivating protein (e.g., Tax) binding peptides are identified, the phage DNA can be isolated, sequenced, and the sequence of the peptide determined. The peptide can then be chemically synthesized and screened for the ability to inhibit transcription. The sequence of the peptide that binds to the transactivating protein (e.g., Tax) can be used to search protein sequence data bases (e.g., Swiss Protein Bank). The sequence of the peptide may match a portion of the sequence of the transcription factor such as Tax interacts with. This information may be useful in optimizing the binding of the peptide to the transactivating protein (e.g., Tax).

In addition to phage libraries of peptides, phage expression libraries prepared from the cDNA of lymphocytes can also be screened for proteins that bind to transactivating proteins (e.g., Tax) using the above methods. After these proteins are identified, the portion of them that binds to the transactivating protein (e.g., Tax) can be identified as discussed in a later section. Human lymphocyte cDNA libraries are commercially available (for example, CLONTECH Laboratories, Inc., Palo Alto, Calif.) and techniques for preparing custom cDNA libraries are widely understood (*Current Protocols in Molecular Biology* ed. Ausubel et. al., (1991), John Wiley & Sons, New York).

Those phages that are determined to have candidate inhibitors can then be analyzed to determine the protein and eventually the genetic material coding for such protein that can be used to produce a candidate inhibitor.

Another method of obtaining the candidate inhibitors of the present invention involve obtaining protein fragments and screening them for their ability to inhibit transactivation. Such protein fragments can be obtained by synthesizing random protein fragments by known techniques (*Synthetic Peptides: A User's Guide*, G. A. Grant (ed.) (1992), W. H. Freeman & Co., New York; Jung and Beck-Sickinger, (1992) Angew. Chem. Int'l Ed. Eng. 31:367-484). Preferably such random protein fragments are sufficiently long to contain a complete binding epitope, preferably from about 4 to about 20 amino acids in length, more preferably from about 5 to about 12 amino acids in length, most preferably from about 6 to about 8 amino acids in length. Random hexamers for various proteins have been produced (Houghten et al., (1991) Nature 354:84-86), and a method for the synthesis of equimolar random peptide mixtures has also been described (Zuckermann et al., (1992) Proc. Nat. Acad. Sci. USA 89:4505-4509).

Finding an inhibitory peptide may require testing a very large number of different peptides. A large 2-dimensional array of different peptides can be generated on a solid substrate using photolithography techniques, and the target binding ability, preferably Tax binding ability, of the different sequences rapidly determined by which positions in the array bind the target such as Tax. The methods for utilizing this technique have been described (Fodor et al., Science (1991) 251:767-773), and consist of the following procedure. A glass substrate is coated with a chemical containing a free amino group. The amino groups are derivatized with nitroveratryloxycarbonyl (NVOC), a photoremovable protecting group. Small regions of the substrate are deprotected by exposure to light and then the entire substrate exposed to the activated ester of a particular NVOC-amino acid (NVOC protected amino group). The activated amino acid will react with the substrate only in the deprotected region, giving a spatially localized region of attachment of the amino acid to the substrate. Further cycles of deprotection and exposure to an NVOC-amino acid can attach additional residues. By choosing which NVOC-amino acid to add in any given cycle, and the pattern of the "photo-mask" (which determines the areas of the substrate that are exposed to light and deprotected), residues can be added in any desired order and position. This results in a 2-dimensional array of different peptides whose total number is limited by the size of the substrate and the resolution of the photo-mask. Fodor et al., have demonstrated 50,000 compounds/cm$^2$. High spatial resolution electron beam lithography has generated patterns at a density of $10^{10}$/cm$^2$ (Newman et al., (1987) J. Vac. Sci. Technol. B5:88) After synthesis of the array is completed, it can be exposed to fluorescently labelled target protein such as Tax and binding of specific peptides to the target protein such as Tax determined by which positions in the array are fluorescent. Peptides which have high binding affinity for a target protein such as Tax can be individually tested for their ability to inhibit the role of the target protein in transcriptional transactivation activity.

This method may have several advantages over other procedures for generating and testing large numbers of peptides. First, a very large number of different peptides can be generated in a small area and with modest amounts of reagents. Second, the peptides generated are not random and therefore may represent a more complete set of all possible peptide sequences of a given length than a method which generates random sequences. Third, once the array is constructed, target binding (such as Tax) can be rapidly assayed under many different conditions (concentration, pH, salt, etc.). Fourth, since all of the peptides generated are assayed for their binding affinity, it may be possible to glean additional information about factors affecting binding by comparing peptides with slightly different binding affinities. Finally, peptides can be constructed with D-amino acids, with modified side chains, or with other alterations not normally found in biological systems.

Another method of obtaining the candidate inhibitors of the present invention involves obtaining protein fragments that are not random fragments, but are fragments specifically designed to be duplicative of protein fragments that comprise a portion of a known protein. Preferably, the known protein will be one of two interacting proteins for which the candidate inhibitor is being obtained. More preferably, the known protein will be either a transactivating protein or an auxiliary host cell protein. More preferably, the known protein will be a viral transactivating protein or target, more preferably Tax or Hepatitis B protein X (HBV pX; Factor and Shaul, (1990) Oncogene 5:867–872) or their target, most preferably, the auxiliary host cell target protein for Tax or Hepatitis B. Such fragments can be produced by synthesizing portions of a known sequence (Schnorrenberg and Gerhardt, (1989) Tetrahedron 45:7759–64) or cleaving fragments from an isolated protein or subjecting the known protein to proteolysis.

Peptide synthesis is the preferred method of producing fragments specifically designed to be duplicative of protein fragments that comprise a portion of a known protein. In order to produce and screen the maximum number of possible binding epitopes, overlapping fragments can be synthesized such that the sum total of all the fragments essentially includes the known protein. However, each fragment shares a part of its amino acid sequence with one or more other fragments, preferably at the ends of the fragment. In this way, potential binding epitopes will occur in the central portion of at least one fragment. The design of the length of the fragment and the amount of overlap is important to obtaining a successful candidate inhibitor. A preferred maximum peptide length is less than about twenty amino acids because peptide synthesis yields can decrease when the peptide length exceeds twenty amino acids and because shorter peptides are easier to synthesize (Merrifield, (1986) Science 232:343–347; Kent, (1988)Ann. Rev. Biochem. 57:957–989; G. T. Young in *Chemical Synthesis and Sequencinclng of Peptides and Proteins*, T. Liu, A. Schechter, R. Heinrickson and P. Condliffe (eds.), Elsevier North Holland Inc., New York, 1981). A preferred minimum peptide length is about six amino acids since this is probably the smallest binding epitope that provide any specificity of binding. Binding epitopes of three amino acids have been recovered and published (RGD by O'Neil et al., (1992) Proteins 14:509–515, and HPQ by Devlin et al., (1990) Science 249:404–406). Scott and Smith, (1990) Science 24–9:386–390 and Houghten et al., (1991) Nature 354:84–86 have both made random hexamer libraries. Therefore, the preferred peptide fragment length is from about 6 amino acids to about 20 amino acids. Since most binding epitopes have six to eight amino acids, a preferred degree of overlap is from about 6 amino acids to about 10 amino acids. Therefore, fragments specifically designed to be duplicative of protein fragments that comprise a portion of a known protein can be synthesized that are from about 15 to about 20 amino acids in length with an overlap of from about 6 to about 8 amino acids. More preferably, the fragments will be about twenty amino acids long with about 8 amino add overlap.

Another way to design the fragments of a known protein would be to choose fragments based upon the hydrophilidty of the fragment. Fragments that are predominantly hydrophilic are more likely to be exposed to a polar solvent such as is found within the cell (as opposed to hydrophobic fragments which would tend to be folded into the interior of the folded protein) and thus more likely to contain a binding site. Another way to design the fragments of a known protein would be to choose fragments that contain proline since proline provides a sharp turn or "kink" in a protein. Proline is considered one of the most hydrophilic (exposed) residues and is usually found on protein surfaces. It does often result in "kinks" and these are often in turns (Rose et al., (1985) Adv. Protein Chem. 37:1o109) which are frequently sites for protein-biomolecule contacts (Janin and Chothia, (1990) J. Biol. Chem. 265:16027–16030). A sequence "flanked" by prolines could be an internal hydrophobic sequence, as well as an exposed loop. It is much more probable (based on analyses of positions of Pro residues found in protein crystal structures) that Pro residues will be found on exposed surfaces and thus we would want to synthesize peptide fragments that include Pro residues somewhere in the middle of the peptide Such proline containing fragments may be particularly significant in a protein such as Tax which contains 41 prolines or 12 percent of the total amino acid content.

A particularly preferred approach is to chemically synthesize a series of overlapping peptides spanning an entire transactivating protein, for example the entire Tax protein sequence (Seiki et al., (1985) Science 228:1532–1534). Each peptide will be about 20 amino acids in length and overlap with the previous peptide by about 8 amino acids.

The following is a list of preferred peptides to be synthesized beginning at the amino terminus wherein the accepted one letter designation for amino acids is used (I.D. Seq. Nos. 1 through 29, respectively).

MAHFPGFGQSLLFGYPVYVF
       FGYPVYVFGDCVQGDWCPIS
              QGDWCPISGGLCSARLHRHA
                     SARLHRHALLATCPEHQITW

CPEHQITWDPIDGRVIGSAL
       GRVIGSALQFLIPRLPSEPT
              PRLPSFPTQRTSKTLKVLTP
                     KTLKVLTPPITHTTPNIPPS

TTPNIPPSFLQAMRKYSPFR
       MRKYSPFRNGYMEPTLGQHL
              EPTLGQHLPTLSFPDPGLRP
                     FPDPGLRPQNLYTLWGGSVV

TLWGGSVVCMYLYQLSPPIT
       YQLSPPITWPLLPHVIFCHP
              PHVIFCHPGQLGAFLTNVPY
                     AFLTNVPYKRIEELLYKISL

ELLYKISLTTGALIILPEDC
       LIILPEDCLPTTLFQPARAP
              LFQPARAPVTLTAWQNGLLP
                     AWQNGLLPFHSTLTTPGLIW

LTTPGLIWTFTDGTPMISGP
       GTPMISGPCPKDGQPSLVLQ
              GQPSLVLQSSSFIFHKFQTK
                     IFHKFQTKAYHPSFLLSHGL
                            SFLLSHGLIQYSSFHSLHLL

SFHSLHLLFEEYTNIPISLL
       TNIPISLLFNEKEADDNDHE
              EADDNDHEPQISPGGLEPPS

PGGLEPPSEKHFRETEV

Preferred peptides to be synthesized are as follows, wherein the accepted one letter designation for amino acids is used.

| Sequence | ID |
|---|---|
| SFHSLHLLFEEYTNIPISLL | (Seq. I.D. No. 26) |
| SFHSLHLLFE | (Seq. I.D. No. 48) |
| HSLHLLFEEY | (Seq. I.D. No. 49) |
| SFHSLHLLFEEE | (Seq. I.D. No. 54) |
| EEGGSFHSLHLLFE | (Seq. I.D. No. 55) |
| EEGGSFHSLHLLFEEE | (Seq. I.D. No. 56) |
| DPIDGRVIGSALQFL | (Seq. I.D. No. 30) |
| KAYHPSFLLSHGLIQ | (Seq. I.D. No. 31) |
| FNEKEADDNDHEPQI | (Seq. I.D. No. 32) |
| LHLLFEEYTN | (Seq. I.D. No. 50) |
| LLFEEYTNIP | (Seq. I.D. No. 51) |
| EYTNIPISLL | (Seq. I.D. No. 52) |
| IPISLLFNEK | (Seq. I.D. No. 53) |
| FLSEFLHSHL | (Seq. I.D. No. 57) |

Most preferred peptides to be synthesized are as follows, wherein the accepted one letter designation for amino acids is used.

| Sequence | ID |
|---|---|
| SFHSLHLLFEEYTNIPISLL | (Seq. I.D. No. 26) |
| SFHSLHLLFE | (Seq. I.D. No. 48) |
| HSLHLLFEEY | (Seq. I.D. No. 49) |
| SFHSLHLLFEEE | (Seq. I.D. No. 54) |
| EEGGSFHSLHLLFE | (Seq. I.D. No. 55) |
| EEGGSFHSLHLLFEEE | (Seq. I.D. No. 56) |

Such peptides are preferably synthesized as C-terminal amides, and are not acetylated on the N-terminus. In addition the 15mers are preferably synthesized without N-terminal acetylation to potentially increase solubility of the peptides.

Screening Candidate Inhibitor Molecules

Once candidate inhibitors are obtained, they can be assayed to determine their ability to inhibit transactivation. Assays to screen candidate inhibitors include in vitro transcription using nuclear extracts, transfection assays using cultured cells, transgenic and SCID mice animal models, and electrophoretic mobility shift assays (EMSA).

Screening Candidate Inhibitors Using In Vitro Transcription

Synthetic peptides (either random pools or individual peptides representing portions of known transcription factors) can be screened for inhibitory activity in transcription reactions. This involves exposing the synthesized fragments to a mixture of transcription molecules in an in vitro transcription assay and selecting those proteins that inhibit transcription. Preferably, such a mixture of transcription molecules in an in vitro transcription assay includes 1) transactivating factors, 2) auxiliary host cell proteins, 3) target DNA sequences and 4) transcriptional associated elements.

Candidate peptide inhibitors can be screened for the ability to specifically inhibit Tax mediated transactivation by including them in the in vitro transcription reaction. These inhibitors can initially be screened as pools of unpurified peptides. Using pools will be more efficient for screening large numbers of random peptides (Zuckermann et al., (1992) Proc. Nat. Acad. Sci. USA 89:4505–4509; Houghten et al., (1991) Nature 354:84–86). Once inhibitory pools are identified, one can focus on identifying which peptides in the pool are inhibitors. A mock peptide synthesis can be carried out and assayed to ensure that inhibition is due to a specific peptide rather than to a contaminant of synthesis.

Pools of peptides can preferably be screened for their ability to inhibit Tax transactivation of in vitro transcription. Preferably, an in vitro transcription system similar to the one presented in Matthews et al. (1992) Mol. Cell. Biol. 12:1986–1996 will be used. Reactions contain nuclear extracts prepared from HTLV-I infected cells that express Tax or nuclear extracts prepared from uninfected T lymphocytes and purified recombinant Tax. Reactions also contain DNA fragments containing the HTLV-I promoter, Tax responsive cellular promoters such as for IL-2Rα, or reference promoters that are not responsive to Tax, and ribonucleoside triphosphates. Runoff transcripts will be isolated and analyzed by urea-PAGE and phosphor image analysis.

A particularly suitable transcription assay that can be used to screen candidate inhibitors of Tax mediated transactivation can be conducted as follows. Templates containing target DNA sequences used for run off in vitro transcription assays are prepared by excising the appropriate promoter containing target DNA from plasmid DNA using restriction enzymes then isolating the DNA using preparative polyacrylamide gel electrophoresis (PAGE). The templates can be either immobilized or in solution when they are exposed to the other components of the transcription assay.

Immobilized templates are prepared by coupling streptavidin-agarose beads to a biotinylated nucleotide incorporated at the upstream end of the promoter as described previously (Arias and Dynan, (1989) J. Biol. Chem. 264:2021–2033). For experiments performed with immobilized template, preinitiation transcription complexes are formed in the presence of 50–1000 ng of immobilized template, preferably 100–500 ng of immobilized template, more preferably 300–500 ng of immobilized template, most preferably about 300 ng of immobilized template. The immobilized template is mixed with 10–500 µg nuclear extract, preferably 50–200 µg nuclear extract, more preferably 50–100 µg nuclear extract; pools of candidate inhibitors containing approx. 0.1–1000 µM of each peptide, preferably 0.1–1.0 µM of each peptide, more preferably about 0.1 µM of each peptide; and suitable buffers and solvents. A particularly suitable buffer and solvent system is TX buffer (25 mM Tris-HCl pH 7.9, 6.25 mM $MgCl_2$, 0.5 mM EDTA, 0.5 mM DTT, 50 mM KCl, and 10% (v/v) glycerol) in a 50 µl reaction at room temperature to 37° C., preferably about 30° C. for at least about 5 minutes, preferably 15–120 minutes, most preferably about 60 min. Immobilized templates are then washed with buffer, preferably about 3 times with about 1 ml TX buffer and resuspended in buffer, preferably about 50 µl of TX buffer. RNA synthesis is initiated by the addition of adequate amount of trinucleotides, for example, about 250 µM each of ATP, CTP, GTP, 12.5 µM UTP and 0.067 µM [$\alpha$-$^{32}$P] UTP (3000 Ci/mmol). Reactions are terminated and RNA transcripts are isolated and analyzed by urea-PAGE. Relative amounts of RNA are quantitated using a Molecular Dynamics Phosphor Imager.

In vitro transcription assays can also be performed using templates in solution. Promoter fragments are isolated as above but are not biotinylated. Preinitiation complexes are formed in the presence of DNA template, nuclear extract, candidate inhibitors, and buffers. The amount of DNA template is from 10–1000 ng DNA template, preferably 25–500 ng DNA template, more preferably 50–75 ng DNA template, most preferably about 75 ng DNA template. The amount of nuclear extract is 10–1000 µg nuclear extract, preferably 25–500 µg nuclear extract, more preferably 50–200 µg nuclear extract, most preferably about 100 µg nuclear extract. The amount of inhibitor added will depend on the the degree of inhibition it possesses. A typical range of inhibitor will be from equimolar to 1000 fold molar excess with respect to the transcription factor it is trying to outcompete. For example, assume 0.5 µg of purified Tax protein is needed to observe measurable activation of transcription (0.5 µg of a 40 kDa protein in a 50 µl reaction represents 0.25 µM protein final). In this case peptides representing portions of the Tax protein would be added at 0.25–250 µM final and their effects would be measured. If the amount of transcription factor present in the extract is unknown (as is the case for the relative amounts of most of the transcription factors in the extract) and random peptides are being screened then 2.5 to 1000 µM final each peptide will be included in the reaction. This amount will vary depending on the number of peptides in the pool and their solubility. For example a pool of 40 peptides may be quite soluble at 25 µM each while a pool of 400 peptides each at 25 µM would result a total protein concentration above the solubility threshold for several of the component peptides in the mixture. The 2.5 to 25 µM peptide concentration represents a 10 to 100 fold molar excess if one assumes that 50 µg of nuclear extract is used, each transcription factor represents 0.01 to 0.1 percent of the total nuclear protein and has an average MW of 40 kDa.

In the case of using peptides representing a portion of the Tax to compete with Tax for interaction with host cell proteins it is desirable to minimize the amount of Tax required in a reaction. This can be defined by titrating addition of purified recombinant Tax to extracts lacking Tax and determining the minimum amount required to measure transcriptional activation. Alternatively, this can be achieved by preparing extracts from an inducible Tax expressing cell line (such as CEMTax, metallothionein promoter, cadmium inducible) and regulating the amount of induction.

The candidate inhibitors may be added as pools of candidate inhibitors or as individual inhibitors depending on the number to be screened. A suitable buffer is any biological buffer, preferably TX buffer in a 50 µl reaction. The preinitiation complexes are formed at from 4° C. to about 37° C., preferably at from room temperature to about 37° C., more preferably at about 30° C. for at least 5 minutes, preferably for about 5–60 minutes. RNA synthesis is initiated by the addition of an adequate amount of trinucleotides, for example, 250 µM each of ATP, CTP, GTP, 12.5 µM UTP and 0.067 µM [$\alpha$-$^{32}$P] UTP (3000 Ci/mmol). Reactions are incubated for at least 3 minutes, preferably from 5–60 minutes, at from room temperature to 37° C., preferably at about 30° C., and RNA is isolated and analyzed by urea-PAGE as above. Relative amounts of RNA are quantitated using a Molecular Dynamics Phosphor Imager.

Suitable transactivating factors for use in an in vitro transcription assay are any of those that have a target DNA sequence, preferably those transactivating proteins that are viral transactivating proteins, more preferably the transactivating proteins HTLV-I Tax and Hepatitis B Protein X. In the case of Tax, it is preferable to have transcription systems that do and that do not contain Tax for the purpose of evaluating the specificity of the inhibitors. There are two approaches to achieve this: 1) Prepare nuclear extracts from cell lines that do and do not express endogenous Tax, or 2) prepare extracts from cell lines that do not express Tax and add purified recombinant Tax to them. Cell lines that express endogenous Tax include the HTLV-I infected cell line SLB-I that expresses the entire viral genome (Koeffler et al., (1984) Blood 64:482–490) and the HTLV-I transformed T lymphocyte line C81-66-45 (Salahuddin et. al., (1983) Virology 129:51–64) that expresses Tax and not the other HTLV-I gene products. There is also a HeLa cell line that has been transformed with an inducible plasmid that expresses Tax (Alexandre and Verrier (1991) Oncogene 6:543–551 and references therein). HeLa is a human cervical carcinoma cell line. It may be preferable to use a lymphocyte cell line, such as a Jurkat cell line stably transfected with a plasmid expressing Tax under the control of a murine metallothionein promoter (Nagata et al. ((1989) J. Virol. 63:3220–3226). Nyborg et al (unpublished) have stably transfected another T lymphocyte line CEM with the same inducible tax-expressing plasmid. The HTLV-I infected infected T cell line HUT 102 is commercially available (Advanced Biotechnilogies, Inc., Columbia, Md.) and is deposited with the American Type Culture Collection (Rockville, Md., ATCC Accession TIB 162). Tax has been expressed in *E. coli* (Giam et al., (1986) Proc. Nat. Acad. Sci. USA 83:7192–7196; Sanchez et al., (1987) Virology 161:555–560; Goh et al., (1985) J. Virol. 55:497–499; Zhao and Giam, (1991) Proc. Nat. Acad. Sci. USA 88:11445–11449). Tax has also been expressed in *Saccharomyces cerevisiae* (Wu et al., (1992) J. Virol. 66:7523–7261) and in Baculovirus infected Sf9 cells (Jeang et al., (1987) J. Virol 61:708–713; Matthews et al., (1992) Molec. Cell Biol. 12:1986–1996). Tax could be purified from any of these systems. Tax exists as a phosphorylated protein in lymphocytes although it is not known if phosphorylation is required for activity. It will be interesting to compare Tax synthesized in *E. coli* (not phosphorylated) with Tax synthesized in yeast, insect cells, and lymphocytes (phosphorylated).

Auxiliary host cell proteins are those proteins (transcriptional associated proteins) that are involved in regulating the transcriptional process, but which may not be integrally involved in transcription other than in their regulatory role, i.e. they are not a part of the transcriptional machinery only. Auxiliary host cell proteins, although involved in transactivation as an intermediary, are not transactivating factors themselves for purposes of this invention because they are usually naturally occurring in the host cell. Auxiliary host cell proteins may include one or more sequence specific DNA binding proteins, signal transduction components, general transcription factors or tumor suppressors. A recent publication compiled a list of sequence specific transcription factors by the DNA sequences they recognize (Faisst and Meyer, (1992) Nucleic Acid Res. 20:3–26). Another way to classify these proteins is by the structure of their DNA binding domains (e.g., helix-turn-helix, leucine zipper, helix loop helix, zinc finger, yet unclassified motifs; Pabo and Sauer, (1992) Ann. Rev. Biochem. 61:1053–1095) or by their putative activation domains (e.g., acidic activation domain, glutamine rich activation domain, proline rich activation domain) (reviewed in Mitchel and Tjian, (1989) Science 245:371–378). Many of the proteins that can bind to a Tax-responsive element in the HTLV-I promoter are part of the leucine zipper class (ATF/CREB, fos/jun) however a zinc finger protein Sp1 binds to another DNA element in the HTLV-I promoter. Additionally Tax activates transcription through a different DNA element bound by NF-κB whose DNA binding motif is unknown.

General transcription factors include the polymerases, e.g., RNA polymerase II, and transcriptional factors, e.g., TFII-A, TFII-B, and TFII-D through TFII-J. RNA polymerase II is a large mutisubunit enzyme. The purified enzyme alone is unable to bind specifically to promoter DNA and initiate transcription. It requires associated general initiation factors, (TFIIA, B, D–J ) (reviewed in Conaway and Conaway, (1991) J. Biol. Chem. 266:17721–17724; and Zawel and Reinberg, (1992) Progress in Nucleic Acids Research and Molecular Biology). There is some evidence for a viral transactivating protein from herpes simplex virus (VP16) interacting with TFIIB and TFIID. It is likely that the HTLV-I transactivator Tax interacts with RNA polymerase II or its associated factors since a Tax fusion protein (Tax is tethered to DNA by a DNA binding domain of GAL4) can activate transcription from promoters that do not contain binding sites for any other sequence specific transcription factors besides the GAL4 site that the GAL4-Tax fusion binds to. Thus the only other transcription factors bound at this promoter would be RNAP II and general factors.

Additionally there is a class of proteins referred to as tumor suppressors or anti oncogenes. Examples from this class include Rb and p53 (Marshall, (1991) Cell 64:313–326). These proteins are not present in transcription complexes. One way they control levels of transcription is by influencing the pool of transcription factors available. For example Rb binds to the sequence specific transcription factor E2F and prevents E2F from binding to DNA and activating transcription. The viral transactivating protein from adenovirus, E1a activates transcription by disrupting the E2F-Rb interaction (Bagchi et al., (1991) Cell 65:1063–1072; Chellappan et al., (1991) Cell 65:1053–1061; Chittenden et al., (1991) Cell 65:1073–1082).

Auxiliary host cell proteins can be obtained in a number of ways. For example, Tax is known to activate transcription through certain DNA sequence elements including the cyclic AMP response element (CRE) and an NF-κB element. Tax does not bind specifically to either of these elements but rather likely interacts through auxiliary host cell proteins that do bind to these elements. The proteins that bind to these DNA sequences are present in nuclear extracts prepared from T lymphocytes and can be analyzed directly in this crude mixture. These proteins could be purified from the lymphocyte extracts using DNA affinity chromatography (Kadonaga and Tjian, (1986) Proc. Nat. Acad. Sci. USA 16:5889–5893) to purify sequence specific DNA binding proteins. RNA polymerase can be purified from calf thymus as described by Hodo and Blatti (1977 Biochem. 16:2334–2343) or using 8WG16 monoclonal antibodies as described by Thompson et al. (1989 JBC 264:11511–11520). The general transcription factors TFIIA-TFIIJ can be fractionated from Drosophila embryos as described in Wampler et al. (1990 JBC 265:21223–21231) or fractionated from HeLa nuclear extracts as described in Sawadago and Roeder, (1985) Proc. Nat. Acad. Sci. USA 82:4394–4398. TAFs, polypeptides that associate with the TBP fraction of the general factor TFIID can be isolated as described in Dynlacht et al (1991 Cell 66:563–576).

One drawback to this approach is that auxiliary host cell proteins are not present at very high levels in these extracts. Thus it would be desirable to clone these proteins and to subclone them into *E. coli* expression vectors. For DNA binding proteins, this is done by probing a lymphocyte cDNA expression library with a radiolabelled single or double stranded oligonucleotide representing the target DNA sequence (method in Current Protocols in Molecular Biology., ed. Ausubel et. al. (1991), John Wiley & Sons, New York). In fact a number of these factors have already been cloned, and some subcloned into expression vectors. For example, cDNA clones of NF-κB have been isolated and subcloned into both *E. coli* and mammalian expression vectors, such as cDNA clones of p50 and p65 [Ghosh, S. et al. (1990) Cell 62:1019–1029; Kieran, M. et al., (1990) Cell 62:1007–1018; Nolan et al. (1991) Cell 64:961–969, (murine p65 clone); and Ruben et al., 1991. Science 251:1490–1493]. Some of the above cDNA clones were subcloned into bacterial and mammalian expression vectors (Ruben et al., (1992) Mol. Cell Biol. 12 (2):444–454; Ruben et al., (1989) Proc. Nat. Acad. Sci. USA 86:821–824) The consensus DNA recognition sequence of the CRE which is bound by members of the ATF/CREB transcription factor family and the consensus DNA recognition sequence for AP-1 which is bound by members of the fos/jun transcription factor family differ by only one nucleotide out of eight. These DNA elements can be bound by homomeric and heteromeric combinations of transcription factors and there is cross family dimerization between the ATF/CREB and fos/jun families. Although these factors are very similar in their DNA binding and dimerization domains, their ability to activate transcription varies greatly. At least 10 different mammalian cDNA have been described that encode proteins that bind to the CRE (Hoeffler et al., (1988) Science 242:1430–1433; Gonzalez et al., (1989) Nature 337:749–752; Hai et al., (1989) Genes and Dev 3:2083–2090; Maekawa et al., (1989) EMBO 8:2023–2028; Gaire et al., 1990 Nucleic Acids Res. 18:3467–3473; Ivashkiv et al., (1990) Mol. Cell Biol. 10:1609–1621; Foulkes et al., (1991) Cell 64:739–749; Hsu et al., (1991) Proc. Nat. Acad. Sci. USA 88:3511–3515).

Some of these have been subcloned into expression vectors. The cDNA for CREB (Gonzalez et al., (1989) Nature 337:749–752) was subcloned into the pET-11a expression vector by Zhao and Giam ((1992) Proc. Nat. Acad. Sci. USA 89:7070–7074). The cDNAs for human CREB-A and CREB-B (Berkowitz and Gilman, (1990) Proc. Nat. Acad. Sci. USA 87:5258–5262) were subcloned into the pET3b expression plasmid by Franklin et al., J. Biol. Chem. (1993) 268:21225–21231. The cDNA for ATF-1(Hai et al., (1989) Genes and Dev. 3:2083–2090) was subcloned into the expression plasmid pET-11d by Zhao and Giam ((1992) Proc. Nat. Acad. Sci. USA 89:7070–7074) and into expression vector pET-3b by Hoeffler et al., (1991) Molecular Endocrinology 5:256–266). The cDNA for ATF-2 which is identical to CRE-BP1(Maekawa et al., (1989) EMBO 8:2023–2028) was subcloned into expression vector pET-3b by Hoeffler et al., (1991) Molecular Endocrinology 5:256–266).

Some auxiliary host cell proteins are commercially available including AP1 (cjun), AP2, Sp1, TBP, NF-kB, and TFIIB (Promega, Inc. Madison, Wis.).

Suitable target DNA sequences will be those sequences that up regulate transcription of the corresponding gene in the presence of the transactivating protein. Such DNA sequences can be in the regulatory region of the gene upstream, downstream or within the coding region. More preferably, they can be selected from Tax responsive elements (TxRE) in an HTLV-I LTR proviral promoter, Tax responsive cellular promoters targeted through a CRE (e.g., fos), Tax responsive cellular and viral promoters targeted through an NF-κB element (e.g., IL-2, IL-2Rα, GM-CSF, HIV), promoters that are repressed rather than activated by Tax (e.g., β polymerase), and promoters not responsive to Tax. Most preferably, the target DNA sequence will be a Tax responsive element (TxRE) in an HTLV-I LTR proviral promoter. In the case of the TxRE in an HTLV-I LTR, the reference promoters used in the initial screening will not be Tax responsive. Once inhibitors of Tax-mediated transactivation of the HTLV-I LTR have been identified, they will be tested on known Tax responsive cellular promoters. Several of these promoters regulate expression of genes involved in control of cell growth. Transcription of these genes is increased in the presence of Tax, and likely contributes to viral oncogenesis. Ideally, one would want the peptide inhibitors of Tax to have no effect on these genes in the absence of Tax. In the presence of Tax, these cellular genes are upregulated, so it may be desirable to have the Tax inhibitor down regulate their expression as well. It is possible that an inhibitor of Tax transactivation of the HTLV-I promoter (ATF/CREB responsive) may have no effect on NF-κB responsive cellular promoters such as IL-2 and IL-2Rα. Since Tax regulates its own synthesis by activating transcription of the HTLV-I LTR, the inhibitor will reduce the pool of active Tax protein in the cell. In an in vitro transcription system therefore, one might simply observe the false negative that an inhibitor had little effect on Tax transactivation of NF-κB responsive promoters.

Target DNA sequences can be obtained by chemical synthesis or by excising recombinant DNA fragments using restriction enzymes.

The complete nucleotide sequence of the HTLV-I proviral genome was first reported by Seiki et al. ((1983): Proc. Nat. Acad. Sci. USA 80:3618–3622). The HTLV-I transcriptional control region extends over 300 bp and has a structure typical of a promoter transcribed by RNAP II. Sequences proximal to the start site include a TATA element, and region designated as Site 4 where at least three different factors bind (Nyborg et al., (1990) J. Biol. Chem. 265:8230–8236; Nyborg et al., (1988) Proc. Nat. Acad. Sci. USA 85:1457–1461). The Tax responsive elements (TxREs) in the HTLV-I LTR were determined by genetic and deletion analysis. These experiments identified a 21 bp sequence, imperfectly repeated 3 times in the HTLV-I promoter, that can mediate Tax transactivation (Shimotohno et al., (1986) Proc. Nat. Acad. Sci. USA 83:8112–8116; Brady et al., (1987) J. Virol. 61:2175–2181; Jeang et al., (1988) J. Virol. 62:4499–4509; Fujisawa et al., (1989) J. Virol. 63:3234–3239; Giam and Xu, (1989) J. Biol. Chem. 264:15236–15241; Montagne et al., (1990) EMBO J. 9:957–964). Although not identical, each 21 bp repeat TxRE will support transactivation when inserted in an appropriate promoter context (Jeang et al., 1988; Fujisawa et al., 1989; Giam and Xu, 1989; Montagne et al., 1990). A different element, Site 2a, between the second and third 21 bp repeats, can increase the response to Tax when in the context of at least one 21 bp repeat TxRE (Brady et al., (1987) J. Virol. 61:2175–2181; Marriott et al., (1989) Mol. Cell Biol. 9:4152–4160; Marriott et al., (1990) Mol. Cell Biol. 10:4192–4201). Promoter elements that can be inserted into the pGL2-basic vector (Promega, Madison, Wis.) include the wild type LTR (nucleotides −353 to +137 relative to the RNA start site) and individual promoter elements include (nucleotide positions shown relative to RNA start site, linker sequences shown in bold, complement strand not shown):

HTLV-I TATA element(−40 To +15) (Seq. I.D. No. 33)
GATCTCTAGCAGGAGTCTATAAAAGCGTGGAGACAGTTCAGGAGGGGGCTCGCATCTCTCCA HTLV-I (−104 to −84) third 21 bp repeat (Seq. I.D. No. 34)
GATCTTCAGGCGTTGACGACAACCCCG HTLV-I Site 2a (−160 to −117) (seq. I.D. No. 35)
GATCTCCTCCGGGAAGCCACCAAGAACCACCCATTTCCTCCCCATGTTTG HTLV-I 21 bp repeats 1 and 2 (−253 to −183) (Seq. I.D. No. 36)
GATCTAAGGCTCTGACGTCTCCCCCCGGAGGGCAGCTCAGCACCGGCTCGGGCTAGGCCCTGAC
GTGTCCCCCTG HTLV-I 21 bp mutant (Seq. I.D. No. 37)
GATCTTCAGGCGTAAGGAGCAACCCCG There are other cellular promoters containing a CRE. Tax activates transcription of the human proto-oncogene c-fos (Nagata et al., (1989) J. Virol 63:3220–3226). Alexandre and Verrier ((1991) Oncogene 6:543–551) identified four Tax responsive elements in the human c-fos promoter: a cyclic AMP response element (CRE) at −63 to −57 relative to the RNA start site (Sassone-Corsi et al., (1988) Genes Dev. 2:1529–1538); a Serum Response Element (SRE) centered at −315 relative to the RNA start site (Fujji et al., (1988) Proc. Nat. Acad. Sci. USA 85:8526–8530); a v-sis conditioned medium inducible element (−350) (Hayes et al., (1987) Proc. Nat. Acad. Sci. USA 84:1272–1276); and an octanucleotide direct repeat (DR at −87) (Fisch et al., (1987) Mol. Cell Biol. 7:3490–3502). The wild type human c-fos and also chimeric promoters containing the elements described above will be investigated.

Tax activates transcription of another cellular promoter involved in control of cell growth granulocyte-macrophage colony stimulating factor (GM-CSF), perhaps through sequences distinct from a CRE or NF-κB element (Nimer et al., 1989 Oncogene 4:671–676).

There are also cellular and viral promoters that contain an NF-κB element. The promoters of interleukin-2 (IL-2), interleukin-2 receptor alpha chain (IL-2Rα) and the human immunodeficiency virus (HIV) are all Tax responsive. All of them contain NF-κB binding sites (Listed in Lenardo and Baltimore, (1989) Cell 58:227–229) that may mediate the Tax response. These sequences will be investigated, as will the entire wild type promoters for these genes. IL-2Rα promoter sequences are described in Cross et al., (1987) Cell 49:47–56. The HIV LTR sequence is described in (Sodroski et al., (1985) Science 229:74–77). The IL-2 promoter sequence is described in (Siebenlist et al., (1986) Mol. Cell Biol. 6:3042–3049).

Tax is also a trans-repressor of the human B polymerase gene (humβ-pol) (Jeang et al., (1990) Science 247:1082–1084). This enzyme is involved in host cell DNA repair. Many Adult T cell Leukemia (ATL) patients have chromosomal damage (Fukuhara et al., (1983) Blood 61:205). Host cell DNA damage may be an additional event needed post HTLV-I infection to result in the development of ATL (Yoshida and Seiki, (1987) Ann. Rev. Immunol. 5:541–549). The effect of Tax on the huB-pol promoter sequences (Widen et al., (1988) J. Biol. Chem. 263:16992) will be investigated. The regulatory sequences of the huB-pol promoter have been characterized (Widen et al., (1988) J. Biol. Chem. 263:16992). Interestingly, this promoter contains a CRE (TGACGTCA) that is similar to the CRE contained in the 21 bp repeat elements in the HTLV-I promoter. Jeang et al. ((1990) Science 247:1082–1084) demonstrated that the huB-pol CRE is is not required for Tax-mediated repression of transcription from the huB-pol promoter. Thus, Tax mediated repression likely occurs through other DNA sequence elements described in Widen et al., (1988) J. Biol. Chem. 263:16992.

Promoters unresponsive to Tax can also be used as controls for nonspecific inhibition and as references for levels of Tax activation. Tax was shown by CAT assays to have no effect on an enhancerless SV40 promoter which still contained the GCbox region pΔSV-2CAT (Fujisawa et al., (1986) EMBO 5:713–718), pSV1Ccat, and the Rous sarcoma virus LTR (pRSV-CAT) (Saito et al., (1988) J. Virol. 62:644–648). A deletion mutant of the HTLV-I LTR to −52 (pU3RCAT dl6-2) was shown to be unresponsive to Tax in a transfection assay (Brady et al., (1987) J. Virol. 61:2175–2181) and activated only 2 fold in a runoff transcription assay (Matthews et al., 1992 Mol. Cell Biol. 12:1986–1996). A chimeric promoter containing three Sp1 sites and the TATA element from HSV-tk was also shown to be at best 2 fold activated by Tax in this assay.

One or more transcriptional associated elements can also be important parts of an in vitro transcription assay. These elements are integral components of the transcriptional machinery apart from any role they may play as a mediator of transactivation. They can include many of the general transcription factors that are also auxiliary host cell proteins. General transcription factors that can be transcriptional associated elements include the polymerases, e.g., RNA polymerase II, and transcriptional factors, e.g., TFII-A, TFII-B, and TFII-D through TFII-J. Other transcriptional associated elements that can be included in in vitro assays include adenosine triphosphate (ATP) as an energy source and structural element of oligonucleotides and the various other nucleoside triphosphates (NTP's) such as guanosine triphosphate (GTP), cytosine triphosphate (CTP), and uracil triphosphate (UTP). Nucleotides can be obtained from Pharmacia or Sigma. Radiolabelled nucleotides can be obtained from Dupont-NEN or ICN. RNA polymerase can be purified from calf thymus as described by Hodo and Blatti (1977 Biochem. 16:2334–2343) or using 8WG16 monoclonal antibodies as described by Thompson et al. (1989 J. Biol. Chem. 264:11511–11520). The general transcription factors can be fractionated from Drosophila embryos as described in Wampler et al. (1990 J. Biol. Chem. 265:21223–21231) or fractionated from HeLa nuclear extracts as described in Sawadago and Roeder, (1985) Proc. Nat. Acad. Sci. USA 82:4394–4398. Alternatively, several of the general transcription factors have been cloned an can be expressed in and purified from $E.\ coli$. Zawel and Roeder (1992 Progress in Nucleic Acids Research and Molecular Biology in press) and references therein. TAFs, polypeptides that associate with the TBP fraction of TFIID can be isolated as described in Dynlacht et al (1991 Cell 66:563–576). Many of the TAF polypeptides are currently being cloned and production of recombinant TAFs in $E.\ coli$ are within the skill of the art.

The nuclear extract can be obtained from lymphocytes. CEM T lymphocytes (Slamon et al., (1985) Science 228:1427–1430) and CEM T lymphocytes stably transfected with an inducible Tax-expressing plasmid, CEM Tax (Nyborg, Colorado State University, Fort Collins, Colo.) are grown in spinner culture at 37° C. using Iscove's medium supplemented with 5% fetal bovine serum, 5% calf serum, and glutamine. HTLV-I infected, Tax-expressing SLB-I cells (Koeffler et al., (1984) Blood 64:482–490) and HTLV-I infected HUT102 cells (ATCC TIB 162; Advanced Biotechnologies, Inc., Columbia, Md.) are grown in T-150 flasks at 37° C. using the same medium. Nuclear extracts are prepared as described below (adapted from Dynan, (1987) *Genetic Engineering: Principles and Methods*, Plenum Publishing, New York). Cells are harvested by centrifugation and washed with phosphate buffered saline. All buffers contain 1 μg/ml of the protease inhibitors phenylmethylsulfonyl fluoride, leupeptin, aprotinin, and soybean trypsin inhibitor. The cell pellet is resuspended in 4 packed cell volumes (PCV) of hypotonic lysis buffer (10 mM Tris, pH 7.9, 10 mM KCl, 1.5 mM MgCl$_2$, 1 mM DTT) and incubated on ice 10 min. The cell suspension is homogenized, nuclei are pelleted by centrifugation and washed with 2 PCV of hypotonic lysis buffer. Isolated nuclei are resuspended in 4 PCV of nuclear extraction buffer (0.05M Tris-HCl pH 7.9, 0.42M KCl, 0.005M MgCl$_2$, 0.001M EDTA, 0.002M dithiothreitol (DTT), 20% (v/v) glycerol, 10% (v/v) sucrose), stirred on ice for 60 min. and centrifuged for 30 min. at 17,000 rpm in a Dupont Sorvall SS-34 fixed angle rotor. High speed supernantant (HSS) is removed and 0.33 g/ml ammonium sulfate is added to the supernatant and stirred for 60 min on ice. Precipitated proteins from HSS are pelleted by centrifugation for 10 min. at 15,000 rpm in the SS-34 rotor, resuspended in 0.05 volumes of TM buffer (0.050M Tris-HCl pH 7.9, 0.0125M MgCl$_2$, 0.001M EDTA, 0.001M DTT, 20% (v/v) glycerol) containing 0.1M KCl, dialyzed against the same buffer overnight, and frozen at −70° C.

Screening Candidate Inhibitors Using Transfection Assays

Synthetic peptides (either random pools or individual peptides representing portions of known transcription factors) can be screened for inhibitory activity in transfection experiments.

Transfection assays are performed as mammalian cell tissue assays. They test effectiveness of both the transactivating protein and auxiliary host cell protein derived peptides in a mammalian cell tissue culture system using the target DNA sequence, such as the HTLV-1 LTR in the case of Tax transactivation, linked to a reporter gene and the transactivating protein supplied in trans under regulation of an inducible promoter such as metallothionein or a constitutive promoter such as CMV promoter. Induction of the transactivating protein will result in expression of the reporter gene which can be quantitatively monitored. Optimized inhibitors can then be tested for their ability to inhibit expression of the reporter gene when the inhibitor is introduced into the mammalian cell tissue medium.

In a particularly suitable transfection assay, transcription can be studied directly or indirectly by linking a promoter or enhancer region to a reporter gene such as chloramphenicol acetyl transferase (CAT) or luciferase. This plasmid is then introduced into the cultured cell line of choice. Foreign DNA can be introduced into cultured eukaryotic cells (transfected) either transiently or stably. Mechanisms for introducing DNA into cells include calcium phosphate transfection, transfection using DEAE-Dextran, transfection by electroporation, and liposome-mediated transfection (detailed in *Current Protocols in Molecular Biology*, ed. Ausubel et. al. (1991), John Wiley & Sons, New York). Peptides may also be introduced into cells by electroporation and by liposome-mediated transfection. The relative level of transcription directed from that promoter can then be measured directly by harvesting the cellular RNA and probing for the mRNA of the reporter gene or indirectly by preparing a cell lysate and assaying for the activity of the reporter gene product. Methods for direct analysis or RNA after transfection, for harvesting cells and performing CAT assays and for harvesting cells and performing luciferase assays are detailed in *Current Protocols in Molecular Biology*, ed. Ausubel et. al. (1991), John Wiley & Sons, New York).

Transfection assays can be used to screen a number of compounds for the ability to inhibit Tax transactivation or alternatively to evaluate an inhibitory compound already characterized in a cell free transcription assay for the ability to inhibit Tax transactivation in cultured cells and to begin to evaluate its cytotoxicity. Choosing which cell lines to transfect is an important part of the assay. T-lymphocyte cell lines should be used for measuring efficacy, since they are the HTLV-I host cells. Being consistent, the cell lines used to prepare extracts for the cell free run-off transcription assay will also be used for the transfection assay. Additional cell lines that might be used include Jurkat uninfected human T lymphocyte, HUT 78 an HTLV negative human T-lymphocyte cell line, C81-66-45 an HTLV-I immortalized nonviral producer (produces Tax), HUT-102 HTLV-I producer T lymphocyte line, MT2 HTLV-I producer T-lymphocyte cell line C3-44 HTLV-LI producer T-lymphocyte cell line (these lines are used in Sodroski et al., (1984) Science 225:381–385). In addition to human T-lymphocytes, other cell types found in the peripheral blood stream (that might be exposed to the inhibitor) may also be used. Some of the promoter constructs that can be characterized are described above.

A number of compounds could be rapidly screened for inhibition of transcription from the HTLV-I LTR, inhibition of transcription from a reference promoter such as the Rous sarcoma virus RSV-LTR, and cytotoxity in a random screening assay as follows. Transiently co-transfect a Tax-producing human T-lymphocyte cell line (e.g., C81-66-45 or induced CEMTax) with a plasmid containing the HTLV-I LTR upstream of the firefly luciferase gene and another plasmid containing the RSV LTR upstream of the CAT gene. Aliquot the transfected cells into a 96 well microtiter plate. To the different wells add either a mock inhibitor (buffer only) or increasing amounts of different inhibitors. Allow the cells to continue growing for a suitable period, preferably 12–48 hrs. Analyze one fraction of the cells in one well for viability by trypan blue staining. Analyze another fraction of the cells from that well for transcription from the HTLV-I LTR by measuring luciferase activity. Analyze another portion of the cell from that well for transcription from the RSV-LTR by measuring CAT activity. (Alternatively, prepare one sample of cellular RNA and probe for both CAT and RSV mRNA by Northern blotting). Normalize the results of wells containing candidate inhibitors to wells containing mock inhibitors.

Results and interpretations of the transfection assay can be made as follows:

(A) If candidate inhibitor has no effect on any of the three assay points (cell viability, Tax-dependent transcription, Tax independent transcription) it may not be inhibitory at the concentrations tested or it may not have been able to enter the cell and the cell nucleus at sufficient concentrations to inhibit. If this result is observed for an candidate inhibitor that inhibited Tax-dependent transcription in a cell free assay, then it would be useful to evaluate uptake by using a radiolabelled inhibitor and isolating whole cells as well as cytoplasmic and nuclear cell fractions.

(B) If a candidate inhibitor results in no viable cells then it may or may not inhibit Tax-mediated transcription and should be tested at lower concentrations.

(C) If a candidate inhibitor resulted in decreased transcription from both the HTLV-I LTR and the RSV-LTR then it may interact either directly with components of the general transcriptional machinery (RNAP II and associated general factors) or influence the availability of these components. If this inhibitor did not dramatically decrease cell viability, then it should be investigated further. Random modifications of it could be made and screened (e.g., change 1 amino acid at a time, or lengthen or shorten) or its target could be determined by methods discussed in another section (radiolabelling and probing libraries, using as an affinity column).

(D) An inhibitor abolishes transcription from the HTLV-I LTR and has no effect on transcription from the reference promoter or cell viability. This may be a strong candidate for a product, however, note that it abolished rather than decreased transcription from the HTLV-I promoter. One would expect the HTLV-I LTR to be transcribed at a very low level in the absence of Tax, so abolition is unexpected. One possibility is that non-productive transcription complexes were locked onto the promoter. Since Tax activates transcription from a number of cellular genes, this inhibitor could have potential deleterious effects on the cell (although none were observed as measured by cell viability over the period of this assay). Thus it would be informative to screen RNA prepared from cells treated and untreated with this inhibitor for mRNAs from know Tax responsive cellular genes (c-fos, IL-2, IL2-Rα, GM-CSF, humβ pol.

(E) An inhibitor decreases transcription from the HTLV-I LTR and has no effect on cell viability or transcription from the RSV promoter. This result indicates a strong candidate for an inhibitor, however further investigation is required. Tax is thought to activate transcription of the HTLV-I LTR through a CRE but Tax is thought to activate other cellular promoters through different DNA sequences including an NF-κB element. Since a number of these genes are involved in regulation of cell growth, it may or may not be necessary to inhibit Tax mediated activation of these promoters as well as the viral promoter to inhibit cellular transformation and development of ATL. Thus one could probe mRNA levels of these genes in non-Tax-expressing cells, Tax-expressing cells, and Tax expressing cells treated with the inhibitor. Alternatively, one could proceed to animal models and look for inhibition of Tax-mediated tumor promotion.

Screening inhibitors also can be performed using a cell line that is stably transfected. Most of the above remarks and examples apply here. The major modification is that one might want to use a cell line stably rather than transiently transfected with the HTLV-I LTR. This would result in a constant amount of promoter DNA present in experiments done on different days and simplify comparison of concentrations of different inhibitors required to see an effect. Another way to achieve this would be to use an HTLV-I producing cell line (HTLV-I LTR is integrated into the chromosome of the host cell) and measure transcription by northern blotting used probes for HTLV-I mRNA and mRNAs from cellular genes activated by Tax. The disadvantage to a stable transfectant is the time and effort required to generate it; the disadvantage to working with infected cells is obvious.

Another possible way to find a peptide inhibitor of Tax transactivation activity is to construct a system for directly selecting such an inhibitor from among a large set of random peptides. Such a system could consist of the following: a tissue culture cell line expressing the Tax gene and a "killer" gene from a Tax responsive promoter, growth conditions which are lethal to cells expressing such a "killer" gene, and a library of plasmids which can be transfected into the cell line and which express small random peptides The cell line could be cultured under "permissive" growth conditions such that expression of the "killer" gene is not lethal, transfected with the library of random peptide expressing plasmids, and then transferred to "restrictive" or "nonpermissive" growth conditions where "killer" gene expression causes cell lethality. Following this procedure, only cells containing a plasmid expressing a peptide which can inhibit Tax transactivation of the "killer" gene would remain viable. Such rare cells could then easily be isolated, cultured, and the DNA sequence of the small peptide expressing gene identified using standard molecular biology techniques.

Tissue culture cell lines expressing the Tax gene have been made and are publicly available. The Jurkat-Tax (Nagata et al. (1989) J. Virol 63:3220–3226) or CEMTax (Nyborg unpublished) cell lines would be most preferable since Tax expression is inducible rather than constitutive, since expression of the killer gene is regulated by Tax. Cell lines that constitutively express Tax include C81-66-45 (Salahuddin et al., (1983) Virology 129:51–64) which expresses Tax and not several other HTLV-I genes and the HTLV-I infected cell line SLB-I (Koeffler et al., (1984) Blood 64:482–490).

There are a number of "killer" genes and permissive/restrictive growth conditions that could be used. The first example is expression of the thymidine kinase (TK) gene and growth media with ("restrictive" condition) or without ("permissive" condition) 5-bromodeoxyuridine (BrdU). BrdU is phosphorylated by thymidine kinase and incorporated into DNA where it causes a very high frequency of mutations during DNA synthesis and consequent cell lethality. Cells containing TK are not viable in the presence of BrdU; cells not expressing TK are unaffected by BrdU. Expression, under restrictive conditions, of a small peptide which inhibited Tax transactivation, would prevent TK gene expression and allow a cell to remain viable in the presence of BrdU.

A library of plasmids expressing different small random peptides could be made in various ways. One examples is as follows: Synthetic, single stranded oligonucleotides are made with the sequence: (restriction site 1)..(NNK)$_n$.. (restriction site 2), where N=G,A,T, or C,K=G or T, n=the desired length of the peptides in amino acid residues, and restriction sites 1 and 2 are chosen for convenience in subsequent cloning steps. These oligonucleotides are converted, as a pool, into double stranded DNA structures using the polymerase chain reaction (PCR) technique, digested with restriction enzymes 1 and 2 and then ligated into a plasmid at a site chosen to be appropriately spaced for proper gene expression behind a eukaryotic promoter sequence.

Once the tissue culture cell line containing the Tax and killer genes has been constructed and the library of random peptide expressing plasmids made, these could be combined and the genetic selection carried out as follows: Under non-restrictive, or permissive conditions, the plasmid library could be transfected into the cell line using standard techniques. After the cells have recovered from the transfection procedure and had sufficient time to express the genes on the plasmid, they would be switched to the restrictive conditions for a period long enough to kill all cells in which Tax transactivation of the killer gene occurs. Cells which remain viable would be individually cloned and grown into small subcultures under permissive conditions and the sequence of the peptide gene determined by standard PCR and DNA sequencing techniques. A second selection will be performed to control for false positives. It is likely that not only cells containing peptides that inhibit Tax transactivation but also cells that develop mutations in the killer gene or lose the killer gene will survive. Thus, the DNA from all surviving cells will be isolated and the DNA encoding peptide will be amplified by PCR. One portion of this DNA will be circularized (PCR primers are designed such that both peptide coding sequences and sequences required for expression of peptide will be amplified) and transfected into fresh cells containing an intact killer gene. The other portion will be sequenced. Peptide encoding DNA sequences recovered through two rounds of selection will be used to chemically synthesize their respective peptides and tested in in vitro transcription assays. Peptide encoding DNA sequences recovered through a single round of selection may also be tested. Peptides which allow cells to remain viable under restrictive conditions would be individually tested for their ability to inhibit Tax transactivation by synthesizing the peptide and assaying it's inhibitory activity in a standard in vitro transcription system with Tax protein and a Tax responsive promoter.

Screening Candidate Inhibitors Using Transgenic and SCID Mice Animal Models

Synthetic peptides (either random pools or individual peptides representing portions of known transcription factors) can be screened for inhibitory activity in transfection experiments. There are methods in the literature for infecting SCID mice with HTLV-I. Some of these mice develop lymphatic tumors characteristic of ATL. Candidate inhibitor molecules can be tested for the ability to delay tumor formation and to decrease the size of existing tumors.

There are methods in the literature for infecting WKA rats with HTLV-I. Some of these rats go on to develop hind leg spasticity and spinal cord lesions characteristic of HAM/TSP. Candidate inhibitor molecules can be tested for the ability to prevent or decrease spinal cord lesions and spasticity in these rats.

Transgenic mice have been produced previously [U.S. Pat. No. 4,736,866; U.S. Pat. No. 5,175,385; and U.S. Pat. No. 5,175,384]. The transgenic mice carry the tax gene. Syngenic mice that have been injected with tumor cells isolated from the transgenic mice can be produced as described in Kitajima et al., (1992) Science 258:1792-1795. The transgenic and syngenic mice are then treated with the inhibitor proteins. Observations and measurements can be made to determine if symptoms are alleviated.

Screening Candidate Inhibitors using Electrophoretic Mobility Shift Assay (EMSA)

EMSA is performed by combining radiolabelled target DNA with one or more of auxiliary host cell proteins, transcriptional associated elements, and transactivating factors. The labelled DNA alone will migrate by electrophoresis at a fast rate because of its low molecular weight. When DNA binds to other molecules its electrophoretic mobility in the gel will be retarded or "shifted" up in the gel. The extent of the shift will depend on the mass and shape of proteins bound. A preferred binding reaction contains sufficient [$^{32}$P] end-labelled double stranded synthetic oligonucleotide or recombinant DNA fragments, preferably about 0.33 nM (10-700 base pairs, preferably 10-500 base pairs, preferably 30-200 base pairs) of a recombinant DNA fragment that has been obtained using appropriate restriction enzymes; poly (dI-dC); a suitable buffer to maintain about neutral pH, e.g., 25 mM Tris-HCl pH 7.9; appropriate salts and solvents, e.g., 6.25 mM $MgCl_2$, 0.5 mM EDTA, 0.5 mM DTT, 60-120 mM KCl, and 10% (v/v) glycerol in a 30 µl reaction volume. The amount of poly (dI-dC) is 10 to 1000 ng, and poly (dI-dC) is an alternating copolymer used to compete with the labelled DNA probe for non-specific DNA binding proteins. A lower amount of 10-200 ng will be used in reactions containing relatively purified protein preparations and higher amounts will be used with crude protein fractions, especially nuclear extracts, that likely contain a number of different DNA binding proteins. Some reactions also contain purified recombinant auxiliary host cell proteins, transcriptional associated elements, Tax protein and candidate peptide inhibitors. Reactions are incubated on ice for sufficient time to allow binding to occur, for example 1 minute to 1 hour, preferably 5 to 30 minutes, more preferably about 10 minutes. The temperature can be anywhere between 4° C. to 50° C., preferably from 4° C. to 37° C. The reactions are then analyzed on electrophoresis gels, preferably polyacrylamide gels, more preferably 5% non-denaturing polyacrylamide gels (49:1, acrylamide:N,N-methylene bisacrylamide). Electrophoresis is performed in an appropriate buffer such as one that contains, for example, 0.04M Tris, 0.306M glycine, pH 8.5, and 0.1% Nonidet P-40. Gels are dried and autoradiographed, and relative amounts of protein-DNA complexes are quantitated using Phosphor Image Analysis.

In the EMSA assay, the transactivating protein or fragment, the target DNA, and the auxiliary host cell proteins (also known as transcriptional associated proteins) can be the same as they are in the in vitro transcriptional assays.

In the case of Tax, several different effects may be observed when Tax is present in an EMSA reaction. One effect is an increase in amount of protein-DNA complex formed. For example, Matthews et al. ((1992) Mol. Cell. Biol. 12:1986-1996) and Franklin et al. ((1993) J. Biol. Chem. 268:21225-21231) reported that 21 bp repeat binding proteins purified from lymphocytes shifted the mobility of an oligonucleotide containing the 21 bp repeat sequence. When Tax was included in the reaction an increase in the amount of shifted complex rather than a novel "supershifted" (more slowly migrating complex) was detected. Recently, Franklin et al., (1993) J. Biol. Chem. 268:21225-21231, reported that Tax increased the amount of complex formed in EMSA reactions containing CREB and an HTLV-I 21 base pair repeat DNA sequence. Wagner and Green, (1993) Science 262:395-399, also reported that Tax increased the amount of complex in reactions containing CREB and DNA and they proposed that TAx increased the amount of complex by promoting dimerization of CREB. One might suggest that Tax transactivates transcription by loading auxiliary host cell transcription factors onto their target DNA sequences. Alternatively, one might suggest that Tax transactivates transcription by binding to its target DNA indirectly through the auxiliary host cell proteins, but that this interaction is not stable to electrophoresis. Thus an apparent increase in auxiliary host cell protein-DNA complexes is observed rather than a novel complex between Tax-auxiliary host cell protein-DNA. Regardless of which mechanism is correct candidate inhibitors can be screened under these experimental conditions. Candidate inhibitors can be added to the binding reactions. Peptides that caused the amount of complex formed in the presence of Tax to decrease to the amount of complex formed in the absence of Tax and also peptides that abolished complex formation will then be tested in in vitro and in vivo transcription assays. It is possible that a peptide may instead increase the amount of complex formed or result in a novel complex containing Tax. Although this peptide could activate rather than inhibit transactivation by Tax, further characterization of the peptide and factors it interacts with can help to identify the auxiliary host cell protein required for Tax transactivation.

Another effect of Tax in EMSA reactions has been reported by Zhao and Giam ((1991) Proc. Nat. Acad. Sci. 88:11445-11449). These EMSA binding reactions contained an oligonucleotide probe with two copies of the 21 bp repeat target DNA sequence and unfractionated extracts from Jurkat T-lymphocytes. Addition of Tax to the binding reactions resulted in a novel supershifted complex. Giam's group has also performed EMSA reactions containing CREB and an HTLV-I 21 base pair repeat (Zhao and Giam (1992) Proc. Natl. Acad. Sci. USA 89:7070-7074; Paca-Uccaralertkun et al., (1994) Mol. Cell. Biol. 14:456-462). When antiserum against Tax is also added to the EMSA, the protein-DNA complex is supershifted, indicating that Tax is present in the complex. This anti serum is also available from the AIDS Research and Reference Reagent Program (Rockville, Md. Catalogue No. 467). Candidate inhibitors also will be screened under these experimental conditions. Those peptides that abolish the supershift or abolish all protein-DNA interactions will be further characterized.

The different experimental observations described above, (increased complex versus novel complex) may reflect a requirement for two target DNA sequence or a crude protein preparation containing cofactors for Tax to stably interact with its target DNA sequence. If several auxiliary host cell proteins (e.g. cofactor and DNA binding protein) are required for Tax to stably bind to its target sequence then a candidate inhibitor of transactivation may be that portion of the auxiliary host cell cofactor that interacts with Tax. In addition to EMSA, analytical gel filtration chromatography will be useful in identifying the auxiliary host cell proteins.

Binding reactions are carried out similar to those in EMSA. The DNA probe may not be radiolabelled. All fractions may be analyzed by SDS-PAGE, or fractions are then analyzed by measuring their absorbance at 260 nm. Fractions which absorb at 260 nm will be analyzed by SDS-PAGE and western blotting to determine the identity of the proteins in the protein-DNA complexes (either by molecular weight or antibody reactivity). Free DNA will migrate slowly through the gel filtration matrix, auxiliary host cell protein-DNA complexes will migrate more quickly, and Tax-auxiliary host cell protein-DNA complexes will migrate even more quickly.

To determine the location on a particular piece of target DNA sequence where binding of the transactivators occurs, DNase I footprinting can be performed (Dynan, (1987) *Genetic Engineering: Principles and Methods*, Plenum Publishing, New York). Protein-DNA binding reactions are conducted as in the EMSA. Rather than the doubly end-labelled probe used in EMSA the footprinting probe is singly 5' end labelled on either the sense or nonsense strand. After the binding reaction is complete, samples are digested with DNase I. Exposure to the DNase I is limited to a short period of time, preferably about 30–90 seconds on ice, so that each individual target DNA sequence is cleaved at a minimal number of sites, preferably only one site per molecule. Samples are electrophoresed on a denaturing urea-polyacrylamide gel. Maxam Gilbert sequencing reactions may also be loaded onto the gel and run in parallel with the DNase I digested reactions. The electrophoresis pattern for the DNA will be a ladder with each rung being a DNA strand of a particular length. Those samples that have been exposed to the appropriate transactivating protein mixture containing the necessary auxiliary host cell proteins and transcriptional associated elements will produce an electrophoresis pattern wherein some rungs of the ladder are missing. The missing rungs will correspond to that region of the target DNA sequence which is inaccessible to the DNase I because of binding of the transactivator mediated complex.

Optimizing Candidate Inhibitors

Once the candidate inhibitors have been found that are a part of the transactivating proteins, they may be optimized for inhibition. Methods used to optimize may be any of the following.

a. Varying the length, increase at amino and carboxy termini to determine if flanking sequences affect binding (Haviv et al., *Peptides: Chemistry, Structure, and Biology* edited by J. E. Rivier and G. R. Marshall, ESCOM, Leiden, (1990), pp. 192–194). Using this data, decrease length from appropriate end to obtain smallest peptide.

b. Cyclization (Rizo and Gierasch, (1991) Ann. Rev. Biochem. 61:387–418) of optimized peptide by disulfide bond formation (O'Neil et al., (1992) Proteins 14:509–515; Rustici et al., (1993) Science 259:361–365) or other chemical means (Rodriguez et al., *Peptides: Chemistry, Structure, and Biology* edited by J. E. Rivier and G. R. Marshall, ESCOM, Leiden, (1990), pp. 108–110; Rivier et al., in *Peptides: Chemistry and Biology* edited by J. A. Smith and J. E. Rivier, ESCOM, Leiden, (1992) pp. 33–36; Ho and Dwyer in *Peptides: Chemistry and Biology* edited by J. A. Smith and J. E. Rivier, ESCOM, Leiden, (1992) pp. 511–512).

c. Random mutagenesis of coding sequences for optimized peptide in combination with the M13 monomeric expression system (Lowman et al., (1991) Biochemistry, 30:10832–10838; Bass et al., (1990) Proteins, 8:309–314).

d. An iterative chemical process of modifying individual amino acids within the optimized peptide (Ali et al., *Peptides: Chemistry, Structure, and Biology* edited by J. E. Rivier and G. R. Marshall, ESCOM, Leiden, (1990), pp. 94–96; Hashimoto et al., *Peptides: Chemistry, Structure, and Biology* edited by J. E. Rivier and G. R. Marshall, ESCOM, Leiden, (1990), pp. 116–117; Chorev et al., *Peptides: Chemistry, Structure, and Biology* edited by J. E. Rivier and G. R. Marshall, ESCOM, Leiden, (1990), pp. 163–164; Bolin et al., in *Peptides: Chemistry and Biology* edited by J. A. Smith and J. E. Rivier, ESCOM, Leiden, (1992) pp. 150–151).

e. Design based upon analysis of nuclear magnetic resonance (Chen et al., (1993) Biochemistry 32:32–37; Landry and Giersch, (1991) Biochemistry 30:7359) or X-ray crystallography results (de Vos et al., (1992) Science, 255:306–312), which will provide information about the binding structure.

f. Alteration of the components of a hydrophobic peptide to make it more soluble, such as adding charged residues to the peptide or chemically modifying a portion of the peptide using skills known in the art.

Obtaining Candidate Inhibitors Derived from Auxiliary Host Cell Proteins

If a transcriptional inhibitor represents a portion of the viral transactivator Tax, then it is likely that the inhibitor binds to an auxiliary host cell protein. This interaction may or may not have deleterious effects on normal cell function. It may be useful to identify and test the "complement inhibitor" i.e. that region of the auxiliary host cell protein that interacts with the inhibitory region of the transactivator protein.

To identify the "complement inhibitor" one would first identify the auxiliary host cell protein then map the region of interaction with the viral transactivator. Identification of the auxiliary host cell protein can be carried out as described in previous sections. Mapping the site of interaction can be carried out by structural or chemical methods. For example, co-crystals of the inhibitor peptide and the auxiliary host cell protein could be isolated and analyzed by x-ray crystallography. If the peptide had too much motion to allow the structure to be resolved at sufficient resolution, then co-crystallization of the entire viral transactivator protein and the auxiliary host cell protein could be attempted, or modifications to the peptide could be made to constrain possible conformations (i.e. cyclization).

Alternatively, deletions of the auxiliary host cell protein could be made and analyzed for their ability to interact with the inhibitory peptide or with the native Tax protein. These deletions could be made relatively easily if the auxiliary protein was cloned in an *E. coli* expression vector. A similar approach would be to subject the auxiliary host cell protein to proteolysis, analyze the fragments for the ability to interact with the peptide or with the native Tax protein, and sequence the fragment that interacts. One pitfall in interpreting these results is that a deletion mutant or proteolytic fragment may adopt a conformation that is not recognized by the inhibitor, and would be scored incorrectly.

A third approach would be to allow the peptide to bind to the auxiliary host cell protein, treat with various chemical modification reagents (e.g., NEM, Iodine, alkylation reagents and others as reviewed by Glazer, *The Proteins* 3rd Ed. Vol. II, Neurath and Hill (eds) Academic Press, New York (1976) pp. 1–103), protealize and analyze the auxiliary protein by mass spectrometry for regions that were protected from modification.

To determine the binding region on auxiliary host cell proteins after a fragment derived from the transactivating protein has been found to be inhibitory, the auxiliary host cell proteins can be analyzed further using electrophoresis mobility shift assays (EMSA). The EMSA would provide valuable information about which auxiliary host cell proteins are the target of the transactivating protein. In addition to screening random pools of peptides, we will focus on identifying the host cell target of Tax, and the interaction domains of Tax and the host cell protein. This approach may lead to the development of specific inhibitors. For example, since Tax does not interact specifically with promoter DNA and does not require protein synthesis to activate transcription, it is probable that Tax activates transcription through protein-protein interactions with auxiliary host cell proteins. These interactions could be transient or long lasting. If these interactions are long lasting, then the candidate inhibitors of the present invention would inhibit them.

It is likely that Tax, for example, interacts with members of the ATF/CREB transcription factor family. In addition, Tax may interact with the general transcription elements associated with RNAP II (e.g., TATA binding factor of TFIID). One method to quickly identify potential candidates would be to resolve crude nuclear extracts or partially purified preparations of specific transcription factors using SDS-PAGE, transfer to nitrocellulose, and probe for Tax interactions using radiolabelled Tax, or sandwich blots with Tax followed by an anti-Tax antibody. Interaction with Tax could not be ruled out on the basis of a negative result with these experiments, since Tax may not recognize the denatured protein, or may recognize only protein-protein complexes (e.g., ATF-CREB heterodimers) or protein DNA complexes. To control for these possibilities, dot blot experiments could be performed. Various proteins alone, in heteromeric combinations, and in the presence of DNA could be incubated in solution, spotted on nitrocellulose, and probed with Tax.

Coimmunoprecipitations would be another way to examine Tax-host cell protein interactions. It is possible that the interaction may not be stable throughout the immunoprecipitation procedure. A similar experiment would be to make a Tax column, either by coupling the Tax protein directly to a solid support, or coupling through an immobilized antiTax antibody or using GST Tax fusion protein and glutathione agarose beads. Crude extracts or partially purified preparations of host cell proteins could be put over the column, and the species retained could be compared with those in the effluent.

Some experimental evidence suggests localization of Tax at the promoter is important for its activity since a Gal4-Tax fusion protein activated transcription from a promoter containing Gal4 sites (Fuji et al., (1991) Oncogene 6:2349–2352; Fujisawa et al., (1991) J. Virol. 65:4525–4528). In addition, Matthews (1992, Ph.D. Thesis, University of Colorado, Boulder, Colo.) has shown that Tax remained associated with templates in an in vitro transcription reaction after unbound proteins were removed by washing, consistent with a role in transcription. These experiments were performed using immobilized templates as originally described by Arias and Dynan, (1989) J. Biol. Chem. 264:2021–2033. If one assumes that Tax acts while present in the transcription complex, rather than transiently on a component that may or may not be present in the transcription complex, then it ought to be possible to enrich for candidate host cell proteins by isolating transcription complexes on a preparative scale using the immobilized template system or using gel filtration chromatography and free template.

Production of Inhibitors

The inhibitors of the present invention can be produced in a number of ways that are known to those of skill in the art. The method of production depends on economies of various methods as well as the contemplated mode of administration. Peptide synthesis is a well known method, particularly for peptides that are reasonably short (Merrifield, (1986) Science 232:343–347; Kent, (1988) Ann. Rev. Biochem. 57:957–989; G. T. Young in *Chemical Synthesis and Sequencing Peptides and Proteins*, T. Liu, A. Schechter, R. Heinrickson and P. Condliffe (eds.), Elsevier North Holland Inc., New York, 1981). It will be appreciated by those of skill in the art that knowledge of the amino acid sequence of a peptide allows the design of DNA that will code for its expression in a particular host.

The expression of DNA that encodes inhibitors of transactivators can be carried out in a wide variety of cell types. The expression DNA that encodes inhibitors of the present invention can be carried out in a wide variety of cell types. Procaryotes most frequently are represented by various strains of *E. coli*. However, other microbial strains may also be used, such as bacilli, for example, *Bacillus subtilis*, various species of Pseudomonas, or other bacterial strains. In such procaryotic systems, plasmid vectors which contain replication sites and control sequences derived from a species compatible with the host are used. For example, *E. coli* is typically transformed using derivatives of pBR322, a plasmid derived from an *E. coli* species by Bolivar et al., (1977) Gene 2:95. pBR322 contains genes for ampicillin and tetracycline resistance, and thus provides additional markers which can be either retained or destroyed in constructing the desired vector. Commonly used procaryotic control sequences, which are defined herein to include promoters for transcription initiation, optionally with an operator, along with ribosome binding site sequences, include such commonly used promoters as the beta-lactamase (penicillinase) and lactose (lac) promoter systems (Chang et al., (1977) Nature 198:1056), the tryptophan (trp) promoter system (Goeddel et al., (1980) Nucleic Acids Res. 8:4057) and the lambda derived $P_L$ promoter (Shimatake et al., (1981) Nature 292:128), and N-gene ribosome binding site, which has been made useful as a portable control cassette, U.S. Pat. No. 4,711,845, issued Dec. 8, 1987, which comprises a first DNA sequence that is the $P_L$ promoter operably linked to a second DNA sequence corresponding to the $N_{RBS}$ upstream of a third DNA sequence having at least one restriction site that permits cleavage within 6 bp 3' of the $N_{RBS}$ sequence. U.S. Pat. No. 4,666,848 issued May 19, 1987 discloses additional vectors with enhanced expression capabilities. Also useful is the phosphatase A (phoA) system described by Chang et al., in European Patent Publication No. 196,864, published Oct. 8, 1986. However, any available promoter system compatible with procaryotes can be used.

In addition to bacteria, eukaryotic microbes, such as yeast, may also be used as hosts. Laboratory strains of *Saccharomyces cerevisiae*, Baker's yeast, are most used, although a number of other strains are commonly available. While vectors employing the 2 micron origin of replication are illustrated (Broach, (1983) Meth. Enzymol. 101:307; U.S. Pat. No. 4,803,164), other plasmid vectors suitable for yeast expression are known (see, for example, Stinchcomb et al., (1979) Nature 282:39, Tschempe et al., (1980) Gene 10:157 and Clarke et al., (1983) Meth. Enzymol. 101:300). Control sequences for yeast vectors include promoters for the synthesis of glycolytic enzymes (Hess et al., (1968) J. Adv. Enzyme. Req. 7:149; Holland et al., (1978) Biochemistry 17:4900).

Additional promoters useful in yeast host microorganisms and known in the art include the promoter for 3-phosphoglycerate kinase (Hitzeman et al., (1980) J. Biol. Chem. 255:2073), and those for other glycolytic enzymes, such as glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. Other promoters, which have the additional advantage of transcription controlled by growth conditions, are the promoter regions for alcohol dehydrogenase 2, isocytochrome C, acid phosphatase, degradative enzymes associated with nitrogen metabolism, and enzymes responsible for maltose and galactose utilization (Holland et al., (1978) Biochemistry 17:4900).

It is also believed that terminator sequences are desirable at the 3' end of the coding sequences. Such terminators are found in the 3' untranslated region following the coding sequences in yeast-derived genes. Many of the vectors illustrated contain control sequences derived from the enolase gene containing plasmid peno46 (Holland et al., J. Biol. Chem. 256:1385) or the LEU2 gene obtained from YEp13 (Broach et al., (1978) Gene 8:121); however, any vector containing a yeast compatible promoter, origin of replication and other control sequences is suitable.

It would be possible to express the inhibitors of the present invention in eukaryotic host cell cultures derived from multicellular organisms. See, for example, *Tissue Culture* Academic Press, Cruz and Patterson, editors (1973). Useful host cell lines include murine myelomas N51, VERO and HeLa cells, and Chinese hamster ovary (CHO) cells. Expression vectors for such cells ordinarily include promoters and control sequences compatible with mammalian cells such as, for example, the commonly used early and late promoters from Simian Virus 40 (SV40) (Fiers et al., (1978) Nature, 273:113) or viral promoters such as those derived from polyoma, Adenovirus 2, bovine papilloma virus, or avian sarcoma viruses, or immunoglobulin promoters and heat shock promoters. A system for expressing DNA in mammalian systems using the BPV as a vector is disclosed in U.S. Pat. No. 4,419,466. A modification of this system is described in U.S. Pat. No. 4,601,978. General aspects of mammalian cell host system transformations have been described by Axel in U.S. Pat. No. 4,399,216 issued Aug. 16, 1983. Also useful is gene amplification in eukaryotic cells as described by Ringold in U.S. Pat. No. 4,656,134, issued Apr. 7, 1987. It now appears also that "enhancer" regions are important in optimizing expression; these are, generally, sequences found upstream of the promoter region. Origins of replication may be obtained, if needed, from viral sources. However, integration into the chromosome is a common mechanism for DNA replication in eukaryotes.

Plant cells are also now available as hosts, and control sequences compatible with plant cells such as the nopaline synthase promoter and polyadenylation signal sequences (Depicker et al., (1982), J. Mol. Appl. Gen.1:561) are available. Additionally, methods and vectors for transformation of plant cells have been disclosed in PCT Publication No. WO 85/04899, published Nov. 7, 1985.

Host strains typically used in cloning, expression and sequencing of recombinant constructs are as follows. For cloning, sequencing, and for expression of construction under control of most bacterial promoters, *E. coli* strain MM294 obtained form *E. coli* Genetic Stock Center GCSC#6135, may be used as the host. For expression under control of the $P_LN_{RBS}$ promoter, *E. coli* strain K12MC10001 lysogen, $N_7N_{53}cI857$ $SusP_{80}$, a strain deposited with the American Type Culture Collection (ATCC 39531), may be used. *E. coli* DG116, which was deposited with the ATCC (ATCC 53606) on Apr. 7, 1987, may also be used.

For M13 phage recombinant, *E. coli* strains susceptible to phage infection, such as *E. coli* K12 strain DG98, are employed. The DG98 strain has been deposited with ATCC (ATCC No. 39768) on Jul. 13, 1984.

Mammalian expression has been accomplished in COS-A2 cells and also can be accomplished in COS-7, and CV-1, hamster and murine cells. Insect cell-based expression can be in *Spodoptera fruigiperda*.

Since viral transcription occurs within a host cell (e.g., helper T-cells in the case of HTLV-I) potential inhibitors of transcription must enter the cell if produced outside the host cell. Additionally, they may need to enter the nucleus for inhibition of transcription to occur. In order to improve movement of an inhibitor into the cell and nucleus, it may be preferable to produce the inhibitors in a form that encourages internalization. A form that encourages internalization is to combine the inhibitor with a moiety that will enhance internalization of the moiety and/or the inhibitor to which it is attached. A number of methods can be used to accomplish this.

First, the inhibitor can be attached to an internalizing monoclonal antibody specific for the a protein that is internalized by the host cell. For example, the anti-CD3 antibody 64.1 undergoes receptor mediated endocytosis into $CD4^+T$ cells (Press et al., (1988) Cancer Res. 48:2249–2257). IL-2 is also known to be susceptible to receptor mediated endocytosis (Waters et al., (1990) Eur. J. Immunol. 20:785; Weissman et al., (1986) Proc. Nat. Acad. Sci. USA 83:1436; Fujii et al., J. Exp. Med. (1986) 163:550) and thus the inhibitor could be fused to IL-2 or included in the sequence of IL-2 such that it is on the surface in its native conformation, or chemically attached to IL-2. Second, the inhibitors of the present invention can be attached to or included in a viral vector specific for the host cell. An example would be an engineered version of HTLV-I, minus one or more proteins essential for successful infection or replication in the T-cell host. To improve infection of T-cells, it might be possible to use viruses for which the receptor is the MHC class II protein itself since most T-cells have MHC-class II proteins on their surface membranes. Such an MHC class II virus would be LDH viruses (Inada and Mims, (1984) Nature 309:59). Third, the inhibitor can be attached to a generic internalizing agent if the appropriate specificity can be obtained for the host cell. Such agents might include anti-transferrin antibodies or the vaccinia virus 14 kD protein derived from its N-terminus (Esteban et al., (1990) Virology 178:81). Examples of transferrin receptor related internalizing sequences are the generic sequences Tyr-Xaa-Arg-Phe (Seq. I.D. No. 38) and Phe-Xaa-Arg-Phe (Seq. I.D. No. 39), wherein Xaa is variable. Numerous examples of this and similar sequences are listed in (1990) Cell 63:1061. An example of a potential genetic internalizing peptide is a fragment of poly(L-lysine) ((1990) Bioconjugate Chemistry 1:149). Fourth, the inhibitors of the present invention can be fused to a protein or peptide that binds specifically to the host cell. For example CD4 is known to be internalized into the T-cell upon its activation (Shih et al., (1990) EMBO J. 9:425); thus inhibitors would be fused to proteins or their fragments which bind CD-4, such as the HIV gp120 protein or its fragments. Alternatively, the inhibitor can be fused to a peptide that binds tightly to the internalized peptide. Such tight binding peptides could be obtained in the same manner as the inhibitors of the present invention. Fifth, the inhibitor of the present invention can be fused to known nuclear localizing peptides. Several examples of these nuclear localizing peptides are discussed in (1986) Annual Rev. Cell Biol. 2:367.

The production of conjugates or fusion peptides that have improved internalization characteristics can be made as one single peptide using an appropriately designed gene or synthesis procedure. Alternatively, the inhibitor peptide can be synthesized or recombinantly produced separately from the internalization enhancer and then attached through chemical covalent bonds or combined in a mixture to allow hydrohobic or other non-covalent bonds to occur.

Purification of Inhibitors

Purification of the inhibitors of the present invention after peptide synthesis or recombinant production can be accomplished by methods that are known in the art.

Obtention of Inhibitor of Hepatitis B Protein X (Protein pX)

The human hepatits B virus (HBV) genome encodes a transactivator protein pX that could be functionally similar to the HTLV-I Tax protein although they are not similar in sequence. Transactivation of both viral promoters probably occurs through CRE like elements (HTLV-I 21 bp repeat, HBV XRE). Factor and Shaul (Oncogene (1990) 5:867–872) showed that Tax can transactivate the HBV promoter, that both Tax and pX can transactivate promoters containing NF-κB binding sites, and that both are effective in similar concentration ranges. MaGuire et al. ((1991) Science 252:842–844) reported that HBV X protein increases the binding of CREB and ATF-2 to HBV promoter sequences. These observations suggest that pX and Tax activate transcription through a similar mechanism and perhaps through the same transcription factors. It is possible that we can test this by screening Tax inhibitors for the ability to inhibit pX activity by in vitro transcription and EMSA. Rather than lymphocyte extracts, hepatocyte extracts will be used (HepG2, Dinter et al., (1987) EMBO 6:567–613). Recombinant pX can be expressed in pET8C-hbx (Wu et al., (1990) Cell 63:687–695) and purified. An oligonucleotide containing the XRE 5'-GTGTTTGCTGACGCAACCCCAC-3' (Seq. I.D. No. 40) and recombinant ATF and CREB proteins as described herein can be used in the EMSA. The core promoter sequences of HBV (nt1466–1987; Roossinck et al. 1986 MCB 6:1393–1400) can be used in the in vitro transcription assays.

Pharmaceutical Administration of Inhibitors of Transactivation

Also contemplated by the present invention are pharmaceutical compositions comprising therapeutically effective amounts of polypeptide products of the invention together with one or more suitable additives. Suitable additives include diluents, preservatives, solubilizers, emulsifiers, adjuvants and/or carriers useful in the inhibitor therapy. A "therapeutically effective amount" as used herein refers to that amount which provides a therapeutic effect for a given condition and administration regimen. Such compositions are liquids or lypholized or otherwise dried formulations and include diluents of various buffer content (e.g., Tris-HCl, acetate, phosphate), pH and ionic strength, additives such as albumin or gelatin to prevent adsorption to surfaces, detergents (e.g., Tween 20, Tween 80, Pluronic F68, bile add salts), solubilizing agents (e.g., glycerol, polyethylene glycol), anti-oxidants (e.g., ascorbic add, sodium metabisulfite), preservatives (e.g., Thimerosal, benzyl alcohol, parabens), bulking substances or tonicity modifiers (e.g., lactose, mannitol), covalent attachment of polyethylene glycol to the protein (e.g., Davis, U.S. Pat. No. 4,179, 337, issued Dec. 18, 1979 and WO 91/07189, published May 30, 1991), complexation with metal ions, or incorporation of the material into or onto particulate preparations or polymeric compounds such as polylactic acid, polyglycolic acid, hydrogels, etc. or into liposomes, microemulsions, micelles, unilamellar or multilamellar vesicles, erythrocyte ghosts, spheroblasts or recombinant hemoglobin carriers (PCT/US92/09713, filed Nov. 6, 1992)

The inhibitors of the present invention are useful for inhibiting transcription of DNA that codes for proteins that can be deleterious to mammals, particularly humans. The DNA transcription that is inhibited is DNA that is up regulated by transactivating factors. The inhibited DNA includes, but is not limited to, DNA that may be an important element of viral infection or the onset of cell proliferation associated with many cancers.

There are a group of disorders that are characterized by onset resulting from up regulation or down regulation of DNA by transactivating factors. Many diseases, particularly those associated with viral infections, have a manifestation of the disease state after a period of dormancy beginning with the infection by the virus. These periods of latency or dormancy can be anywhere from days to years.

An example of cells with a genetic defect is patients with homozygous familial hypocholesterolemia. These patients exhibit inordinately high levels of plasma cholesterol and LDLs that can lead to atherosclerosis. The molecular mechanism underlying this condition is that patients are unable to suppress the activity of HMG-CoA-reductase, the rate-limiting enzyme for cholesterol synthesis. This invention could down regulate transcription of the gene encoding HMG-CoA-reductase.

Examples of viral targets include the Human T-cell Leukemia Virus I (HTLV-I) and the Hepatitis B Virus (HBV). Both of these viruses contain transactivating proteins (Tax and pX respectively) that regulate transcription of their viral genomes and also several genes with in the host cell genome. In the case of HTLV-I, regulation of gene expression by Tax can lead to the development of Adult T cell Leukemia (ATL) or a neuromuscular disorder HTLV-I associated myelopathy or tropical spastic paraparesis (HAM/TSP). In the case of HBV, regulation of gene expression by pX can lead to the development of hepatocarcinoma. Those who become infected with the HIV virus (human immunodeficiency virus) often do not manifest the associated disease state of acquired immune deficiency syndrome (AIDS) for five to fifteen years.

The inhibitors and pharmaceutical compositions of the present invention can be administered in any number of conventional dosage forms. Intravenous bolus injection or intravenous infusion over a given period are preferred routes of administration. Given the long latency period before manifestation of the disease state in many diseases to be treated with the inhibitors of the present invention, a particularly suitable method of administration is gene therapy, the techniques of which are known to those of skill in the art. The tissues in the organ or tissue that is the likely target of a particular disease state can be transfected (Birinyl et al., WO 9207943: Hewitt et al., WO 9207080; Anderson et al., WO 9006997; Dank et al., WO 8907150) with an appropriate gene to produce the inhibitor. Alternatively, hematopoietic stem cells can be obtained (Tsukamoto et al, U.S. Pat. No. 5,061,620; Locken and Terstappen, European Patent Application 455482; Boyse et al., WO 8904168; Goffe et al., WO 9116116) and transformed ex vivo with the inhibitor gene and then reinfused into the patient (Zsebo et al., WO 9105795; Clarke et al., WO 9211355).

An added aspect of gene therapy that is contemplated by the present invention is gene therapy that has the ability to be regulated. Such a method of regulating gene therapy in a mammal comprises introducing into the genetic material of said mammal a gene, said gene comprising:

a) one or more coding region for an inhibitor that inhibits a biological activity of a first non-naturally occurring biological factor; and
b) a regulatory region that is activated by a second non-naturally occurring biological factor.

The first and second non-naturally occurring biological factor may or may not be the same. If they are the same, then the presence of the non-naturally occurring biological factor would activate a gene that would produce a peptide that in turn inhibits a biological activity of the non-naturally occurring biological factor. In this way, the appearance of the non-naturally occurring biological factor could lead to the destruction of a deleterious effect it might have. In the case of viral transactivating factors, such as Tax, the presence of the transactivating factor, such as Tax, would activate the gene therapy mechanism by activating the transcription and production an inhibitor to deleterious effects of the transactivating factor, such as Tax transactivation and onset of HTLV-L.

If the first non-naturally occurring biological factor and the second non-naturally occurring biological factor are different, there would be the opportunity to regulate the inhibition of the first non-naturally occurring biological factor by administration of the second non-naturally occurring biological factor. Such administration could be by any of the means described above for administering the inhibitors of the present invention.

The coding region used in the regulated gene therapy can be the coding region for any of the inhibitors that are the subject of the present invention. The non-naturally occurring biological factors are as defined herein and preferably are transactivating factors, more preferably viral transactivating factors. The regulatory regions that can be activated by such non-naturally occurring biological factors are those that are known in the art or those that can be identified during the identification of the inhibitors that are the subject of the present invention.

All references cited herein are hereby incorporated by reference for their relevant teachings

EXAMPLES

The following examples are provided by way of describing specific embodiments of the present invention without intending to limit the scope of the invention in any way.

Example 1

Synthesis of Tax Protein Fragments

Chemically synthesize a series of overlapping peptides spanning the entire Tax protein sequence (Seiki et al. (1985), Science 228:1532–1534). Each peptide will be 20 amino acids in length and overlap with the previous peptide by 8 amino acids.

The following is a list of preferred peptides that are synthesized beginning at the amino terminus wherein the accepted one letter designation for amino acids is used (I.D. Seq. Nos. 1 through 29, respectively).

```
MAHFPGFGQSLLFGYPVYVF
            FGYPVYVFGDCVQGDWCPIS
                        QGDWCPISGGLCSARLHRHA
                                    SARLHRHALLATCPEHQITW

CPEHQITWDPIDGRVIGSAL
            GRVIGSALQFLIPRLPSEPT
                        PRLPSFPTQRTSKTLKVLTP
                                    KTLKVLTPPITHTTPNIPPS

TTPNIPPSFLQAMRKYSPFR
            MRKYSPFRNGYMEPTLGQHL
                        EPTLGQHLPTLSFPDPGLRP
                                    FPDPGLRPQNLYTLWGGSVV

TLWGGSVVCMYLYQLSPPIT
            YQLSPPITWPLLPHVIFCHP
                        PHVIFCHPGQLGAFLTNVPY
                                    AFLTNVPYKRIEELLYKISL

ELLYKISLTTGALIILPEDC
            LIILPEDCLPTTLFQPARAP
                        LFQPARAPVTLTAWQNGLLP
                                    AWQNGLLPFHSTLTTPGLIW

LTTPGLIWTFTDGTPMISGP
            GTPMISGPCPKDGQPSLVLQ
                        GQPSLVLQSSSFIFHKFQTK
                                    IFHKFQTKAYHPSFLLSHGL
                                                SFLLSHGLIQYSSFHSLHLL

SFHSLHLLFEEYTNIPISLL
            TNIPISLLFNEKEADDNDHE
                        EADDNDHEPQISPGGLEPPS

PGGLEPPSEKHFREIEV
```

Additional peptides are synthesized as follows, wherein the accepted one letter designation for amino acids is used.

| | |
|---|---|
| SFHSLHLLFEEYTNIPISLL | (Seq. I.D. No. 26) |
| SFHSLHLLFE | (Seq. I.D. No. 48) |
| HSLHLLFEEY | (Seq. I.D. No. 49) |
| SFHSLHLLFEEE | (Seq. I.D. No. 54) |
| EEGGSFHSLHLLFE | (Seq. I.D. No. 55) |
| EEGGSFHSLHLLFEEE | (Seq. I.D. No. 56) |
| DPIDGRVIGSALQFL | (Seq. I.D. No. 30) |
| KAYHPSFLLSHGLIQ | (Seq. I.D. No. 31) |
| FNEKEADDNDHEPQI | (Seq. I.D. No. 32) |

-continued

| | |
|---|---|
| LHLLFEEYTN | (Seq. I.D. No. 50) |
| LLFEEYTNIP | (Seq. I.D. No. 51) |
| EYTNIPISLL | (Seq. I.D. No. 52) |
| IPISLLFNEK | (Seq. I.D. No. 53) |
| FLSEFLHSHL | (Seq. I.D. No. 57) |

Example 2

In Vitro Screen of Peptides Using Nuclear Extracts, Run-off Transcription and EMSA Tax activates transcription in a cell free assay (Matthews et. al., (1992) Mol. Cell. Biol. 12:1986–1996) and Tax alters auxiliary host cell protein-DNA interactions in an electrophorectic mobility shift assay (EMSA) (Matthews et. al., (1992) Mol. Cell. Biol. 12:1986–1996; Zhao and Giam, (1991) Proc. Nat. Acad. Sci. USA 88:11445–11449). Candidate inhibitor peptides such as the peptides described in Example 1 are tested for the ability to abrogate the effect of Tax using both of these assays. In vitro transcription minimally requires RNA polymerase and at least seven associated general factors. Tax transactivation of in vitro transcription also likely requires additional auxiliary host cell proteins. Run off transcription assays are performed using nuclear extracts or partially fractionated host cell proteins.

a. In vitro Transcription Assay

The peptides listed in Example 1 are screened in a run off in vitro transcription assay (Matthews et. al., (1992) Mol. Cell. Biol. 12:1986–1996 for the ability to inhibit Tax mediated activation of transcription. This assay is performed with nuclear extracts which contain RNA polymerase II and its associated general factors as well as numerous sequence specific DNA binding proteins known to activate transcription. In contrast to the assay with cultured cells described below (Example 4), this screen will not be biased toward peptides that enter the cell and the nucleus more efficiently.

The cellular target of the Tax protein is unknown. Some cellular genes are transactivated by Tax through CREs and NF-κB binding sites present in their promoters. Genetic and biochemical analyses suggest one target in the HTLV-I promoter is a 21 bp repeat binding protein. Other sequences such as the TATAA box and initiator element where general transcription factors assemble, and the Sp1 and c-myc binding sites may also be important. The three 21 bp repeats in the HTLV-I promoter are similar to the consensus sequence of the cyclic AMP response element (CRE) and a family of proteins is known to bind to this sequence in various homomeric and heteromeric combinations. By carrying out the initial screen in crude extracts all possible combinations are allowed and relevant concentrations of competing proteins are present. When a candidate inhibitor peptide is identified it will be immobilized on a solid support and used as an affinity column to isolate the protein or protein complex targeted by Tax. The peptide may also be labelled (radio or photo) and used as a probe with nuclear extracts or partially purified proteins separated by SDS-PAGE and transferred to nitrocellulose Lymphocyte cell culture and preparation of transcription extracts. CEM T lymphocytes (Slamon et al., (1985) Science 228:1427–1430) and CEM T lymphocytes stably transfected with an inducible Tax-expressing plasmid, CEM Tax (Nyborg, Colorado State University, Fort Collins, Colo.) are grown in spinner culture at 37° C. using Iscove's medium supplemented with 5% fetal bovine serum, 5% calf serum, and glutamine. HTLV-I infected, Tax-expressing SLB-I cells (Koeffler et al., (1984) Blood 64:482–490) and HUT 102 cells (Advanced Biotechnologies, Inc., Columbia Md., ATCC Accession Number TIB 162) are grown in T-150 flasks at 37° C. using the same medium. Nuclear extracts are prepared as described below (adapted from Dynan, (1987) Genetic Engineering: Principles and Methods, Plenum Publishing, New York). Cells are harvested by centrifugation and washed with phosphate buffered saline. All buffers contain 1 μg/ml of the protease inhibitors phenylmethylsulfonyl fluoride, leupeptin, aprotinin, and soybean trypsin inhibitor. The cell pellet is resuspended in 4 packed cell volumes (PCV) of hypotonic lysis buffer (10 mM Tris, pH 7.9, 10 mM KCl, 1.5 mM $MgCl_2$, 1 mM DTT) and incubated on ice 10 min. The cell suspension is homogenized, nuclei are pelleted by centrifugation and washed with 2 PCV of hypotonic lysis buffer. Isolated nuclei are resuspended in 4 PCV of nuclear extraction buffer (0.05M Tris-HCl pH 7.9, 0.42M KCl, 0.005M $MgCl_2$, 0.001M EDTA, 0.002M dithiothreitol (DTT), 20% (v/v) glycerol, 10% (v/v) sucrose), stirred on ice for 60 min. and centrifuged for 30 min. at 17,000 rpm in a Dupont Sorvall SS-34 fixed angle rotor. 0.33 g/ml ammonium sulfate is added to the supernatant and stirred for 60 min. on ice. Precipitated proteins from HSS are pelleted by centrifugation for 10 min. at 15,000 rpm in the SS-34 rotor, resuspended in 0.05 HSS volumes of TM buffer (0.050M Tris-HCl pH 7.9, 0.0125M $MgCl_2$, 0.001M EDTA, 0.001M DTT, 20% (v/v) glycerol) containing 0.1M KCl, dialyzed against the same buffer overnight, and frozen at −70° C.

In Vitro Transcription Assays. Templates used for run off in vitro transcription assays are prepared by excising the appropriate promoter (e.g., the HTLV-I LTR from −353 to +137 relative to the RNA start site) containing DNA from plasmid DNA using restriction enzymes then isolating the DNA using preparative PAGE. The templates can be either immobilized or in solution when they are exposed to the other components of the transcription assay.

Immobilized templates are prepared by coupling streptavidin-agarose beads to a biotinylated nucleotide incorporated at the upstream end of the promoter as described previously (Arias and Dynan, (1989) J. Biol. Chem. 264:2021–2033). For experiments performed with immobilized template, preinitiation transcription complexes are formed in the presence of 300–500 ng of immobilized template, 50–400 μg nuclear extract, relative amounts of candidate inhibitors as described below, and TX buffer (25 mM Tris-HCl pH 7.9, 6.25 mM $MgCl_2$, 0.5 mM EDTA, 0.5 mM DTT, 50 mM KCl, and 10% (v/v) glycerol) in a 50 μl reaction at 30° C. for 60 min. Immobilized templates are then washed 3 times with 1 ml TX buffer and resuspended in 50 μl of TX buffer. RNA synthesis is initiated by the addition of 250 μM each of ATP, CTP, GTP, 12.5 μM UTP and 0.067 μM [α-$^{32}$P] UTP (3000 Ci/mmol). Reactions are terminated and RNA transcripts are isolated and analyzed by urea-PAGE. Relative amounts of RNA are quantitated using a Molecular Dynamics Phosphor Imager.

The amount of inhibitor added depends on the the degree of inhibition it possesses. A typical range of inhibitor is from equimolar to 1000 fold molar excess with respect to the transcription factor it is trying to outcompete. For example, assume 0.5 μg of purified Tax protein is needed to observe measurable activation of transcription (0.5 μg of a 40 kDa protein in a 50 μl reaction represents 0.25 μM total protein). In this case peptides representing portions of the Tax protein are added at 0.25–250 μM final and their effects would be measured. If the amount of transcription factor present in the extract is unknown (as is the case for the relative amounts of most of the transcription factors in the extract) and random peptides are being screened, then 2.5 to 1000 µM of each peptide will be included in the reaction. This amount varies depending on the number of peptides in the pool and their solubility. For example a pool of 40 peptides may be quite soluble at 25 µM each while a pool of 400 each at 25 µM peptides would result in a total protein concentration above the solubility threshold for several of the component peptides in the mixture. The 2.5 to 25 µM peptide concentration represents a 10 to 100 fold molar excess if one assumes that 50 µg of nuclear extract is used, each transcription factor represents 0.01 to 0.1 percent of the total nuclear protein and has an average MW of 40 kDa.

In the case of using peptides representing a portion of the Tax to compete with Tax for interaction with host cell proteins it is desirable to minimize the amount of Tax required in a reaction. This is defined by titrating addition of purified recombinant Tax to extracts lacking Tax and determining the minimum amount required to measure transcriptional activation. Alternatively, this is achieved by preparing extracts from an inducible Tax expressing cell line (such as CEMTax, metallothionein promoter, cadmium inducible) and regulating the amount of induction.

In vitro transcription reactions are also performed using templates in solution. Promoter fragments are isolated as above but are not biotinylated. Preinitiation complexes are formed in the presence of 50–250 ng DNA template, 50–250 µg nuclear extract, pools of candidate inhibitors, and TX buffer in a 50 µl reaction at 30° C. for 5–60 min. RNA synthesis is initiated by the addition of 250 µM each of ATP, CTP, GTP, 12.5 µM UTP and 0.067 µM [$\alpha$-$^{32}$P] UTP (3000 Ci/mmol). Reactions are incubated for 2–15 min. at 30° C., and RNA is isolated and analyzed by urea-PAGE as above. Relative amounts of RNA are quantitated using a Molecular Dynamics Phosphor Imager.

Thirty peptides representing portions of the native Tax protein are added individually at 200 µM final concentration to in vitro transcription reaction containing the HTLV-I LTR template and CEMTax extract, the HTLV-I LTR template and CEM extract, the RSV LTR template and CEMTax extract, the RSV LTR template and CEM extract (75 ng of template per reaction, 200 ng extract per reaction). Reactions are incubated for 15 min. at 30° C., nucleoside triphospates were added, reactions are incubated an additional 5 min at 30° C. then terminated. RNA is isolated and analyzed by urea-Page and Phosphor Image Analysis (Molecular Dynamics, Inc). Those peptides that decrease or abolish transcription only in reactions containing the HTLV-I and not the RSV template are analyzed further.

For example, let us assume peptide X decreased transcription in the HTLV-I template CEMTax extract five fold and had no effect in the other template extract combinations. The fold molar excess of inhibitor required to abolish Tax transactivation (reduce transcription in reactions containing Tax to the level in reactions lacking Tax) is determined by adding 200 nM final concentration purified recombinant Tax to transcription reactions containing the HTLV-I template and CEM extract. Peptide X is added to individual reactions at 0, 0.2, 2, 10, 25, 50, 100, 200 µM final concentration.

To determine the auxiliary host cell protein-Tax interaction disrupted by peptide X, transcription complexes formed (30° C. 60 min) in the CEMTax extract (20 ug) with the HTLV-I template (7.5 ug) are isolated from free protein in the extract by gel filtration chromatography. Then bound proteins are eluted from the template with 1M NaCl and probed with peptide X (either by affinity chromatography with peptide X immobilized or by for western blotting with radiolabelled peptide X).

b. EMSA Gel Shift Assay

In the case of Tax, several different effects may be observed when Tax is present in an EMSA reaction. One effect is an increase in amount of protein-DNA complex formed. For example, Matthews et al. ((1992) Mol. Cell. Biol. 12:1986–1996) reported that 21 bp repeat binding proteins purified from lymphocytes shifted the mobility of an oligonucleotide containing the 21 bp repeat sequence. When Tax was included in the reaction an increase in the amount of shifted complex rather than a novel "supershifted" (more slowly migrating complex) was detected. One might suggest that Tax transactivates transcription by loading auxiliary host cell transcription factors onto their target DNA sequences. Alternatively, one might suggest that Tax transactivates transcription by binding to its target DNA indirectly through the auxiliary host cell proteins, but that this interaction is not stable to electrophoresis. Thus an apparent increase in auxiliary host cell protein-DNA complexes is observed rather than a novel complex between Tax-auxiliary host cell protein-DNA. Regardless of which mechanism is correct candidate inhibitors are screened under these experimental conditions. Candidate inhibitors are added to the binding reactions. Peptides that caused the amount of complex formed in the presence of Tax to decrease to the amount of complex formed in the absence of Tax and also peptides that abolished complex formation are then tested in in vitro and in vivo transcription assays. It is possible that a peptide may instead increase the amount of complex formed or result in a novel complex containing Tax. Although this peptide would presumably activate rather than inhibit transactivation by Tax, further characterization of the peptide and factors it interacts with may help to identify the auxiliary host cell protein required for Tax transactivation.

Another effect of Tax in EMSA reactions has been reported by Zhao and Giam ((1991) Proc. Nat. Acad. Sci. 88:11445–11449). These EMSA binding reactions contained and oligonucleotide probe with two copies of the 21 bp repeat target DNA sequence and unfractionated extracts from Jurkat T-lymphocytes. Addition of Tax to the binding reactions resulted in a novel supershifted complex. Candidate inhibitors also are screened under these experimental conditions. Those peptides that abolish the supershift or abolish all protein-DNA interactions are further characterized.

The different experimental observations described above, (increased complex versus novel complex) may reflect a requirement for two target DNA sequence or a crude protein preparation containing cofactors for Tax to stably interact with its target DNA sequence. If several auxiliary host cell proteins (e.g., cofactor and DNA binding protein) are required for Tax to stably bind to its target sequence then a candidate inhibitor of transactivation will be that portion of the auxiliary host cell cofactor that interacts with Tax.

Electrophoretic mobility shift assay. Binding reactions contain 0.1–0.5 nM [$^{32}$P]end-labelled double stranded oligonucleotide or recombinant DNA fragments (30–200 bp), 10–1000 ng poly (dI-dC) (an alternating copolymer used to compete with the labelled DNA probe for non-specific DNA binding proteins), 25 mM Tris-HCl pH 7.9, 6.25 mM MgCl$_2$, 0.5 mM EDTA, 0.5 mM DTT, 60–120 mM KCl, and 10% (v/v) glycerol in a 30 µl reaction volume. A lower amount of 10–200 ng poly (dI-dC) is used in reactions containing relatively purified protein preparations and higher amounts are used with crude protein fractions, especially nuclear extracts that contain a number of different DNA binding proteins. Some reactions also contain purified recombinant host cell proteins, Tax protein and candidate peptide inhibitors. Reactions are incubated from 4° C. to 37° C. for 5–60 min. usually 15 min. and analyzed on 5% non-denaturing polyacrylamide gels (49:1, acrylamide:N,N-methylene bisacrylamide). The electrophoresis buffer contains 0.04M Tris, 0.306M glycine, pH 8.5, and 0.1% Nonidet P-40. Gels are dried and autoradiographed, and relative amounts of protein-DNA complexes are calculated using Phosphor Image Analysis.

DNA oligonucleotide and fragment probe sequences. The nucleotide sequence of the top strands of the oligonucleotides are listed below. Nucleotides that appear in lower case were added to provide sticky ends to aid in cloning. The nucleotides may be cloned into the Bgl II site of pUC19 then excised with Eco RI and Hind III to generate larger DNA fragments which will then be used as probes.

HTLV-I 21 bp repeat 1: (−253 to −233)
    5'-gatctAAGGCTCTGACGTCTCCCCa-3' (Seq. I.D. No. 41)

HTLV-I 21 bp repeat 2: (−203 to −183)
    5'-gatctAGGCCCTGACGTGTCCCCa-3' (Seq. I.D. No. 42)

HTLV-I 21 bp repeat 3: (−104 to −84)
    5'-gatctGGCGTTGACGACAACCCCa-3' (Seq. I.D. No. 43)

HTLV-I 21 bp repeat 1,2 (−253 to −183)
    5'-gatctAAGGCTCTGACGTCTCCCCCCGGAGGGCAGCTCAGCACCGGCTCG
    GGCTAGGCCCTGACGTGTCCCCa-3' (Seq. I.D. No. 44)

HTLV-I AP-2 site: (−117 to −91)
    5'-gatctCCACCAAGAACCACCCATTTCCTa-3' (Seq. I.D. No. 45)

human c-fos CRE: (−67 tl −51)
    5'-gatctGCCCGTGACGTTTACACa-3' (Seq. I.D. No. 46)

IL2Rα NK-κB site: (−(275 to −249)
    5'-gatctCAACGGCAGGGGAATCTCCCTCTCCTTa-3' (Seq. I.D. No. 47)

consensus c-myc site: 5'-CACGTG-3'
consensus AP-1 site: 5'-TGAGTCA-3'

Appropriate flanking sequences are ligated to one or both ends of the consensus c-myc site or the consensus AP-1 site as required.

Example 3

Screening peptides by EMSA for ability to disrupt Tax-CREB interaction

The HTLV-I transactivator Tax enhances the binding of CREB to the 21 bp repeat sequences contained in the HTLV-I LTR (Zhao and Giam (1992) PNAS 89:7070–7074; Franklin et al. 1993 J. Biol. Chem. 268:21225–21231; Wagner and Green, 1993 Science 262:395–399). We are testing whether peptides representing portions of the primary sequence of Tax can disrupt the Tax-CREB interaction as measured by EMSA.

Purified recombinant CREB was isolated as previously published (Franklin et al. 1993 J. Biol. Chem. 268:21225–21231) and active DNA-binding CREB was purified by heparin-agarose chromatography. Purified recombinant TaxH6 (contains a six-histidine purification tag at the C-terminus of Tax) was isolated an purified as previously published (Zhao and Giam (1991) PNAS 88:12445–11449; Franklin et al. 1993 J. Biol. Chem. 268:21225–21231). Peptides were synthesized and purified as described in Example 1. The third HTLV-I 21 bp repeat (Seq. ID. No. 43) was cloned into the Bgl II site of pUC19. The 70 bp DNA probe fragment was excised with Kpn I and Hind III, phosphatased and gel purified.

EMSA reactions contained 0.1–2.0 nM [$^{32}$P]end-labeled double stranded site 3 probe, 5–50 ng poly (dI-dC) carrier DNA, 1–5 nM purified recombinant CREB, 100–200 nM purified recombinant TaxH6, 15 mM HEPES pH 8.0, 1.5% DMSO, 25 mM Tris-HCl pH 7.9, 6.25 mM MgCl$_2$, 0.5 mM EDTA, 0.5 mM DTT, 60–120 mM KCl, and 10% (v/v) glycerol, and candidate peptide inhibitors in a 20 μl reaction volume. CREB was incubated with the peptides or mock buffer (5% DMSO 50 mM HEPES pH 8.0) for 2–5 min. at room temp. then TaxH6 and DNA mixture were added. The complete reaction mixture was incubated 10–20 min. further at room temp. then analyzed on 5% non-denaturing polyacrylamide gels (49:1, acrylamide:N,N-methylene bisacrylamide). The electrophoresis buffer contained 0.04M Tris, 0.306M glycine, pH 8.5, and 0.1% Nonidet P-40. Gels were dried were autoradiographed. Relative amounts of protein-DNA complex were quantitated using Phosphor Image Analysis.

The primary amino acid sequence of Tax was divided into 29 peptides 20 amino adds in length with an overlap of eight amino acids (see Detailed Description of the Invention and Example 1). The number of the first amino acid in each peptide corresponds to its position in the primary sequence of Tax. Six peptides were tested by EMSA for inhibition of Tax-mediated enhancement. The percentage of radiolabeled DNA probe shifted into protein-DNA complexes in each reaction was quantitated by phosphorimage analysis. Fold enhancement was calculated by dividing the amount of probe shifted in each reaction by the amount of probe shifted in reactions containing CREB, DNA and mock peptide buffer (Table 1). Reactions in Table 1 contained 0.5 nM radiolabeled DNA probe, 10 ng poly dIdC, 1.25% v/v DMSO, 12.5 mM HEPES pH 8.0, 25 mM Tris pH 7.9, 6.25 mM MgCl2, 75 mM KCl, 0.5 mM EDTA, 0.5 mM DTT, 10% v/v glycerol, and CREB, Tax and peptide as indicated in a final volume of 20 μL.

TABLE 1

| CREB | Tax | peptide, [conc. μM] | fold enhancement |
|---|---|---|---|
| 3.4 nM | 0 | 0 | 1.0 |
| 3.4 nM | 200 nM | 0 | 3.9 |
| 3.4 nM | 200 nM | TX49 [125] | 3.2 |

TABLE 1-continued

| CREB | Tax | peptide, [conc. µM] | fold enhancement |
|---|---|---|---|
| 3.4 nM | 200 nM | TX109 [125] | 4.1 |
| 3.4 nM | 200 nM | TX121 [125] | 4.7 |
| 3.4 nM | 200 nM | TX229 [125] | 4.7 |
| 3.4 nM | 200 nM | TX277 [125] | 4.7 |
| 3.4 nM | 200 nM | TX301 [5] | 0.4 |

The amount of protein-DNA complex increased 3.9 fold when Tax was present in the reaction. Peptide TX49 (SEQ ID No. 5) slightly decreased complex formation. Peptide TX301 (SEQ ID No. 26) completely inhibited Tax mediated enhancement of CREB binding to DNA. Peptides TX121, TX229, TX277(SEQ ID Nos. 11, 20, 24) and to a lesser extent peptide TX109 (Seq. ID No. 10) slightly enhanced complex formation. Note that TX301, which showed the greatest level of inhibition, was present at a much lower concentration than the other peptides tested (due to limited solubility in aqueous solutions). The slight enhancement seen by four of the peptides may be nonspecific and attributable to increased peptide concentration in the reaction.

Peptide TX301, which showed the greatest level of inhibition, peptide TX277, which showed slight enhancement, and peptide TX313 (Seq. ID No. 27) which overlaps TX301 by 8 amino acids, were titrated to determine if they affected Tax mediated enhancement in a dose dependent fashion (Tables 2–4).

Reactions in Table 2 contained 0.5 nM radiolabeled DNA probe, 10 ng poly dIdC, 1.75% v/v DMSO, 17.5 mM HEPES pH 8.0, 25 mM Tris pH 7.9, 6.25 mM MgCl2, 75 mM KCl, 0.5 mM EDTA, 0.5 mM DTT, 10% v/v glycerol, and CREB, Tax and peptide as indicated in a final volume of 20 µL. Protein-DNA complexes were quantitated by phosphorimage analysis. Fold enhancement was calculated by dividing the amount of complex formed in each reaction by the amount of complex formed in a reaction containing CREB, DNA, mock Tax buffer and mock peptide buffer.

TABLE 2

| CREB | Tax | TX301 (µM) | fold enhancement |
|---|---|---|---|
| 3.4 nM | 0 | 0.00 | 1.00 |
| 3.4 nM | 200 nM | 0.00 | 4.28 |
| 3.4 nM | 200 nM | 1.25 | 1.02 |
| 3.4 nM | 200 nM | 2.50 | 0.67 |
| 3.4 nM | 200 nM | 5.00 | 0.44 |

Reactions in Table 3 contained 0.5 nM radiolabeled DNA probe, 10 ng poly dIdC, 1.75% v/v DMSO, 17.5 mM HEPES pH 8.0, 25 mM Tris pH 7.9, 6.25 mM MgCl2, 75 mM KCl, 0.5 mM EDTA, 0.5 mM DTT, 10% v/v glycerol, and CREB, Tax and peptide as indicated in a final volume of 20 µL. Amount of complex was quantitated by densitometry (PDI). Fold enhancement was calculated by dividing the amount of complex formed in each reaction by the amount of complex formed in a reaction containing CREB, DNA, mock Tax buffer and mock peptide buffer.

TABLE 3

| CREB | Tax | TX277 (µM) | fold enhancement |
|---|---|---|---|
| 3.4 nM | 0 | 0 | 1.00 |
| 3.4 nM | 200 nM | 0 | 2.78 |
| 3.4 nM | 200 nM | 35 | 2.60 |
| 3.4 nM | 200 nM | 70 | 2.78 |
| 3.4 nM | 200 nM | 140 | 2.62 |

Reactions in Table 4 contained 0.5 nM radiolabeled DNA probe, 10 ng poly dIdC, 1.75% v/v DMSO, 17.5 mM HEPES pH 8.0, 25 mM Tris pH 7.9, 6.25 mM MgCl2, 75 mM KCl, 0.5 mM EDTA, 0.5 mM DTT, 10% v/v glycerol, and CREB, Tax and peptide as indicated in a final volume of 20 µL. Amount of complex was quantitated by densitometry (PDI). Fold enhancement was calculated by divided the amount of complex formed in each reaction by the amount of complex formed in a reaction containing CREB, DNA, mock Tax buffer and mock peptide buffer.

TABLE 4

| CREB | Tax | TX313 (µM) | fold enhancement |
|---|---|---|---|
| 3.4 nM | 0 | 0 | 1.00 |
| 3.4 nM | 200 nM | 0 | 4.48 |
| 3.4 nM | 200 nM | 35 | 5.16 |
| 3.4 nM | 200 nM | 70 | 5.60 |
| 3.4 nM | 200 nM | 140 | 4.49 |

Peptide TX301 inhibition of Tax-mediated enhancement of CREB binding to DNA was dose dependent (Table 2). By contrast, peptide TX277 had no effect at any concentration tested (Table 3). These data demonstrate that the inhibition is attributable to specific peptide sequences rather than to the presence of a molar excess of peptide in the reaction. Peptide TX313 did not have a dose dependent affect and showed slight enhancement of complex formation at some concentrations (Table 4).

Eight amino acids at the C-terminus of TX301 overlap with eight amino acids at the amino terminus of TX313. In titration experiments TX301 inhibited Tax in a dose dependent fashion while TX313 showed slight enhancement and no dose dependence (Tables 2, 4). This result suggested that the amino-terminal portion of TX301 contains the inhibitory activity. To further investigate this, the 20 amino acid sequence of TX301 was divided into 10 amino acid blocks with an overlap of eight. These peptides were tested in EMSA at concentrations of 25 µM (Table 5).

Reactions in Table 5 contained 0.5 nM radiolabeled DNA probe, 10 ng poly dIdC, 1.50% v/v DMSO, 15 mM HEPES pH 8.0, 25 mM Tris pH 7.9, 6.25 mM MgCl2, 75 mM KCl, 0.5 mM EDTA, 0.5 mM DTT, 10% v/v glycerol, and CREB, Tax and peptide as indicated in a final volume of 20 µL. Peptide concentrations were determined by quantitative amino acid analysis. Protein-DNA complexes were quantitated by phosphorimage analysis. Fold enhancement was calculated by dividing the amount of complex formed in each reaction by the amount of complex formed in a reaction containing CREB, DNA, mock Tax buffer and mock peptide buffer.

TABLE 5

| CREB | Tax | peptide | fold enhancement |
|---|---|---|---|
| 2.3 nM | 0 | 0 | 1.0 |
| 2.3 nM | 200 nM | 0 | 3.9 |
| 2.3 nM | 200 nM | TX301–310 (ID48) | 0.0 |

TABLE 5-continued

| CREB | Tax | peptide | fold enhancement |
|---|---|---|---|
| 2.3 nM | 200 nM | TX303–313 (ID49) | 1.5 |
| 2.3 nM | 200 nM | TX305–315 (ID50) | 6.0 |
| 2.3 nM | 200 nM | TX307–317 (ID51) | 7.0 |
| 2.3 nM | 200 nM | TX311–321 (ID52) | 5.6 |
| 2.3 nM | 200 nM | TX315–325 (ID53) | 3.4 |

Peptides containing amino acids 301 to 310 and 303 to 313 from the primary amino acid sequence of Tax inhibited Tax to varying extents while peptides encompassing the more C-terminal portion of peptide TX301 and the amino-terminal portion of peptide TX313 showed slight enhancement or had no effect. These data are consistent with the previously determined activities of the TX301 and TX313 20mers in titration experiments. Based on the data in Tables 1–4 the TX301 20mer (Seq. ID No. 26) and the TX301–310 and TX303–313 (SEQ ID Nos. 48, 49) are preferred inhibitors. TX49, which showed slight inhibition in Table 1, and TX313 and 10mers within which showed some enhancement remain candidate inhibitors.

Our preferred Tax inhibitor TX301–310 (Seq. ID No. 48) contains ten amino acids arranged as in the primary sequence of Tax. If this peptide competes with native Tax for binding to CREB, then scrambling the sequence of these 10 amino acids ought to decrease inhibitory activity. FIG. 1 shows that TX301–inhibits Tax in a dose dependent manner and 50% inhibition is observed at 100 fold lower concentration than with the scrambled peptide. These data confirm that TX301–310 specifically inhibits Tax mediated enhancement of CREB binding to DNA. While TX301, TX301–310, and TX303–313 are potent inhibitors of Tax, they are sparingly soluble in aqueous solution. We made more soluble versions of the TX301–310 inhibitor by adding glutamic acid residues and glycine linkers to the sequence. These peptides sequences and their effects in EMSA are shown in Table 6.

Reactions in Table 6 contained 0.5 nM radiolabeled DNA probe, 10 ng poly dIdC, 1.50% v/v DMSO, 15 mM HEPES pH 8.0, 25 mM Tris pH 7.9, 6.25 mM MgCl2, 75 mM KCl, 0.5 mM EDTA, 0.5 mM DTT, 10% v/v glycerol, and CREB, Tax and peptide as indicated in a final volume of 20 μL. Peptide concentrations were determined by quantitative amino acid analysis. Protein-DNA complexes were quantitated by phosphorimage analysis. Fold enhancement was calculated by dividing the amount of complex formed in each reaction by the amount of complex formed in a reaction containing CREB, DNA, mock Tax buffer and mock peptide buffer.

TABLE 6

| Seq ID No. [conc] μM | aa sequence | CREB | Tax | fold enhancement |
|---|---|---|---|---|
|  |  | 3.4 nM | 0 | 1.0 |
|  |  | 3.4 nM | 200 nM | 25.5 |
| #56 [5.5] | EEGGSFHSLHLLFEEE | 3.4 nM | 200 nM | 9.4 |
| #56 [16.5] | EEGGSFHSLHLLFEEE | 3.4 nM | 200 nM | 2.9 |
| #54 [6.0] | SFHSLHLLFEEE | 3.4 nM | 200 nM | 4.5 |
| #54 [17.9] | SFHSLHLLFEEE | 3.4 nM | 200 nM | 0.8 |
| #55 [6.2] | EEGGSFHSLHLLFE | 3.4 nM | 200 nM | 6.6 |
| #55 [18.6] | EEGGSFHSLHLLFE | 3.4 nM | 200 nM | 0.9 |
| #48, [3.75] | SFHSLHLLFEE | 3.4 nM | 200 nM | 0.0 |

These more soluble peptides also inhibit Tax-mediated enhancement of CREB binding to DNA. Therefore SEQ ID 54, 55, 56 are added to our preferred list of inhibitors.

The experiments in Tables 1, 2, and 5 showed that a given amount of protein-DNA complex is formed when CREB and DNA are incubated, that Tax increased the amount of complex formed, and that peptide TX301 decreases the amount of complex formed. Interestingly, at the higher concentrations tested, peptide TX301 decreased the the amount of complex formed to a level below that formed in reactions containing only CREB and DNA (i.e., fold enhancement is less than 1.0). In several other experiments we have observed TX301 inhibition of CREB binding in the absence of Tax. One possible explanation for this observation is that TX301 is binding to DNA. We think this is highly unlikely since the binding reactions contain a large excess of carrier DNA and the amino acid composition of the peptide does not include any lysine or arginine residues. We think TX301 inhibits Tax-mediated enhancement of CREB binding by mimicking the native Tax protein and inhibits CREB binding in the absence of Tax for the same reason. CREB contains a leucine zipper motif and binds to DNA as a dimer. A recent publication reports that Tax enhances CREB binding to DNA by promoting CREB dimerization (Wagner and Green, 1993 Science 262:395–399). We believe TX301 peptide competes with Tax protein for binding to CREB and promoting dimer formation. Thus, in the presence of Tax a molar excess of TX301 competitively inhibits Tax-mediated enhancement and in the absence of Tax TX301 interacts with CREB monomer and prevents the DNA-binding dimer from forming.

Example 4

Mammalian Cell Tissue Assay

Transcription is measured directly or indirectly by linking a promoter or enhancer region to the reporter chloramphenicol acetyl transferase (CAT) or luciferase on a suitable plasmid. This plasmid is then introduced into the cultured cell lines. Foreign DNA is introduced into cultured eukaryotic cells (transfected) either transiently or stably. Mechanisms for introducing DNA into cells include calcium phosphate transfection, transfection using DEAE-Dextran, transfection by electroporation, and liposome-mediated transfection (detailed in *Current Protocols in Molecular Biology*, ed. Ausubel et. al. (1991), John Wiley & Sons, New York) with calcium phosphate transfection being the usual method. The relative level of transcription directed from that promoter is then measured directly by harvesting the cellular RNA and probing for the mRNA of the reporter gene or indirectly by preparing a cell lysate and assaying for the activity of the reporter gene product. Methods for direct analysis or RNA after transfection, for harvesting cells and performing CAT assays and for harvesting cells and performing luciferase assays are detailed in *Current Protocols in Molecular Biology*, ed. Ausubel et. al. (1991), John Wiley & Sons, New York).

Transfection assays can be used to screen a number of compounds for the ability to inhibit Tax transactivation or alternatively to evaluate an inhibitory compound already characterized in a cell free transcription assay for the ability to inhibit Tax transactivation in cultured cells and to begin to evaluate its cytotoxicity. Many different cell lines may be used in the transfection assay. The monkey kidney cell lines CV-I (ATCC Accession No. CCL70), and COS-1 (ATCC Accession No. CRL 1650) may be used since they are readily infected. The cell lines used to prepare extracts for the cell free run-off transcription assay will also be used for the transfection assay. Addition cell lines that might be used include Jurkat uninfected human T lymphocyte, HUT 78 an HTLV negative human T-lymphocyte cell line, C81-66-45 an HTLV-I immortalized nonviral producer (produces Tax), HUT-102 (Advanced Biotechnologies, Inc., Columbia, Md. and ATCC Accession No. TIB 162) HTLV-I producer T lymphocyte line, MT2 HTLV-I producer T-lymphocyte cell line C3-44 HTLV-II producer T-lymphocyte cell line (these lines are used in Sodroski et al., (1984) Science 225:381–385). In addition to human T-lymphocytes, other cell types found in the peripheral blood stream (that might be exposed to the inhibitor) may also be used. Some of the promoter constructs that can be characterized are described above.

A number of compounds are rapidly screened for inhibition of transcription from the HTLV-I LTR, inhibition of transcription from a reference promoter such as the Rous sarcoma virus RSV-LTR, and cytotoxicity in a random screening assay as follows. Transiently co-transfect a Tax-producing human T-lymphocyte cell line (e.g., C81-66-45 or induced CEMTax) with a plasmid containing the HTLV-I LTR upstream of the firefly luciferase gene and another plasmid containing the RSV LTR upstream of the CAT gene. Aliquot the transfected cells into a 96 well microtiter plate. To the different wells add either a mock inhibitor (buffer only) or increasing amounts of different inhibitors. Allow the cells to continue growing for 12–48 hrs. Analyze one fraction of the cells in one well for viability by trypan blue staining. Analyze another fraction of the cells for transcription from the HTLV-I LTR by measuring luciferase activity. Analyze another portion of the cell from that well for transcription from the RSV-LTR by measuring CAT activity. (Alternatively, prepare one sample of cellular RNA and probe for both CAT and RSV mRNA by Northern blotting). Normalize the results of wells containing candidate inhibitors to wells containing mock inhibitors.

Results and interpretations of the transfection assay are as follows:

(A) If a candidate inhibitor has no effect on any of the three assay points (cell viability, Tax-dependent transcription, Tax independent transcription) it is not inhibitory at the concentrations tested or it is not able to enter the cell and the cell nucleus at sufficient concentrations to inhibit. If this result is observed for a candidate inhibitor that inhibited Tax-dependent transcription in a cell free assay, then it would be useful to evaluate uptake by using a radiolabelled inhibitor and isolating whole cells as well as cytoplasmic and nuclear cell fractions.

(B) If a candidate inhibitor results in no viable cells then it may or may not inhibit Tax-mediated transcription and should be tested at lower concentrations.

(C) If a candidate inhibitor results in decreased transcription from both the HTLV-I LTR and the RSV-LTR then it may interact either directly with components of the general transcriptional machinery (RNAP II and associated general factors) or influence the availability of these components. If this inhibitor did not dramatically decrease cell viability, then it should be investigated further. Random modifications of the inhibitor could be made and screened (e.g., change 1 amino acid at a time, or lengthen or shorten) or its target could be determined by methods discussed in another section (radiolabelling and probing libraries, using as an affinity column).

(D) An inhibitor abolishes transcription from the HTLV-I LTR and has no effect on transcription from the reference promoter or cell viability. This may be a strong candidate for a product, however, note that it abolished rather than decreased transcription from the HTLV-I promoter. One would expect the HTLV-I LTR to be transcribed at a very low level in the absence of Tax, so abolition is unexpected. One possibility is that non-productive transcription complexes were locked onto the promoter. Since Tax activates transcription from a number of cellular genes this inhibitor could have potential deleterious effects on the cell (although none were observed as measured by cell viability over the period of this assay). Thus it would be informative to screen RNA prepared from cells treated and untreated with this inhibitor for mRNAs from known Tax responsive cellular genes (c-fos, IL-2, IL2-Rα, GM-CSF, humβ pol).

(E) An inhibitor decreases transcription from the HTLV-I LTR and has no effect on cell viability or transcription from the RSV promoter. This result indicates a strong candidate for an inhibitor, however further investigation is required. Tax is thought to activate transcription of the HTLV-I LTR through a CRE but Tax is thought to activate other cellular promoters through different DNA sequences including an NF-κB element. Since a number of these genes are involved in regulation of cell growth, it may or may not be necessary to inhibit Tax mediated activation of these promoters as well as the viral promoter to inhibit cellular transformation and development of ATL. Thus one could probe mRNA levels of these genes in non-Tax-expressing cells, Tax-expressing cells, and Tax expressing cells treated with the inhibitor. Alternatively, one could proceed to animal models and look for inhibition of Tax-mediated tumor promotion.

Example 5

In vivo Assay to Determine Efficacy

Inhibitor molecules are tested for the ability to slow or reverse HAM/TSP symptoms in rats. WKA rats are intravenously injected with $2\times10^6$ cells from a human HTLV-I infected cell line as described by Kushida et al. ((1993) Jpn. J. Cancer Res. 84:831–833) or are injected intraperitoneally with $10^7$ cells from an HTLV-I immortalized rat cell line as described by Ishiguro et al. ((1992) J. Exp. Med. 176:981–989). HTLV-I antibody titers and development of hind leg spastic paraparesis are evaluated biweekly. Typical onset of hind leg spastic paraparesis is 16–20 months post injection (Kushida et al., (1993) Jpn. J. Cancer Res. 84:831–833; Ishiguro et al., (1992) J. Exp. Med. 176:981–989). At 16 mo. post injection, one fourth of the subject group is given weekly intraperitoneal injections of inhibitor and one fourth of the group is given injections of mock inhibitor. The two subgroups are monitored for development of hind leg spastic paraparesis. The inhibitor is evaluated for the ability to prevent, delay onset, or lessen severity of HAM/TSP symptoms. The remaining half of the initial subject group is untreated and monitored. The inhibitor is tested as above against mock inhibitor on rats that eventually develop TSP/HAM symptoms for the ability to alleviate symptoms and slow progression of the disease. Antibody titer and spasticity are monitored weekly through month 24. The rats are then euthanized and neuropathological examinations are performed. Number and location of spinal cord lesions, myelin and axon damage, and macrophage infiltration are determined.

Inhibitor molecules are tested for the ability to prevent or slow progression of lymphoblastic lymphomas in SCID mice models of ATL. SCID mice are intraperitoneally injected with $10^7$ peripheral blood cells from ATL patients as described by Feuer et al. ((1993) Blood 82:722–731) and Kondo et al. ((1993) Blood 82:2501–2509). Engraphment of human cells is evaluated 3 weeks post injection. Mice successfully engraphed with HTLV-I infected cells are divided into two groups. Daily intravenous injection of inhibitor is begun immediately in one group and 6 weeks from the date of PBL inoculation in the second group. Blood is taken weekly from both groups and the presence of genomic HTLV-I DNA is determined by quantitative PCR. At 16 weeks from the date of PBL inoculation, both groups of mice are euthanized and autopsied (mice that do not survive to 16 weeks are also autopsied). Tumors of the spleen, thymus and lymph nodes are counted and measured if possible.

Inhibitor molecules are tested for the ability to prevent or slow progression of fibroblastic tumors in transgenic mice models of HTLV-I.

Transgenic and/or syngenic mouse models are conducted by introducing the target DNA sequence into a mouse and then exposing the mouse to the inhibitor. Transgenic mice have been produced previously [U.S. Pat. No. 4,736,866; U.S. Pat. No. 5,175,385; and U.S. Pat. No. 5,175,384]. At least three lines of transgenic mice carrying the tax gene have been reported in the literature (Nerenberg et al., (1987) Science 237:1324–1343; Hinrichs et al., (1987) Science 237:1340–1343; Nerenberg (1989) Amer. J. Pathol. 135:1025–1033). These mice begin to develop fibroblastic tumors approximately 6 months after birth. Transgenic mice expressing the tax gene are treated with inhibitors prior to tumor development and compared to a control group of transgenic mice treat with a mock inhibitor. Inhibitors that delay or abolish tumor development and inhibitors that decrease the number and size of tumors in the test group of mice are further characterized. Inhibitors are also tested on transgenic mice that have already developed tumors for the ability to abolish or decrease the size of tumors.

A second and more expedient method to screen inhibitors uses syngenic mice injected with tumor cells prepared from transgenic mice. The syngenic mice begin to develop tumors as quickly as seven days post injection. Transgenic mice derived tumor cell lines are established as described in Green et al. ((1989) Mol. Cell. Biol. 9:4731–4737) and Kitajima et al. ((1992) J. Biol. Chem. 267:2581–25888). Syngenic mice are injected with tumor cell lines as described in Kitajima et al. ((1992) Science 258:1792–1795) and Kitajima et al. ((1992) J. Biol. Chem. 267:2581–25888). Inhibitors are administered by intraperitoneal injection, or using the delivery systems described in another section. Tumor size is evaluated 7–21 days post treatment with inhibitor by excising and determining the weight of the the tumor.

Example 6

Obtention of Inhibitor of Hepatitis B Protein X (Protein pX)

The human hepatits B virus (HBV) genome encodes a transactivator protein pX that may be functionally similar to the HTLV-I Tax protein although they are not similar in sequence. Transactivation of both viral promoters is though to occur through a CRE like elements (HTLV-I 21 bp repeat, HBV XRE). Factor and Shaul (Oncogene (1990) 5:867–872) showed that Tax can transactivate the HBV promoter, that both Tax and pX can transactivate promoters containing NF-κB binding sites, and that both are effective in similar concentration ranges. MaGuire et al. ((1991) Science 252:842–844) reported that HBV X protein increases the binding of CREB and ATF-2 to HBV promoter sequences. These observations suggest that pX and Tax activate transcription through a similar mechanism and perhaps through the same transcription factors. Thus, we expect an inhibitor of Tax to also inhibit pX activity. We will test this by screening Tax inhibitors for the ability to inhibit pX activity by in vitro transcription and EMSA. Rather than lymphocyte extracts, hepatocyte extracts will be used (HepG2, Dinter et al., (1987) EMBO 6:567–613). Recombinant pX will be expressed in pET8C-hbx (Wu et al., (1990) Cell 63:687–695) and purified. An oligonucleotide containing the XRE 5'-GTGTTTGCTGACGCAACCCCAC-3' (Seq. I.D. 40) and recombinant ATF and CREB proteins as listed in 2a will be used in the EMSA. The core promoter sequences of HBV (nt1466–1987; Roossinck et al. 1986 MCB 6:1393–1400) will be used in the in vitro transcription assays.

Example 7

Titration of TX301-310 and a Scramble Peptide (SCM2) in EDTA

An audiograph of TX301-310 (SEQ. ID. NO. 48) titration in EMSA was prepared. The audiograph containing lanes 0–9 showed reactions of 0.5 nM radiolabeled DNA probe, 10 ng poly dIdC, 1.5% v/v DMSO, 15 mM HEPES pH 8.0, 25 mM Tris pH 7.9, 6.25 mM MgCl$_2$, 75 mM KCl, 0.5 mM EDTA, 0.5 mM DTT, and 10% v/v glycerol in a final volume of 20 µL. Reactions in lanes 1–9 contained 2.3 nM CREB. Reactions in lanes 2–9 contained 200 nM Tax. Peptide TX301-310 (SEQ. ID. NO. 48) was included in reactions of lanes 309 at concentrations indicated in Table 7.

Table 7 shows quantitation of the autoradiograph of TX301-310 (SEQ. ID. NO. 48). Peptide concentrations were determined by quantitative amino acid analysis. Protein-DNA complexes were quantitated by phosphorimage analysis. Fold enhancement was calculated by dividing the amount of complex formed in each reaction by the amount of complex formed in a reaction containing CREB, DNA, mock Tax buffer and mock peptide buffer (reaction 1).

TABLE 7

| Rxn # | [Tx301-310] µM | fold enhancement |
|---|---|---|
| 1 | 0.0000 | 1.0 |
| 2 | 0.0000 | 11.2 |
| 3 | 0.0075 | 11.1 |
| 4 | 0.0150 | 8.9 |
| 5 | 0.0750 | 7.9 |
| 6 | 0.1500 | 8.7 |
| 7 | 0.7500 | 2.1 |
| 8 | 1.5000 | 0.8 |
| 9 | 3.7500 | 0.4 |

An audiograph of SCM2 (SEQ. ID. NO. 58) titration in EMSA was prepared. The audiograph showed reactions containing 2.3 nM CREB in lanes 1–8. Reactions in lanes 2–8 also contained 200 nM Tax. All reactions contained the nucleic acids and buffers used in the titration of TX301-310 (SEQ. ID. NO. 48). Peptide SCM2 was included in reactions of lanes 3–8 at concentrations listed in Table 8. Table 8 shows the quantitation of the autoradiograph of SCM2 (SEQ. ID. NO. 58). Peptide concentration and fold enhancement were determined as described above for TX301-310 (SEQ. ID. NO. 48).

TABLE 8

| Rxn # | [SCM2] μM | fold enhancement |
|---|---|---|
| 1 | 0.00 | 1.0 |
| 2 | 0.00 | 17.0 |
| 3 | 0.75 | 17.9 |
| 4 | 1.50 | 17.8 |
| 5 | 7.50 | 14.5 |
| 6 | 15.00 | 9.7 |
| 7 | 75.00 | 3.3 |
| 8 | 150.00 | 1.1 |

We claim:

1. A transactivating factor inhibitor comprising a peptide selected from the group consisting of SEQ. ID. NOS. 26, 48, 49, 54, 55, and 56, wherein said peptide inhibits Tax-dependent transcription.

2. The transactivating factor inhibitor of claim 1 wherein said peptide is SEQ. ID. NO. 26.

3. The transactivating factor inhibitor of claim 1 wherein said peptide is SEQ. ID. NO. 48.

4. The transactivating factor inhibitor of claim 1 wherein said peptide is SEQ. ID. NO. 49.

5. The transactivating factor inhibitor of claim 1 wherein said peptide is SEQ. ID. NO. 54.

6. The transactivating factor inhibitor of claim 1 wherein said peptide is SEQ. ID. NO. 55.

7. The transactivating factor inhibitor of claim 1 wherein said peptide is SEQ. ID. NO. 56.

8. The transactivating factor of claim 1 wherein said peptide further comprises an internalizing moiety selected from the group consisting of SEQ. ID. NOS. 38 and 39.

9. The transactivating factor inhibitor of claim 8 wherein said internalizing moiety is SEQ. ID. NO. 38.

10. The transactivating factor inhibitor of claim 8 wherein said internalizing moiety is SEQ. ID. NO. 39.

* * * * *